(12) United States Patent
Kogut et al.

(10) Patent No.: US 11,566,242 B2
(45) Date of Patent: *Jan. 31, 2023

(54) METHODS AND COMPOSITIONS FOR REPROGRAMMING CELLS

(71) Applicant: THE REGENTS OF THE UNIVERSITY OF COLORADO, A BODY CORPORATE, Denver, CO (US)

(72) Inventors: Igor Kogut, Aurora, CO (US); Dennis R. Roop, Greenwood Village, CO (US); Ganna Bilousova, Aurora, CO (US); Patrick S. McGrath, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 542 days.

This patent is subject to a terminal disclaimer.

(21) Appl. No.: 15/958,965

(22) Filed: Apr. 20, 2018

(65) Prior Publication Data

US 2018/0346933 A1 Dec. 6, 2018

Related U.S. Application Data

(63) Continuation-in-part of application No. PCT/US2016/063258, filed on Nov. 22, 2016.

(60) Provisional application No. 62/258,801, filed on Nov. 23, 2015.

(51) Int. Cl.
| | |
|---|---|
| C12N 15/90 | (2006.01) |
| C12N 15/113 | (2010.01) |
| C12N 5/074 | (2010.01) |
| A61K 31/713 | (2006.01) |
| A61P 17/00 | (2006.01) |
| A61K 35/28 | (2015.01) |
| C12N 5/077 | (2010.01) |
| C12N 9/22 | (2006.01) |
| C12N 15/11 | (2006.01) |

(52) U.S. Cl.
CPC .......... *C12N 15/113* (2013.01); *A61K 31/713* (2013.01); *A61K 35/28* (2013.01); *A61P 17/00* (2018.01); *C12N 5/0652* (2013.01); *C12N 5/0696* (2013.01); *C12N 9/22* (2013.01); *C12N 15/11* (2013.01); *C12N 15/907* (2013.01); *C12N 2310/141* (2013.01); *C12N 2310/20* (2017.05); *C12N 2330/31* (2013.01); *C12N 2500/60* (2013.01); *C12N 2501/115* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/65* (2013.01); *C12N 2506/1307* (2013.01); *C12N 2510/00* (2013.01); *C12N 2800/80* (2013.01)

(58) Field of Classification Search
CPC ...... C12N 15/113; C12N 5/0652; C12N 9/22; C12N 15/11; C12N 15/907; C12N 5/0696; C12N 2310/20; C12N 2800/80; C12N 2310/141; C12N 2330/31; C12N 2500/60; C12N 2501/602; C12N 2501/603; C12N 2501/604; C12N 2501/605; C12N 2501/606; C12N 2501/608; C12N 2501/65; C12N 2506/1307; C12N 2510/00; A61K 31/713; A61K 35/28; A61P 17/00
See application file for complete search history.

(56) References Cited

U.S. PATENT DOCUMENTS

| | | |
|---|---|---|
| 2013/0189741 A1 | 7/2013 | Meis et al. |
| 2014/0308746 A1 | 10/2014 | Rossi et al. |
| 2015/0232810 A1 | 8/2015 | Luo et al. |

FOREIGN PATENT DOCUMENTS

| | | | | |
|---|---|---|---|---|
| EP | 2202309 A1 | * 6/2010 | ............. | A61P 25/00 |
| WO | 2009152529 A2 | 12/2009 | | |
| WO | 2012012708 A1 | 1/2012 | | |
| WO | WO-2013086008 A1 | * 6/2013 | ............. | A61P 25/16 |
| WO | WO-2013173248 A2 | * 11/2013 | ........... | C12N 15/111 |
| WO | WO-2014071219 A1 | * 5/2014 | ............... | A61P 5/14 |
| WO | 2014122648 A1 | 8/2014 | | |
| WO | 2015117021 A1 | 8/2015 | | |
| WO | 2017077135 A1 | 5/2017 | | |

OTHER PUBLICATIONS

Ma et al. "miRNAs promote generation of porcine-induced pluripotent stem cells." Mol Cell Biochem. Apr. 2014;389(1-2):209-18. (Year: 2014).*
Phua et al. "Transfection Efficiency and Transgene Expression Kinetics of mRNA Delivered in Naked and Nanoparticle Format" J Control Release. Mar. 28, 2013; 166(3): 227-233. (Year: 2014).*
Poleganov et al. "Efficient Reprogramming of Human Fibroblastsand Blood-Derived Endothelial Progenitor Cells Using Nonmodified RNA for Reprogramming and Immune Evasion." Hum Gene Ther. Nov. 2015;26(11):751-66 (Year: 2015).*
Howden et al. "Simultaneous Reprogramming and Gene Correction of Patient Fibroblasts." Stem Cell Reports. Dec. 8, 2015;5(6):1109-1118.Epub Nov. 12, 2015. (Year: 2015).*
Thomas Scientific Product Catalog. Falcon Multiwell Plates for Cell Culture. Obtained from https://www.thomassci.com/Laboratory-Supplies/Plates/_/BD-FALCON-MULTIWELL-PLATES-FOR-CELL-CULTURE?q=6-Well%20Plate on Oct. 6, 2020. (Year: 2020).*

(Continued)

*Primary Examiner* — Titilayo Moloye
(74) *Attorney, Agent, or Firm* — Polsinelli PC

(57) ABSTRACT

The present disclosure relates to methods and compositions for reprogramming cells to a pluripotent state. In particular, it relates to an integration- and feeder cell-free method for reprogramming primary human fibroblast cells to induced pluripotent stem cells (iPSCs).

22 Claims, 35 Drawing Sheets

Specification includes a Sequence Listing.

(56) References Cited

OTHER PUBLICATIONS

Tsialikas et al. "LIN28: roles and regulation in development and beyond." Development (2015) 142 (14): 2397-2404. (Year: 2015).*
Bell, et al., "A Rapid Pipeline to Model Rare Neurodevelopmental Disorders with Simultaneous CRISPR/Cas9 Gene Editing," Stem Cells Translational Medicine, vol. 6, 2017, pp. 886-896.
Howden, et al., "A Cas9 Variant for Efficient Generation of Indel-Free Knockin or Gene-Corrected Human Pluripotent Stem Cells," Stem Cell Reports, vol. 7, 2016, pp. 1-10.
Howden, et al.,Simultaneous Reprogramming and Gene Correction of Patient Fibroblasts, Stem Cell Reports, vol. 5 ,2015 ,pp. 1109-1118.
Howden, et al., "Simultaneous reprogramming and gene editing of human fibroblasts," Nature Protocols, vol. 13, No. 5, 2018, pp. 875-898.
Huangfu, et al., "Induction of Pluripotent Stem Cells by Defined Factors is Greatly Improved by Small-Molecule Compounds," Nat Biotechnol, vol. 26, No. 7, 2008, pp. 795-797.
Kim, et al."Concurrent progress of reprogramming and gene correction to overcome therapeutic limitation of mutant ALK2-iPSC," Experimental & Molecular Medicine, vol. 48, 2016, pp. e237.
Tidball, et al., "Rapid Generation of Human Genetic Loss-of-Function iPSC Lines by Simultaneous Reprogramming and Gene Editing," Stem Cell Reports, vol. 9, 2017, pp. 725-731.
Zhou, et al., "Openly Accessible Microfluidic Liquid Handlers for Automated High-Throughput Nanoliter Cell Culture," Anal Chem, vol. 84, No. 5, 2012, pp. 2576-2584.
Bernall, J.A., "RNA-Based Tools for Nuclear Reprogramming and Lineage-Conversion: Toward Clinical Applications", J Cardiovasc Trans Res, vol. 6, No. 6, Jul. 13, 2013, pp. 956-968.
Bilousova, et al., "415 Highly Efficient RNA based reprogramming of a small number of human primary fibroblasts", Journal of Investigative Dermatology, vol. 136, No. 5, Apr. 20, 2016, pp. S73.
Martin, et al., "Highly Efficient microRNA-Enhanced mRNA Reprogramming of Diseased Human Fibroblasts in a Feeder-Free Culture System", Retrieved from the Internet: URL: http://assets.stemgent.com/files/1369/original/AppNoteMicroRNA_GK_061314.pdf [retrieved on Jan. 8, 2016], Jun. 2014, pp. 1-6.
Paull, et al., "Automated, high-throughput derivation, characterization and differentiation of induced pluripotent stem cells", Nature Methods, vol. 12, No. 9, Aug. 3, 2015, pp. 885-892.
Thornberry, et al., "Generation of Safe, Integration-free Human Induced Pluripotent Stem (iPS) Cells using the mRNA Reprogramming System", Stemgent Application Note Retrieved from the Internet: URL: https://www.reprocell.com/downloads/1536672810mRNA_Reprogramming_AppNote_Final.pdf [retrieved on Jun. 25, 2019], Jan. 1, 2013, pp. 1-5.
Warren, et al., "Feeder-Free Reprogramming of Human Fibroblasts with Messenger RNA", Current Protocols in Stem Cell Biology, vol. 27, No. 1, Nov. 2013, pp. 4A.6.1-4A.6.27.
Zhou, et al., "Adenoviral Gene Delivery Can Reprogram Human Fibroblasts to Induced Pluripotent Stem Cells", Stem Cells, vol. 27, No. 11, Aug. 20, 2009, pp. 2667-2674.
Bernal, "RNA-Based Tools for Nuclear Reprogramming and Lineage-Conversion: Toward Clinical Applications", J. Cardiovasc Trans Res, 2013, vol. 6, No. 6, pp. 956-968.

* cited by examiner

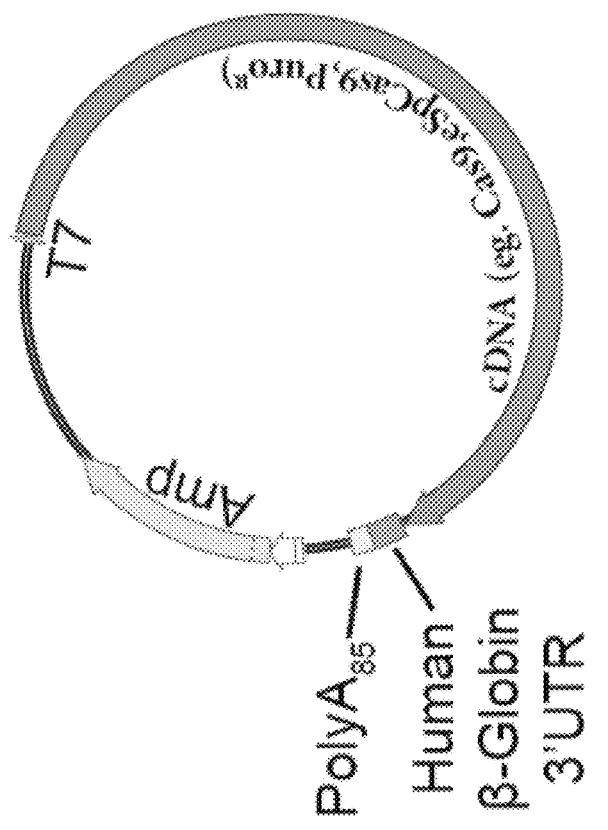
FIG. 18
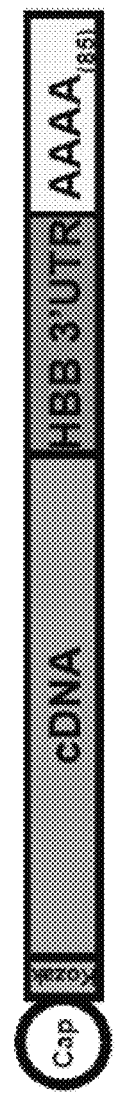
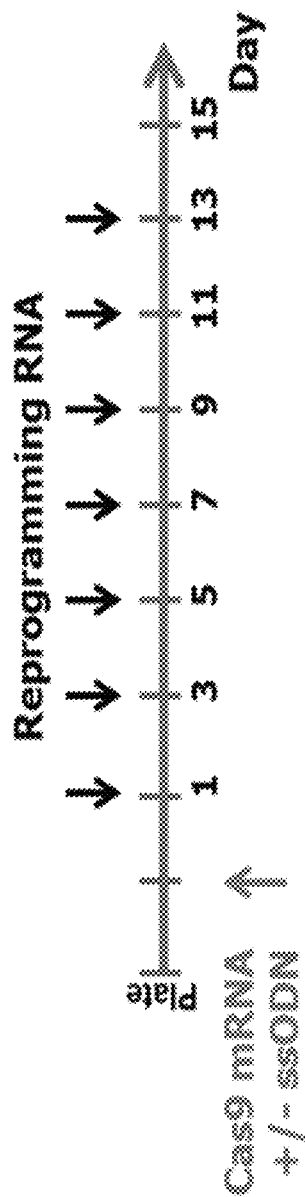
FIG. 19

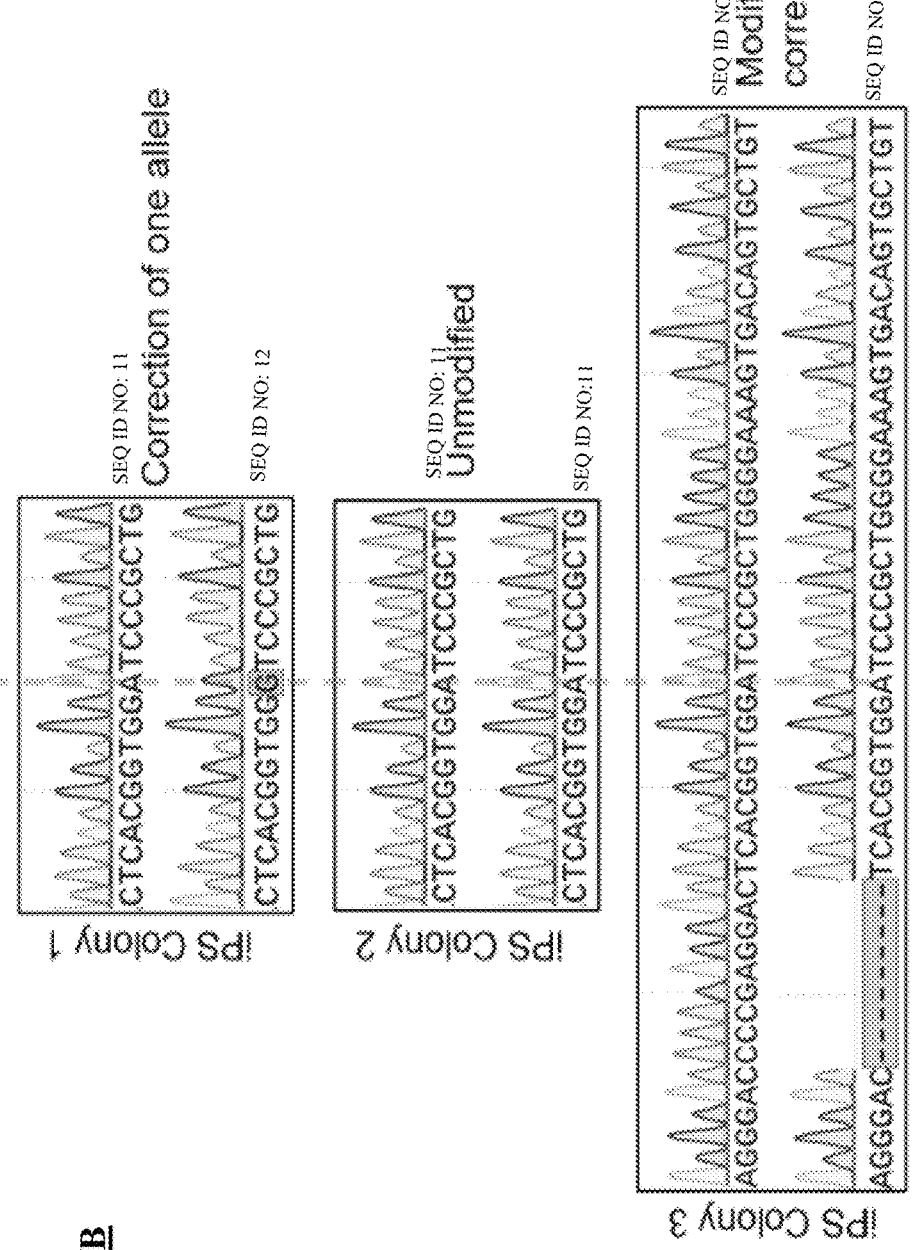

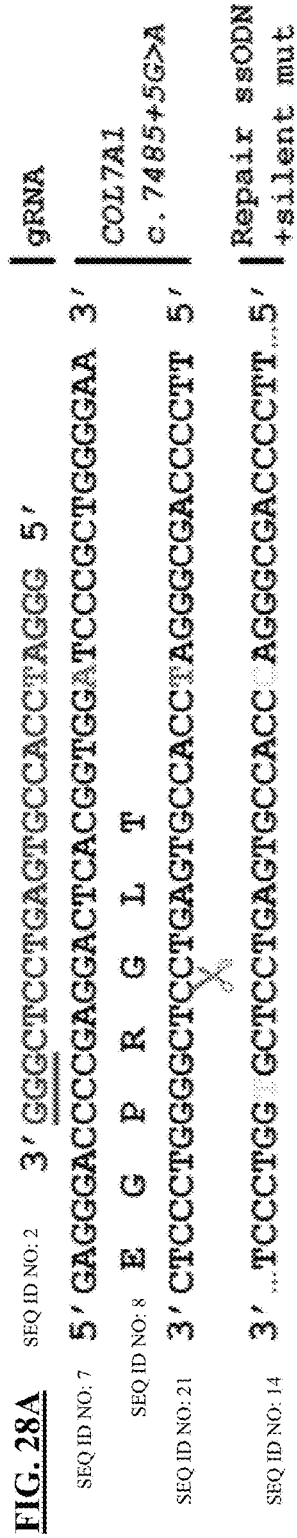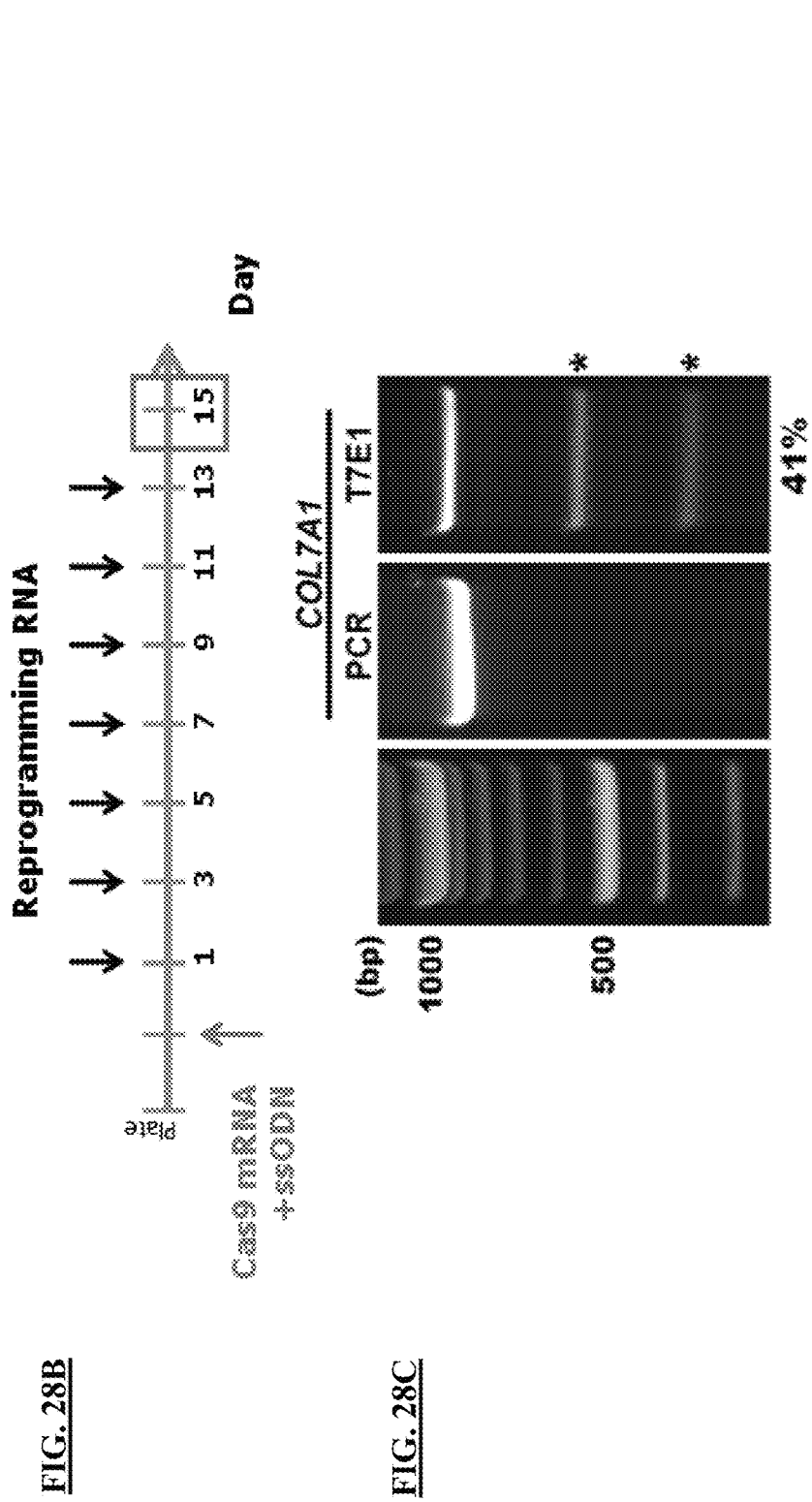
FIG. 28A
FIG. 28B
FIG. 28C

SEQUENCE LISTING

```
<160> NUMBER OF SEQ ID NOS: 24

<210> SEQ ID NO 1
<211> LENGTH: 23
<212> TYPE: DNA
<213> ORGANISM: Artificial Sequence
<220> FEATURE:
<223> OTHER INFORMATION: gRNA

<400> SEQUENCE: 1
ggtggccttg gtgctggctt ggg                                          23

<210> SEQ ID NO 2
<211> LENGTH: 23
<212> TYPE: DNA
<213> ORGANISM: Artificial Seqeunce
<220> FEATURE:
<223> OTHER INFORMATION: gRNA

<400> SEQUENCE: 2
gggatccacc gtgagtcctc ggg                                          23

<210> SEQ ID NO 3
<211> LENGTH: 23
<212> TYPE: DNA
<213> ORGANISM: Aritificial sequence

<400> SEQUENCE: 3
gccaaacata agtgaccaac agg                                          23

<210> SEQ ID NO 4
<211> LENGTH: 107
<212> TYPE: DNA
<213> ORGANISM: Homo sapiens

<400> SEQUENCE: 4
tccctcctct gcaccatgac ctcaacgact gcctggcctc ctacctggac aaggtgcgtg     60
ctctggagga ggccaacgcc gacctggaag tgaagatccg tgactgg                  107

<210> SEQ ID NO 5
<211> LENGTH: 118
<212> TYPE: DNA
<213> ORGANISM: Homo sapiens

<400> SEQUENCE: 5
cccgagcacc ttctcttcac tcagccaact gctcgctcgc tcacctccct cctctgcacc     60
tgctctggag gaggccaacg ccgacctgga agtgaagatc cgtgactggt accagagg      118

<210> SEQ ID NO 6
<211> LENGTH: 27
<212> TYPE: DNA
```

<213> ORGANISM: Homo sapiens

<400> SEQUENCE: 6
tccctcctct gcacctgctc tggagga                                    27

<210> SEQ ID NO 7
<211> LENGTH: 43
<212> TYPE: DNA
<213> ORGANISM: Homo sapiens

<400> SEQUENCE: 7
gagggacccc gaggactcac ggtggatccc gctggggaaa gtg                  43

<210> SEQ ID NO 8
<211> LENGTH: 7
<212> TYPE: PRT
<213> ORGANISM: Homo sapiens

<400> SEQUENCE: 8

Glu Gly Pro Arg Gly Leu Thr
1               5

<210> SEQ ID NO 9
<211> LENGTH: 43
<212> TYPE: DNA
<213> ORGANISM: Homo sapiens

<400> SEQUENCE: 9
cactttcccc agcgggatcc accgtgagtc ctcggggtcc ctc                  43

<210> SEQ ID NO 10
<211> LENGTH: 41
<212> TYPE: DNA
<213> ORGANISM: Artificial Sequence
<220> FEATURE:
<223> OTHER INFORMATION: ssODN

<400> SEQUENCE: 10
actttcccca gcgggaccca ccgtgagtcc tcgggtccc t                     41

<210> SEQ ID NO 11
<211> LENGTH: 19
<212> TYPE: DNA
<213> ORGANISM: Homo sapiens

<400> SEQUENCE: 11
ctcacggtgg atcccgctg                                             19

<210> SEQ ID NO 12
<211> LENGTH: 19
<212> TYPE: DNA
<213> ORGANISM: Homo sapiens

<400> SEQUENCE: 12
ctcacggtgg gtcccgctg                                             19

<210> SEQ ID NO 13
<211> LENGTH: 43
<212> TYPE: DNA
<213> ORGANISM: Homo sapiens

<400> SEQUENCE: 13
agggactcac ggtggatccc gctggggaaa gtgacagtgc tgt                  43

<210> SEQ ID NO 14
<211> LENGTH: 38
<212> TYPE: DNA
<213> ORGANISM: Artificial Sequence
<220> FEATURE:
<223> OTHER INFORMATION: ssODN

<400> SEQUENCE: 14
ttccccagcg ggacccaccg tgagtcctcg tggtccct                       38

<210> SEQ ID NO 15
<211> LENGTH: 39
<212> TYPE: DNA
<213> ORGANISM: Homo sapiens

<400> SEQUENCE: 15
gagggaccac gaggactcac ggtgggtccc gctggggaa                      39

<210> SEQ ID NO 16
<211> LENGTH: 39
<212> TYPE: DNA
<213> ORGANISM: Homo sapiens

<400> SEQUENCE: 16
gagggacccc gaggactcac ggtgggtccc gctggggaa                      39

<210> SEQ ID NO 17
<211> LENGTH: 39
<212> TYPE: DNA
<213> ORGANISM: Homo sapiens

<400> SEQUENCE: 17
gagggacccc gaggactcac ggtggatccc gctggggaa                      39

<210> SEQ ID NO 18
<211> LENGTH: 108
<212> TYPE: DNA
<213> ORGANISM: Homo sapiens

<400> SEQUENCE: 18
ggtggccttg gtgctggctt gggtggtggc tttggtggtg gctttgctgg tggtgatggg    60
cttctggtgg gcagtgagaa ggtgaccatg cagaacctca acgaccgc               108

<210> SEQ ID NO 19
<211> LENGTH: 108
<212> TYPE: DNA
<213> ORGANISM: Homo sapiens

<400> SEQUENCE: 19
ggtggccttg gtgctggctt gggtggtggc tttggtggtg gctttgctgg tggtgatggg    60
cttctggtgg gcagtgagaa ggtgaccatg cagaacctca acgactgc               108

<210> SEQ ID NO 20
<211> LENGTH: 97
<212> TYPE: DNA
<213> ORGANISM: Homo sapiens

<400> SEQUENCE: 20
ggtggccttg gtggtggct tggtggtgg ctttgctggt ggtgatgggc ttctggtggg      60
cagtgagaag gtgaccatgc agaacctcaa cgactgc                            97

```
<210> SEQ ID NO 21
<211> LENGTH: 39
<212> TYPE: DNA
<213> ORGANISM: Homo sapiens

<400> SEQUENCE: 21
ttccccagcg ggatccaccg tgagtcctcg gggtccctc                                39

<210> SEQ ID NO 22
<211> LENGTH: 36
<212> TYPE: PRT
<213> ORGANISM: Homo sapiens

<400> SEQUENCE: 22

Gly Gly Leu Gly Ala Gly Leu Gly Gly Gly Phe Gly Gly Gly Phe Ala
1               5                   10                  15

Gly Gly Asp Gly Leu Leu Val Gly Ser Glu Lys Val Thr Met Gln Asn
            20                  25                  30

Leu Asn Asp Arg
        35

<210> SEQ ID NO 23
<211> LENGTH: 108
<212> TYPE: DNA
<213> ORGANISM: Homo sapiens

<400> SEQUENCE: 23
gcggtcgttg aggttctgca tggtcacctt ctcactgccc accagaagcc catcaccacc         60
agcaaagcca ccaccaaagc caccacccaa gccagcacca aggccacc                     108

<210> SEQ ID NO 24
<211> LENGTH: 52
<212> TYPE: DNA
<213> ORGANISM: Homo sapiens

<400> SEQUENCE: 24
agggaccccg aggactcacg gtggatcccg ctggggaaag tgacagtgct gt                 52
```

METHODS AND COMPOSITIONS FOR REPROGRAMMING CELLS

CROSS-REFERENCE TO RELATED APPLICATION

The present application is a Continuation In Part (CIP) of, and claims priority to, PCT International Application No. PCT/US2016/063258, filed Nov. 22, 2016, which claims priority to U.S. Provisional Patent Application No. 62/258,801, filed Nov. 23, 2015, all of which are incorporated by reference herein in their entireties.

STATEMENT OF FEDERALLY FUNDED RESEARCH

This invention was made with government support under grant number AR059947 awarded by the National Institutes of Health and grant number W81XWH-12-1-0606 awarded by the US Department of Defense. The government has certain rights in the invention.

SEQUENCE LISTING

The present application contains a Sequence Listing which has been submitted in ASCII format via EFS-Web and is hereby incorporated herein by reference in its entirety. Said ASCII copy, created on Jul. 3, 2018 is named 373330-7100US1_SequenceListing_ST25.txt and is Five (5) kilobytes in size.

TECHNICAL FIELD

The present disclosure relates generally to methods and compositions for cell reprogramming. In particular, the present disclosure includes methods and compositions for reprogramming primary human fibroblast cells into induced pluripotent stem cells (iPSCs) in the absence of feeder cells.

BACKGROUND

The following description is provided to assist the understanding of the reader. None of the information provided or references cited is admitted to be prior art.

Reprogramming of differentiated somatic cells into induced pluripotent stem cells (iPSCs) through ectopic expression of a defined set of factors provides an unlimited supply of cells with embryonic stem cell (ESC) properties. The development of this reprogramming technology also holds great potential for the generation of patient-specific cells and tissues for therapeutic use.

BRIEF SUMMARY OF THE INVENTION

Disclosed herein are methods, compositions, and kits for the efficient, integration-free, feeder cell-free reprogramming of somatic cells, such as primary human fibroblast cells, seeded at a low initial density, into induced pluripotent stem cells (iPSCs) using modified mRNA (mod-mRNA). In one aspect, a method for cell reprogramming is provided. In one embodiment, the cell is a primary human fibroblast cell. In one embodiment the primary human fibroblast cell is a primary human neonatal fibroblast cell. In one embodiment the primary human fibroblast cell is a primary human adult fibroblast cell.

In one embodiment, the cells (e.g., primary human fibroblast cells) are seeded at a density of less than about 1000 cells/cm$^2$. In some embodiments, the cells (e.g., primary human fibroblast cells) are seeded at a density of less than about 100 cells/cm$^2$. In some embodiments, the cells (e.g., primary human fibroblast cells) are seeded at a density of less than about 10 cells/cm$^2$. In some embodiments, the cells (e.g., primary human fibroblast cells) are seeded at a density of less than about 1 cell/cm$^2$. Additionally or alternatively, in some embodiments, the reprogramming methods disclosed herein are applied to a single individually plated cell (e.g., a primary human fibroblast cell). In some embodiments, the cells (e.g., the primary human fibroblast cells) are cultured in the absence of feeder cells.

In one embodiment, the cells (e.g., primary human fibroblast cells) are transfected with a composition comprising a complexation buffer and a reprogramming mRNA cocktail. In one embodiment, the reprogramming mRNA cocktail comprises 100 to 1500 ng/10 cm$^2$ reprogramming mRNA. In one embodiment, the reprogramming mRNA cocktail comprises 50 to 600 ng/10 cm$^2$ reprogramming mRNAs. In one embodiment, the composition further comprises reprogramming miRNAs. In one embodiment, the composition comprises 1 to 40 pmoles/10 cm$^2$ reprogramming miRNAs.

In one embodiment, the reprogramming mRNA cocktail of the composition comprises Oct4 or Myo-D-Oct4 (M$_3$O), Sox2, and Klf4 in a 3:1:1 molar ratio. In some embodiments, the reprogramming mRNA cocktail further comprises one or more of c-Myc, Lin28A, or Nanog in a 1:1 molar ratio with Sox2 and Klf4. Additionally or alternatively, in one embodiment, the composition includes reprogramming miRNA which comprises miR-367 and miR-302s.

In one embodiment, the pH of the complexation buffer is about 7.3 to 8.4. In one embodiment, the pH of the complexation buffer is about 7.3. In one embodiment, the pH of the complexation buffer is about 7.4. In one embodiment, the pH of the complexation buffer is about 7.5. In one embodiment, the pH of the complexation buffer is about 7.6. In one embodiment, the pH of the complexation buffer is about 7.7. In one embodiment, the pH of the complexation buffer is about 7.8. In one embodiment, the pH of the complexation buffer is about 7.9. In one embodiment, the pH of the complexation buffer is about 8.0. In one embodiment, the pH of the complexation buffer is about 8.1. In one embodiment, the pH of the complexation buffer is about 8.2. In one embodiment, the pH of the complexation buffer is about 8.3. In one embodiment, the pH of the complexation buffer is about 8.4. In one embodiment, the pH of the complexation buffer is about 8.5. In one embodiment, the pH of the complexation buffer is about 8.6.

In one embodiment, the complexation buffer comprises OPTI-MEM® reduced serum medium. In one embodiment, the complexation buffer comprises phosphate-buffered saline (PBS).

In one embodiment, the transfection is performed at least 3 times. In one embodiment, the transfection is performed every other day. In one embodiment, the transfection is performed every third day.

In one embodiment, the cells are grown under conditions selected to increase levels of expression of endogenous pluripotency genes and chromatin modifiers, and to limit the increase in levels of innate immune response genes. In one embodiment, the endogenous pluripotency genes include NANOG, LIN28A, OCT4, SOX2, SALL4, GDF3, PRDM14, UTF1, NR5A2, DPPA2, DPPA4, NR6A1, TRIM71, LEFTY1, LEFTY2, ZFP42, and ZIC3. In one embodiment, the chromatin modifier genes include ASF1A, DNMT3A, DNMT3B, DNMT3L, and TET1. In one embodiment, the innate immune response genes include DDX58, which encodes retinoic acid-inducible gene 1 (RIG-I), IFIT1, IFNB1, OAS1, and IFNA1. In one embodiment, the cells are grown under conditions selected to increase cell cycling.

In one embodiment, the reprogramming methods of the present technology are applied to a single primary human fibroblast cell individually plated in the absence of feeder cells. In one embodiment, reprogramming occurs in greater than 15% of individually plated cells. In one embodiment, reprogramming occurs in greater than 50% of individually plated cells. In one embodiment, reprogramming occurs in greater than 90% of individually plated cells.

In one aspect a combined method of editing a cell and reprogramming the cell to a pluripotent state is provided. In one embodiment, the method comprises administering to the cell a Cas9 and a short guide RNA (gRNA), wherein the Cas9 generates a double stranded break (DSB) in a target nucleotide sequence in the genome of the cell, wherein the gRNA comprises a nucleotide sequence that is complementary to the target nucleotide sequence, and wherein the target nucleotide sequence is edited. In one embodiment, administered to the cell, seeded at a density of less than about 300 cells/cm$^2$ in the absence of feeder cells, is a composition comprising a complexation buffer and a reprogramming RNA cocktail, wherein the cell is reprogrammed to a pluripotent state.

Another aspect includes a method of generating a gene-corrected, patient-specific induced pluripotent stem cell (iPSC). In certain embodiments, the method comprises administering to a cell from a patient a Cas9 and a short guide RNA (gRNA). In other embodiments, the Cas9 generates a double stranded break (DSB) in a mutated target nucleotide sequence in the genome of the cell. In yet other embodiments, the gRNA comprises a nucleotide sequence that is complementary to the mutated target nucleotide sequence, and wherein the mutated target nucleotide sequence is edited. In yet other embodiments, a composition comprising a complexation buffer and a reprogramming RNA cocktail is administered to the cell, which is seeded at a density of less than about 300 cells/cm$^2$ in the absence of feeder cells, wherein the cell is reprogrammed into a gene-corrected, patient-specific induced pluripotent stem cell (iPSC).

Yet another aspect provided is a method of treating a condition in a patient in need thereof. In one embodiment, the method comprises administering to the patient a differentiated somatic cell derived from a gene-corrected iPSC, wherein the iPSC has been edited and reprogrammed by a method comprising: a.) administering to a cell a Cas9 and a short guide RNA (gRNA), wherein the Cas9 generates a double stranded break (DSB) in a mutated target gene in the cell, wherein the gRNA comprises a nucleotide sequence that is complementary to the mutated target gene, wherein the mutated target gene is replaced with the corrected target gene in the cell, and b.) administering to the cell, seeded at a density of less than about 300 cells/cm$^2$ in the absence of feeder cells, with a composition comprising a complexation buffer and a reprogramming RNA cocktail, wherein the cell is gene-corrected and reprogrammed into an iPSC. In one embodiment, the gene-corrected iPSC is differentiated into a somatic tissue-specific cell. In one embodiment, the iPSC is differentiated into an adult cell type suitable for transplantation into a particular organ. In certain embodiments, a gene corrected iPSC is differentiated into a keratinocyte (epidermal stem cell) that is then grown as an epidermal sheet and administered/transplanted to a patient. In certain embodiments, a neural tissue cell is obtained from a patient, corrected and reprogrammed into an iPSC, differentiated into a neuron, and administered/transplanted to a patient.

In certain embodiments of the methods, in step a.) the cell is further administered a single-stranded donor oligonucleotide (ssODN), wherein the ssODN comprises a nucleotide sequence that is homologous to the 5' end of the DSB, a nucleotide sequence that is homologous to the 3' end of the DSB, a nucleotide sequence comprising a corrected target gene, and a nucleotide sequence with a single nucleotide polymorphism (SNP) that disrupts the PAM sequence. In certain embodiments of the methods, in step a.) the cell is further administered a homologous DNA template. Examples of homologous DNA templates include but are not limited to double stranded DNA, adeno associated virus, and ssODN.

In one embodiment, the target nucleotide sequence is a mutated sequences. In one embodiment, the target nucleotide sequence is a wild-type sequence. In one embodiment, the editing of the target nucleotide sequence comprises a substitution, an insertion, a deletion, a rearrangement, or a frameshift of the nucleotide sequence.

In one embodiment, the cell is a fibroblast. In one embodiment, the cell is a primary cell.

In certain embodiments, the condition is selected from the group consisting of recessive dystrophic epidermolysis bullosa (RDEB), junctional epidermolysis bullosa (JEB), and Epidermolysis Bullosa Simplex Dowling-Meara type (EBS-DM), autism, Down Syndrome, mental retardation, brain development, microcephaly, inflammatory skin and bowel diseases, epilepsy, Pitt-hopkins-like Syndrome 2, schizophrenia, mental retardation, myoconic-atonic epilepsy, epidermolytic hyperkeratosis, ichthyosis, junctional epidermolysis bullosa, amelogenesis imperfecta, acute myeloid leukemia, thrombocytopenia, lupus, methylmalonic acidemia and homocysteinemia (cblX type), epilepsy, and mental retardation.

In one embodiment, the mutated target is the type VII collagen gene, COL7A1. In one embodiment, the mutated target is the Keratin (K) 14 gene (K14). In one embodiment, the mutated target is the DYRK1A locus. In one embodiment, the gRNA is complementary to the COL7A1$^{C7485+5G>A}$ mutation. In one embodiment, the gRNA is complementary to the dominant heterozygous K14$^{c373C>T}$ mutation. In one embodiment, correction is bi-allelic.

In one embodiment, the Cas9 is an mRNA. In one embodiment, the Cas9 comprises a T7 mRNA expression vector comprising a Cas9 ORF nucleotide sequence, a 3' UTR human beta globin nucleotide sequence, and a poly(A) tail sequence In one embodiment, the cell does not undergo a selection after the mutated target nucleotide sequence is edited. In one embodiment, the administering comprises transfecting the cell. In certain embodiments, the transfecting is performed at least 3 times, every other day, or every third day.

In certain embodiments, the gene editing efficiency is at least 20%, at least 60%, or at least 80%. In one embodiment, the reprogrammed cell is current Good Manufacturing Practice (cGMP) compatible.

BRIEF DESCRIPTION OF THE DRAWINGS

FIG. 16A is an H&E image at 40× magnification showing the intersection of the graft of human and mouse skin (the black arrow). FIG. 16B is immunofluorescence images of sections stained for epidermal-specific keratins (K14-red; K1-green). FIG. 16B upper panel (40× magnification) shows the results of immunostaining using antibodies to both mouse and human K14 and to only mouse K1. The area to the right of the white arrow where there is no staining with antibody to mouse K1 shows the human xenograft area. FIG. 16B lower panel (100× magnification) shows immunostaining using antibodies to only human K14 and human K1 of the portion of FIG. 16B upper panel indicated by the white box.

FIG. 17A is the series of micrographs taken with a 10× objective (100× magnification) showing the efficiency of transfection of modified mRNA encoding eGFP, the K14 TALENs and ssODNs in EBS iPSCs (IEB1-2 clone). FIG. 17B shows a schematic of the strategy to silence the mutant K14 allele using TALEN-mediated deletion of Exon 1 facilitated by specifically designed ssODNs.

FIG. 18 illustrates development of a Cas9 mRNA expression plasmid.

FIG. 19 is a schematic of the transfection timeline for the combined gene editing and reprogramming approach.

FIG. 24A shows Puro$^R$ modified mRNA was co-transfected with Cas9 modified mRNA and the following day, the transfected cells were treated with different concentrations of puromycin (0, 1, or 3 μg/ml) for 24 hours to look for increased Cas9 editing efficiency. FIG. 24B shows results of the T7 Endonuclease assay quantified using densitometry.

FIG. 24A is a schematic illustrating the tested time points Cas9/gRNA was added during the transfection. Cas9 was transfected either before, after the third, or after both the third and fourth reprogramming transfections. FIG. 25B illustrates resulting reprogrammed cells were collected after day 15 of reprogramming and tested for editing efficiency using a T7 Endonuclease assay.

FIGS. 27A-27B illustrate combined gene editing and reprogramming of RDEB patient derived fibroblasts. FIG. 27A summarizes the correction strategy of COL7A1. FIG. 27B shows results from patient fibroblasts corrected and reprogrammed as described. Resulting colonies were clonally expanded and genetic modifications confirmed by Sanger sequencing.

FIGS. 28A-28C illustrate a strategy for simultaneous correction of COL7A1$^{c.7485+5G>A}$ and cellular reprogramming. FIG. 28A shows COL7A1$^{c.7485\pm5G>A}$ correction strategy. The RDEB-associated mutation is indicated in red, and gRNA is in blue. The cut site is shown with scissors. Mutations introduced with ssODN are indicated in green, which includes a silent SNP to disrupt a PAM sequence. FIG. 28B shows a schematic of transfection timings to achieve simultaneous gene correction and reprogramming, RDEB fibroblasts were transfected with Cas9+gRNA+ssODN before the reprogramming to iPSCs. FIG. 28C shows the robust modification of the COL7A1 locus in cells harvested following reprogramming assessed using a T7 endonuclease assay.

FIG. 30A shows out of analyzed 49 iPSC clones picked from the experiment described in FIGS. 28A-28C, one clone had both mutant alleles corrected (top), and one had only one allele corrected (bottom). FIGS. 30B-30C show ddPCR analysis using probes specific either to COL7A1WT (blue) or COL7A1$^{c.7485+5G>A}$ (green). Panels in FIG. 30B show the ddPCR analysis performed with genomic DNA isolated from unmodified COL7A1WT (left) and COL7A1$^{c.7485+5G>A}$ (right) fibroblasts as a control for ddPCR probes. Panels in FIG. 30C show the ddPCR analysis of the two clones from FIG. 30A confirming genetic correction.

FIG. 31A shows the mutation was corrected by disrupting expression of the mutant allele by introducing a frame-shift mutation resulting from the treatment with Cas9. FIG. 31B shows Sanger sequencing results from two clonally expanded iPSC lines. iPSC colony #1 is unmodified. iPSC colony #2 has a frame-shift mutation on the mutant allele of K14. Both lines are genetically clonal.

DETAILED DESCRIPTION

Figure 1:
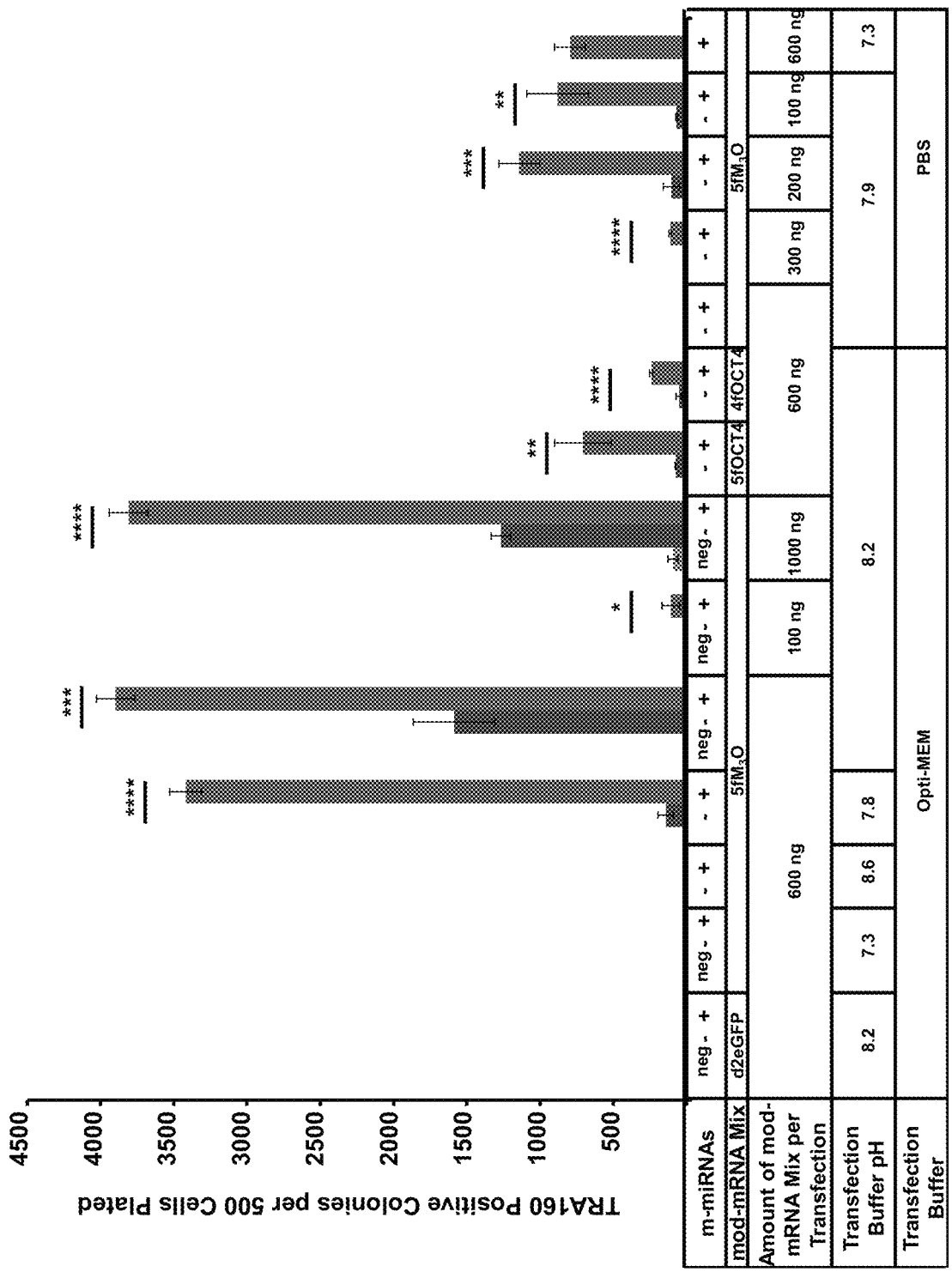
FIG. 1 is a chart showing the number of Tra-1-60$^+$ colonies generated per 500 primary human neonatal fibroblast cells transfected in different OPTI-MEM® and PBS buffer pH conditions, with differing amounts of modified mRNA (mod-mRNA) reprogramming cocktail, and in the presence and absence of microRNA mimics (m-miRNAs).

Disclosed herein are methods and compositions related to the integration-free and feeder cell-free reprogramming of cells (e.g., primary human fibroblasts), seeded at a low density (e.g., less than about 1000 cells/cm$^2$), to pluripotency using a modified mRNA-based approach. In one aspect, the methods and compositions of the present technology comprise the use of modified mRNA (mod-mRNA)

in combination with microRNA mimics (m-miRNAs). In addition to allowing for a low initial primary human fibroblast cell density of less than about 1000 cells/cm$^2$, the methods of the present technology yield an unprecedented reprogramming efficiency and produce clinically relevant iPSC lines from a variety of human primary fibroblast cells, including individually plated single cells.

In practicing the present technology, many conventional techniques in molecular biology, protein biochemistry, cell biology, immunology, microbiology, and recombinant DNA are used. These techniques are well-known and are explained in, e.g., *Current Protocols in Molecular Biology*, Vols. I-III, Ansubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively. Methods to detect and measure levels of polypeptide gene expression products (i.e., gene translation level) are well-known in the art and include the use polypeptide detection methods such as antibody detection and quantification techniques. (See also, Strachan & Read, *Human Molecular Genetics*, Second Edition. (John Wiley and Sons, Inc., NY, 1999)).

Definitions

The following terms are used herein, the definitions of which are provided for guidance.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the technology. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the term "cell density" refers to the density of cells on a given substrate, plate, well, dish, container, or the like, in which the cells are grown/seeded. Containers in which cells may include, but are not limited to, tissue culture plates, tissue culture dishes, and tissue culture wells, including tissue culture wells of various sizes, such as, 384-well, 96-well, 48-well, 24-well, 12-well, 6-well, and 100 mm dishes. In some embodiments, cell density may be expressed as the number of cells per plate, dish, well, and the like.

As used herein, the term "complexation buffer" refers to a buffer, including OPTI-MEM® or PBS, to which a transfection reagent and a molecule to be transfected are added and in which the transfection reagent associates or complexes with the molecule to be transfected.

As used herein, the terms "complexes with," "complexed with," and "complexed to" are used interchangeably, and refer to any method by which a nucleic acid molecule interacts with (e.g. binds to, comes into contact with, adheres to) a cationic lipid. Such an interaction can include, but is not limited to encapsulation of a nucleic acid molecule into a cationic liposome, association of a nucleic acid molecule and cationic lipid characterized by non-covalent, ionic charge interactions, and other types of associations between nucleic acid molecules and cationic lipids known by those skilled in the art.

The term "CRISPR/Cas" or "clustered regularly interspaced short palindromic repeats" or "CRISPR" refers to DNA loci containing short repetitions of base sequences followed by short segments of spacer DNA from previous exposures to a virus or plasmid. Bacteria and archaea have evolved adaptive immune defenses termed CRISPR/CRISPR-associated (Cas) systems that use short RNA to direct degradation of foreign nucleic acids. In bacteria, the CRISPR system provides acquired immunity against invading foreign DNA via RNA-guided DNA cleavage.

The "CRISPR/Cas9" system or "CRISPR/Cas9-mediated gene editing" refers to a type II CRISPR/Cas system that has been modified for genome editing/engineering. It is typically comprised of a "guide" RNA (gRNA) and a non-specific CRISPR-associated endonuclease (Cas9). "Guide RNA (gRNA)" is used interchangeably herein with "short guide RNA (sgRNA)" or "single guide RNA (sgRNA). The sgRNA is a short synthetic RNA composed of a "scaffold" sequence necessary for Cas9-binding and a user-defined ~20 nucleotide "spacer" or "targeting" sequence which defines the genomic target to be modified. The genomic target of Cas9 can be changed by changing the targeting sequence present in the sgRNA.

"Good manufacturing practices (GMP)" are the practices required in order to conform to the guidelines recommended by agencies that control the authorization and licensing of the manufacture and sale of food and beverages, cosmetics, pharmaceutical products, dietary supplements, and medical devices. These guidelines provide minimum requirements that a manufacturer must meet to assure that their products are consistently high in quality, from batch to batch, for their intended use. The rules that govern each industry may differ significantly; however, the main purpose of GMP is always to prevent harm from occurring to the end user. Additional tenets include ensuring the end product is free from contamination, that it is consistent in its manufacture, that its manufacture has been well documented, that personnel are well trained, and the product has been checked for quality more than just at the end phase. "Current Good Manufacturing Practice (cGMP) compatible" refers to a composition that is compatible with/complies with good manufacturing practice.

As used herein, the term "differentiates" or "differentiated" refers to a cell that takes on a more committed ("differentiated") position within a given cell lineage. "Dedifferentiated" refers to a cell that reverts to a less committed position within a cell lineage.

As used herein, the term "effective amount" refers to a quantity of a composition, compound, nucleic acid, or a number of cells sufficient to achieve a desired therapeutic and/or prophylactic effect, e.g., an amount which results in the prevention of, or amelioration of a disease or medical condition or one or more symptoms associated with a disease or medical condition or an amount which results in reprogramming of somatic cells. In the context of therapeutic or prophylactic applications, the amount of a composition, compound, nucleic acid, or a number of cells administered to the subject will depend on the composition, compound, nucleic acid, or type of cell, the type and severity of the disease, and on the characteristics of the individual, such as general health, age, sex, body weight and tolerance to drugs. It will also depend on the degree, severity and type of disease. The skilled artisan will be able to determine appropriate dosages depending on these and other factors.

As used herein, the term "feeder cells" refers to cells of one type that are co-cultured with cells of another type, to provide an environment in which the cells of the second type can grow. Feeder cells include, but are not limited to 3001 G irradiated neonatal human foreskin fibroblasts (GloabalStem) and FibroGRO mitomycin C-inactivated xeno-free human neonatal fibroblasts (Millipore).

As used herein, the term "induced pluripotent stem cells" (iPSCs) has a meaning well-known in the art and refers to cells having properties similar to those of embryonic stem cells (ESCs) and encompasses undifferentiated cells artificially derived by reprogramming differentiated, non-pluripotent cells, typically adult somatic cells.

As used herein, the term "isolated" means that materials naturally accompanying in normal circumstances are at least reduced, or preferably substantially completely eliminated. Therefore, the term "isolated cell" refers to a cell substantially free from other accompanying in natural circumstances substances (e.g., other cells, proteins, nucleic acids, etc.). The term "isolated" in relation to nucleic acids or polypeptides means that, for example, the nucleic acids or the polypeptides are substantially free from cellular substances or culture media when they are produced by recombinant DNA techniques; or precursory chemical substances or other chemical substances when they are chemically synthesized. Isolated nucleic acids are typically free from sequences naturally flanking the nucleic acid within an organism from which the nucleic acid is derived (i.e., sequences positioned at the 5' terminus and the 3' terminus of the nucleic acid).

As used herein, the term "microRNA" (also referred to as miRNA or miR) refers to small RNA molecules (about 19-27 nucleotides) that regulate gene expression by targeting one or more mRNAs for translational repression or cleavage. They are small inhibitory RNAs capable of suppressing the translation of target genes with high complementarity. Certain miRNA clusters, including miR-302-367, can promote reprogramming into induced pluripotent stem cells (iPSCs). By way of example, but not by way of limitation, reprogramming microRNAs include, but are not limited to miR200s, miR290s, miR371s, miR302s, miR367, miR369s, and biologically active fragments, analogues, and variants thereof. Unless otherwise indicated, the term "microRNA" includes microRNA mimics (m-miRNAs). Mature microRNA may include microRNA that has been cleaved from a microRNA precursor (pre-miRNA), or that has been synthesized. MicroRNA mimics are chemically modified RNA molecules designed to mimic endogenous mature microRNAs.

As used herein, the term "pluripotent stem cell" (PSC) refers to a cell capable of continued self-renewal, and, under appropriate conditions, of producing progeny of several different cell types. PSCs are capable of producing progeny that are derivatives of each of the three germ layers: endoderm, mesoderm, and ectoderm, according to a standard art-accepted test, such as the ability to form a teratoma in a suitable host, or the ability to differentiate into cells stainable for markers representing tissue types of all three germ layers in culture. Included in the definition of PSCs are embryonic cells of various types, such as embryonic stem cells (ESCs), as well as induced pluripotent stem cells (iPSCs) that have been reprogrammed from an adult somatic cell.

Those skilled in the art will appreciate that except where explicitly required otherwise, PSCs include primary tissue and established lines that bear phenotypic characteristics of PSCs, and derivatives of such lines that still have the capacity of producing progeny of each of the three germ layers. PSC cultures are described as "undifferentiated" or "substantially undifferentiated" when a substantial proportion of stem cells and their derivatives in the population display morphological characteristics of undifferentiated cells, clearly distinguishing them from differentiated cells of embryo or adult origin. Undifferentiated PSCs are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighboring cells that are differentiated.

As used herein, "prevention" or "preventing" of a disease or medical condition refers to the reduction of the occurrence of a disease or medical condition in a treated sample relative to an untreated control sample, or a delay in the onset of one or more symptoms of the disease or medical condition relative to the untreated control sample.

As used herein, the term "reprogramming" and grammatical equivalents refer to a process that alters or reverses the differentiation status of a somatic cell that is either partially or terminally differentiated. Reprogramming of a somatic cell may be a partial or complete reversion of the differentiation status of the somatic cell. In some embodiments, reprogramming is complete when a somatic cell is reprogrammed into an induced pluripotent stem cell. However, reprogramming may be partial, such as reversion into any less differentiated state. For example, reverting a terminally differentiated cell into a cell of a less differentiated state, such as a multipotent cell.

As used herein, "reprogramming efficiency" refers to the number of iPSC colonies generated per somatic input cell. For example, reprogramming efficiency can be calculated by dividing the average number of Tra-1-60$^+$ colonies per well on a multi-well plate by the initial number of cells plated. Tra-1-60 is a pluripotent stem cell-specific protein expressed on the surface of undifferentiated embryonic and induced pluripotent stem cells.

As used herein, the term "reprogramming factor" refers to a molecule, which when contacted with a cell (e.g., expressed by a cell, transformed into a cell for expression, exogenously provided to a cell, etc.), can, either alone or in combination with other molecules, cause reprogramming. By way of example, but not by way of limitation, reprogramming factors include, but are not limited to Oct3 protein, Oct4 protein, Myo-D-Oct4 ($M_3O$) protein, Sox1 protein, Sox2 protein, Sox3 protein, Sox15 protein, Klf1, protein, Klf2 protein, Klf3 protein, Klf4 protein, Klf5 protein, c-Myc protein, L-Myc protein, N-Myc protein, Nanog protein, Lin28A protein, Tert protein, Utf1 protein, Aicda protein, Glis1, Sall4, Esrrb, Tet1, Tet2, Zfp42, Prdm14, Nr5a2, Gata6, Sox7, Pax1, Gata4, Gata3, cEBPa, HNF4a, GMNN, SNAIL, Grb2, Trim71, and biologically active fragments, analogues, variants, and family members thereof.

As used herein, the term "reprogramming mRNA cocktail" refers to a composition including one or more mRNAs that encode one or more proteins that may enhance the efficiency of iPSC generation. By way of example, but not by way of limitation, in some embodiments, the reprogramming mRNA cocktail comprises reprogramming mRNAs e.g., RNAs encoding one or more of Oct3 protein, Oct4 protein, Myo-D-Oct4 ($M_3O$) protein, Sox1 protein, Sox2 protein, Sox3 protein, Sox15 protein, Klf1, protein, Klf2 protein, Klf3 protein, Klf4 protein, Klf5 protein, c-Myc protein, L-Myc protein, N-Myc protein, Nanog protein, Lin28A protein, Tert protein, Utf1 protein, Aicda protein, Glis1, Sall4, Esrrb, Tet1, Tet2, Zfp42, Prdm14, Nr5a2, Gata6, Sox7, Pax1, Gata4, Gata3, cEBPa, HNF4a, GMNN, SNAIL, Grb2, Trim71, and biologically active fragments, analogues, variants, and family members thereof. In some embodiments, the reprogramming mRNA cocktail comprises mRNAs encoding reprogramming factors Oct4 protein or Myo-D-Oct4 ($M_3O$) protein, Sox2 protein, and Klf4 protein in a 3:1:1 molar ratio. In some embodiments, the reprogramming mRNA cocktail comprises mRNAs encoding reprogramming factors Oct4 protein or Myo-D-Oct4 ($M_3O$) protein, Sox2 protein, and Klf4 protein in a 2:1:1 molar ratio. In some embodiments, the reprogramming mRNA cocktail comprises mRNAs encoding reprogramming factors Oct4 protein or Myo-D-Oct4 ($M_3O$) protein, Sox2 protein, and Klf4 protein in a 1:1:1 molar ratio. In some embodiments, the reprogramming mRNA cocktail comprises mRNAs encoding Oct4 protein or Myo-D-Oct4 ($M_3O$) protein, Sox2 protein, Klf4 protein, c-Myc protein, Lin28A protein, and Nanog protein in a 3:1:1:1:1:1 molar ratio with Sox2 and Klf4. In some embodiments, the reprogramming mRNA cocktail comprises mRNAs encoding Oct4 protein or Myo-D-Oct4 ($M_3O$) protein, Sox2 protein, Klf4 protein, c-Myc protein, Lin28A protein, and Nanog protein in a 2:1:1:1:1:1 molar ratio with Sox2 and Klf4. In some embodiments, the reprogramming mRNA cocktail comprises mRNAs encoding Oct4 protein or Myo-D-Oct4 ($M_3O$) protein, Sox2 protein, Klf4 protein, c-Myc protein, Lin28A protein, and Nanog protein in a 1:1:1:1:1:1 molar ratio with Sox2 and Klf4. In some embodiments, mRNAs encoding Oct4 or Myo-D-Oct4 ($M_3O$) are replaced with mRNAs encoding Utf1 or Gata4.

In some embodiments, the reprogramming mRNA cocktail comprises a mixture of modified mRNAs incorporating modified ribonucleoside bases comprising pseudouridine (w) and/or 5-methylcytidine ($m^5C$) residues, wherein the modified mRNAs encode for one or more of Oct3 protein, Oct4 protein, Myo-D-Oct4 ($M_3O$) protein, Sox1 protein, Sox2 protein, Sox3 protein, Sox15 protein, Klf1, protein, Klf2 protein, Klf3 protein, Klf4 protein, Klf5 protein, c-Myc protein, L-Myc protein, N-Myc protein, Nanog protein, Lin28A protein, Tert protein, Utf1 protein, Aicda protein, Glis1, Sall4, Esrrb, Tet1, Tet2, Zfp42, Prdm14, Nr5a2, Gata6, Sox7, Pax1, Gata4, Gata3, cEBPa, HNF4a, GMNN, SNAIL, Grb2, Trim71, and biologically active fragments, analogues, variants, and family members thereof.

In some embodiments, the reprogramming mRNA cocktail comprises a mixture of modified mRNAs incorporating modified ribonucleoside bases comprising a pseudouridine (w) or a modified nucleoside, wherein the modified nucleoside is 5-methylcytidine ($m^5C$), 5-methyluridine ($m^5U$), N6-methyladenosine ($m^6A$), inosine and 2'-O-methylated nucleosides, in addition to N7-methylguanosine ($m^7G$), 2-thiouridine ($s^2U$), pseudouridine (w), or 2'-O-methyl-U.

In some embodiments, the modified nucleoside is $m^1A$ (1-methyladenosine); $m^2A$ (2-methyladenosine); Am (2'-O-methyladenosine); $ms^2$ $m^6A$ (2-methylthio-$N^6$-methyladenosine); $i^6A$ ($N^6$-isopentenyladenosine); $ms^2i^6A$ (2-methylthio-$N^6$isopentenyladenosine); $io^6A$ ($N^6$-(cis-hydroxyisopentenyl)adenosine); $ms^2io^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$ ($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$($N^4$-acetylcytidine); $f^5C$ (5-formylcytidine); $m^5$ Cm (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2_2G$ ($N^2,N^2$-dimethylguanosine); $m^2Gm$ ($N^2$,2'-O-dimethylguanosine); $m^2_2Gm$ ($N^2,N^2$,2'-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5s^2U$ (5-aminomethyl-2-thiouridine); $mnm^5U$ (5-methylaminomethyluridine); $mnm^5s^2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s^2U$ (5-carboxymethylaminomethyl-2-thiouridine); $m^6_2A$ ($N^6,N^6$-dimethyladenosine); Im (2'-O-methylinosine); $m^4C$($N^4$-methylcytidine); $m^4$ Cm ($N^4$,2'-O-dimethylcytidine); $hm^5C$ (5-hydroxymethylcytidine); $m^3U$ (3-methyluridine); $cm^5U$ (5-carboxymethyluridine); $m^6Am$ ($N^6$,2'-O-dimethyladenosine); $m^6_2Am$ ($N^6,N^6$,O-2'-trimethyladenosine); $m^{2,7}G$ ($N^2$,7-dimethylguanosine); $m^{2,2,7}G$ ($N^2,N^2$,7-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $\tau m^5U$ (5-taurinomethyluridine); $\tau m^5s^2U$ (5-taurinomethyl-2-thiouridine)); imG-14 (4-demethylwyosine); imG2 (isowyosine); or $ac^6A$ ($N^6$-acetyladenosine).

As used herein, the term "somatic cell" refers to any cell other than pluripotent stem cells or germ cells. In some embodiments, the cells may be any type of somatic cells, of any origin, including cells derived from humans or animals. By way of example, but not by way of limitation, somatic cells may include, but are not limited to fibroblast cells, epithelial cells, osteocytes, chondrocytes, neurons, muscle cells, hepatic cells, intestinal cells, spleen cells, and adult stem cells, including, but not limited to hematopoietic stem cells, vascular endothelial stem cells, cardiac stem cells, muscle-derived stem cells, mesenchymal stem cells, epidermal stem cells, adipose-derived stem cells, intestinal stem cells, neural stem cells, renal epithelium cells, urothelial cells, and hepatic stem cells.

As used herein, a "synergistic effect" refers to a greater-than-additive effect that is produced by a combination of at least two agents, and which exceeds that which would otherwise result from the individual administration of the agents.

As used herein, "target nucleotide sequence" or "target sequence" refers to a nucleic acid sequence that defines a portion of a nucleic acid to which a binding molecule may specifically bind under conditions sufficient for binding to occur. The target nucleotide sequence can be a mutated sequence or a wild-type sequence.

As used herein the term "transfection" refers to the delivery of exogenous nucleic acid molecules to a cell, either in vivo or in vitro, whereby the nucleic acid is taken up by the cell and is functional within the cell. A cell that has taken up the exogenous nucleic acid is referred to as a "host cell" or "transfected cell."

As used herein, the term "transfection reagent" refers to a substance or mixture of substances that associates with a molecule and facilitates the delivery of the molecule to and/or internalization of the molecule by a cell. By way of example, but not by way of limitation, transfection reagents include cationic polymers, cationic lipids, or cell-penetrating peptides.

"Treating" or "treatment" as used herein covers the treatment of a disease or medical condition described herein, in a subject, such as a human, an animal, or a mammal, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or medical condition.

Cellular Reprogramming

General

The induction of pluripotency by enforced expression of four transcription factors (Klf4, c-Myc, Oct4, and Sox2) through the use of retroviral vectors in mouse and human fibroblasts was first described by Yamanaka and colleagues (*Cell* 131: 861-872 (2007); *Cell* 126:663-676 (2006)). However, the risk of integration of viral sequences into the host cell genome precludes the therapeutic application of retrovirally derived iPSCs in patients. To address this obstacle, a number of nonintegrating methods for iPSC derivation including the use of adenoviral vectors, nonintegrating DNA plasmid-based vectors, direct protein transduction, Sendai viral vectors, and modified mRNA-based approaches were developed (See Mandal, et al. *Nature Protocols* 8(3):568-582 (2013)). Delivery of mRNA into mammalian cells can be accomplished by complexing the RNA with a cationic vehicle, such as a lipid, to facilitate uptake by endocytosis. However, studies have shown that transfection of RNA into mammalian cells resulted in severe cytotoxicity due to the activation of innate antiviral defenses. To reduce the immunogenic profile of synthetic RNA, researchers developed synthetic, capped modified mRNAs substituting cytidine and uridine with the modified nucleosides pseudouridine and 5-methylcytidine, and demonstrated that modified mRNAs encoding reprogramming factors (e.g., Oct4, Sox2, c-Myc, Klf4, and Lin28A) reprogrammed human fibroblasts to pluripotency. (Warren, et al. *Cell Stem Cell* 7:618-630 (2010)).

Despite advances in developing reprogramming methods and nonintegrative methodologies for iPSC derivation, the potential application of iPSC technology in clinical and research settings is hampered by the relatively low efficiency of iPSC generation, the high costs associated with therapeutically relevant reprogramming protocols, the amount of time required to establish a cell line form a patient biopsy before iPSC generation can be initiated, and challenges associated with reprogramming a relatively low number of somatic cells with integration-free approaches. In addition, although modified mRNA (mod-mRNA) methods have been shown to reprogram established fibroblast cell lines, the application of mod-mRNA-based methods to primary cell lines derived from a patient has produced inconsistent results.

Figure 5:
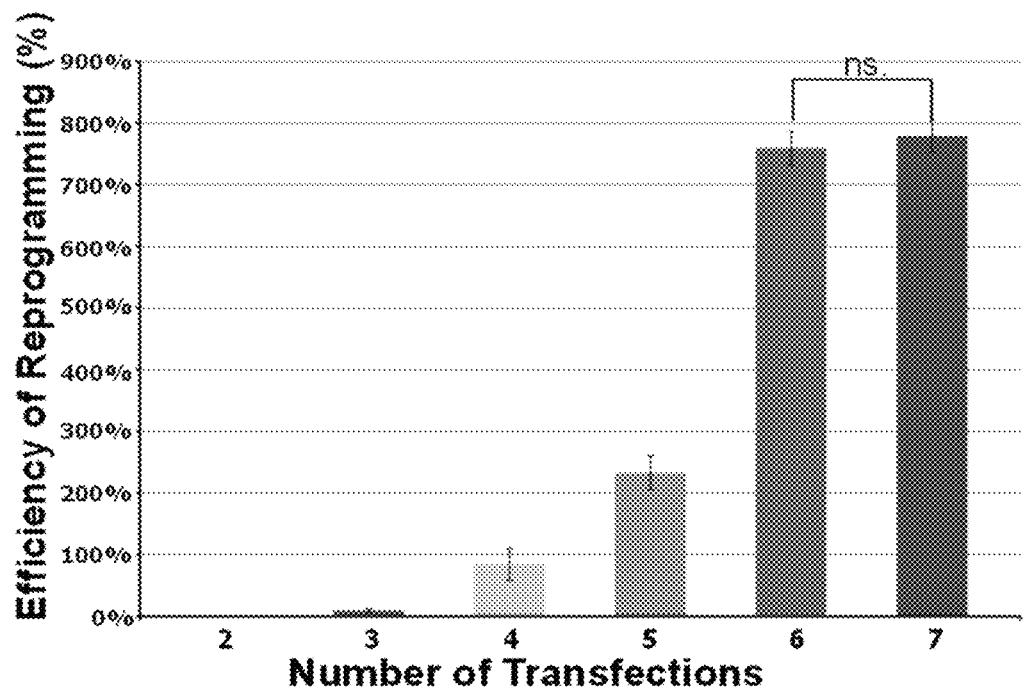
FIG. 5 is a chart showing the reprogramming efficiency as a function of the number of transfections. Reprogramming efficiency is calculated as the number of generated Tra-1-60 positive colonies divided by the number of starting cells (500 in this particular experiment) and multiplied by 100%.

In contrast to known methods, the feeder-free combinatorial mod-mRNA/m-miRNA reprogramming methods of the present technology allow for the successful reprogramming of low density primary human fibroblast cultures, starting from as little as a single cell, into clinically relevant, genome unmodified iPSCs at an unprecedented efficiency. For example, as shown in FIG. 1, the application of the methods of the present technology to primary neonatal fibroblasts resulted in the production of over 4,000 Tra-1-60$^+$ iPSC colonies from only 500 starting cells in a 6-well dish format in 18 days after as few as 7 transfections. Over 60 Tra-1-60$^+$ iPSC colonies are produced from only 500 starting cells in 18 days after as few as 3 transfections (FIG. 5). The ability to reprogram cells using a low starting cell density may be particularly advantageous in the clinical setting. Lower input cell density will shorten the time between patient biopsy and iPSC generation and will reduce the risk of contamination and the accumulation of mutations due to extensive cell culturing. In addition, the reduced number of RNA transfections required for our protocol significantly reduces the cost of reprogramming for both research and clinical applications as compared to other RNA-based reprogramming protocols.

The methods disclosed herein are also useful to reprogram individually plated single human primary fibroblasts on a feeder-free system. As shown in Table 1, the methods of the present technology reprogram greater than 90% of individually plated primary human neonatal fibroblasts. By contrast, recent reports have demonstrated that the reprogramming efficiency of human iPSCs is approximately 2.1% for known mRNA methods using a starting cell density of 50,000 cells. (Schlaeger, et al. *Nature Biotechnology* 33:58-63 (2015)). In addition, the combination of mod-mRNA cocktail and m-miRNAs in the methods disclosed herein produces a synergistic effect on reprogramming efficiency as shown in FIG. 1 and Table 1.

TABLE 1

| Primary Neonatal Cell Line | microRNA mimics | Wells with an individually plated single cell | Wells with dividing cells throughout reprogramming | Wells with Tra-1-60$^+$ colonies | Reprogramming efficiency (%) Wells with Tra-1-60$^+$ colonies/wells with dividing cells × 100% |
|---|---|---|---|---|---|
| FN1 | + | 157 | 144 | 106 | 73.6% |
|  | − | 134 | 116 | 0 | 0% |
| FN2 | + | 141 | 130 | 101 | 77.7% |
|  | − | 107 | 98 | 8 | 8.2% |

TABLE 1-continued

| Primary Neonatal Cell Line | microRNA mimics | Wells with an individually plated single cell | Wells with dividing cells throughout reprogramming | Wells with Tra-1-60+ colonies | Reprogramming efficiency (%) Wells with Tra-1-60+ colonies/wells with dividing cells × 100% |
|---|---|---|---|---|---|
| FN5 | + | 110 | 108 | 98 | 90.7% |
|  | − | 111 | 110 | 16 | 14.5% |

The methods disclosed herein are also useful to reprogram or dedifferentiate cells prior to re-differentiation. In some embodiments, the methods include generating differentiated cells by exposing pluripotent cells generated by the methods described herein to cell lineage differentiation factors. In some embodiments, the differentiated cells comprise neuronal lineage cells. In some embodiments, the differentiated cells comprise endodermal lineage cells. In some embodiments, the differentiated cells comprise cardiomyocyte lineage cells. In some embodiments, the differentiated cells comprise keratinocytes. In some embodiments, the differentiated cells comprise mesenchymal stem cells. In some embodiments, the mesenchymal stem cells are able to further differentiate to fibroblasts, chondrocytes and/or osteoblasts. In some embodiments, the differentiated cells comprise fibroblasts.

The methods disclosed herein can be used to generate iPSCs that can be further modulated to form any type of somatic cells by culturing the iPSCs under cell-type specific conditions known in the art. Cell-type or cell lineage specific conditions may include contacting the iPSCs with cell and cell lineage differentiation factors under conditions known in the art and described herein. Specifically, iPSCs can be differentiated toward a neuronal lineage by exposing them to one or more factors that include, but are not limited to, N2 and B27 supplements, Noggin, SB431542, DMEM/F12 medium, laminin, cyclic adenosine monophosphate (cAMP), ascorbic acid, brain-derived neurotrophic factor (BDNF), glial cell-derived neurotrophic factor (GDNF), insulin-like growth factor I (IGF-I), fibroblast growth factor (FGF)-8, transforming growth factor (TGF) beta 3 (TGF-β3), or retinoic acid. iPSCs can be differentiated toward an endodermal lineage (such as hepatocytes, pancreatic cells, intestinal epithelial, lung cells) by exposing them to specific differentiation factors and media, which include, but are not limited to, RPMI medium, SFD medium, N2/B27 medium, glutamine, monothioglycerol (MTG), CHIR 99021, activin A, ascorbic acid, bone morphogenetic protein (BMP)-4, vascular endothelial growth factor (VEGF), epidermal growth factor (EGF), basic FGF (bFGF), hepatocyte growth factor (HGF), dexamethasone, TGF-α, hydrocortisone, FGF-7, or Exendin-4. Cardiomyocyte lineage differentiation factors and media include, but are not limited to, StemPro medium, DMEM/F12 medium, BMP4, Activin A, bFGF, VEGF, Dickkopf-related protein 1 (DKK1), Transferrin, MTG, or ascorbic acid. For mesenchymal stem cell differentiation, iPSC can be exposed to fetal serum and differentiation factors which include, but are not limited to, bFGF, BMP-4, EGF, retinoic acid, or platelet derived growth factor (PDGF). iPSC-derived MSC can subsequently be differentiated toward (1) bone progenitors (osteocytes) through exposure to one or more factors such as ascorbic-acid-2-phosphate, β-glycerophosphate, M dexamethasone or BMP-2, (2) chondrogenic progenitor (chondrocytes) through exposure to one or more factors such as dexamethasone, ascorbic-acid-2-phosphate, proline, pyruvate, TGF-β3, or insulin/transferrin/selenious acid supplement (ITS) (3) adipogenic progenitors through exposure to one or more factors such as hydrocortisone, isobutylmethylxanthine or indomethacin; and (4) fibroblasts through exposure to connective tissue growth factor (CTGF). Fibroblasts can also be derived directly from iPSCs via exposure to one or more factors such as TGF-β2, ascorbic acid, connective tissue growth factor (CTGF), ITS reagents, or fetal serum. Keratinocyte lineage differentiation factors include, but are not limited to, BMP4, retinoic acid, ascorbic acid, insulin, hydrocortisone, bovine pituitary extract, IGF-1 or EGF.

The methods disclosed herein are also useful to reprogram or dedifferentiate cells prior to re-differentiation of cells and organ formation. In some embodiments, the methods include generating organs by exposing pluripotent cells generated by the methods described herein to differentiating factors as described herein and combining one or more of the differentiated cells and cell types under conditions sufficient to encourage organ formation. For example, iPSCs generated using the methods described herein can be differentiated to cells that can be used to make skin as well as other organs such as liver, bones, and cartilage. Such methods include combining one or more of the lineages and/or cell types that form an organ under conditions sufficient to encourage organ formation. Specifically, conditions sufficient to form skin may include but are not limited to co-culture or in vivo co-grafting of iPSC-derived keratinocytes and fibroblasts. For ex vivo generated skin equivalents, fibroblasts are grown on extracellular protein matrix (such as collagen, laminin, fibronectin, etc.) to form a dermis-like structure followed by overlaying with keratinocytes to produce epidermis. For an in vivo generation of human skin equivalents/grafting, a silicone grafting chamber can be surgically inserted onto the muscle fascia of recipient severe combined immunodeficiency (SCID) mice. A cell slurry consisting of keratinocytes and fibroblasts derived from human iPSCs is introduced into this chamber. The cells and factors necessary to generate human skin equivalents ex vivo and in vivo include, but are not limited to, iPSC derived keratinocytes, fibroblasts, melanocytes and derma papilla cells, EGF, insulin, fetal serum, ascorbic acid, hydrocortisone, bovine pituitary extract, IGF-1, or DMEM medium. Bones can be grown ex vivo by culturing iPSC-derived osteocytes in the presence of ascorbic-acid-2-phosphate, β-glycerophosphate and fetal serum. Cartilage can be generated by culturing iPSC-derived chondrocytes as micromasses in the presence of ITS, dexamethasone, ascorbic-acid-2-phosphate, proline, pyruvate and TGF-β3. Liver can be generated via the formation of liver buds. Conditions sufficient to form liver buds may include, but are not limited to, the combination of mesenchymal stem cells with hepatic progenitors (both can be derived from iPSCs as described above) in the presence of endothelial growth medium and/or hepatocyte culture medium supplemented with dexamethasone, oncostatin, HGF, and matrigel.

The methods disclosed herein can also be used to generate iPSCs that can be further genetically manipulated via homologous recombination or other appropriate techniques known in the art using, for example, TALENs, zinc-finger nucleases, or CRISPR/Cas9 systems with the goal to model a variety of genetic disorders as well as to generate isogenic wild-type controls when iPSCs are generated from patients with genetic defects. These genetically manipulated iPSC clones can be differentiated into relevant cell types for research studies or for therapeutic applications to be returned back to the patient as an autograft.

Sources of Cells for Reprogramming

The type and age of somatic cells that may be reprogrammed by the methods disclosed herein are not limiting, and any kind of somatic cells may be used. In some embodiments, mature somatic cells may be used. In some embodiments, somatic cells are from an embryonic stage. By way of example, but not by way of limitation, somatic cells may be primary cells (non-immortalized cells), such as those freshly isolated from an animal, or may be derived from a cell line (immortalized cells). In some embodiments, the somatic cells are mammalian cells, such as, for example, human cells or mouse cells. In some embodiments, the somatic cells are canine, feline, equine, or bovine cells. By way of example, but not by way of limitation, somatic cells may be obtained by well-known methods, from different organs, such as, but not limited to, skin, lung, pancreas, liver, stomach, intestine, heart, reproductive organs, bladder, kidney, urethra and other urinary organs, or generally from any organ or tissue containing living somatic cells, or from blood cells. In some embodiments of the methods disclosed herein, fibroblasts are used. In some embodiments of the methods disclosed herein, keratinocytes are used. In some embodiments of the methods disclosed herein, melanocytes are used. In some embodiments of the methods disclosed herein, cells isolated from the blood and/or bone marrow (which include, but are not limited to, endothelial cells, lymphocytes, myeloid cells, leukocytes, mesenchymal stem cells, and hematopoietic stem cells) are used. In some embodiments of the methods disclosed herein, mesenchymal stem cells are used. In some embodiments of the methods disclosed herein, urine-derived renal epithelium cells are used. The term somatic cell, as used herein, is also intended to include adult stem cells.

In some embodiments, cells are reprogrammed for an intended therapeutic use, and are derived from the patient subject. Somatic cells can be derived from a healthy or diseased subject, which include, but are not limited to, patients suffering from epidermolysis bullosa (EB), subtypes of skin blistering disorders such as EB simplex (EBS), junctional EB (JEB), dominant dystrophic EB (DDEB) and recessive dystrophic EB (RDEB), Kindler syndrome, acquired and congenital ichthyoses such as epidermolytic ichthyosis (EI), formerly known as epidermolytic hyperkeratosis (EHK), and Lamellar Ichthyosis (LI); Ectrodactyly, Ectodermal dysplasia, and Cleft lip/palate (EEC) syndrome; Dyskeratosis Congenita (DC); connective tissue diseases and injuries, type I diabetes, Down Syndrome, Danon disease.

Methods for obtaining human somatic cells are well-known in the art, e.g., as described in Schantz and Ng (2004), *A Manual for Primary Human Cell Culture*, World Scientific Publishing Co., Pte, Ltd. In some embodiments, methods for obtaining somatic cells include obtaining a cellular sample, e.g., by a biopsy (e.g., a skin sample).

Cell Density for Reprogramming

In some embodiments, somatic cells selected for reprogramming are plated at low density. In some embodiments, cells are plated at a density of about 10,000 cells/cm$^2$ or less. In some embodiments, cells are plated at a density of about 9,000 cells/cm$^2$ or less. In some embodiments, cells are plated at a density of about 8,000 cells/cm$^2$ or less. In some embodiments, cells are plated at a density of about 7,000 cells/cm$^2$ or less. In some embodiments, cells are plated at a density of about 6,000 cells/cm$^2$ or less. In some embodiments, cells are plated at a density of about 5,000 cells/cm$^2$ or less. In some embodiments, cells are plated at a density of about 4,000 cells/cm$^2$ or less. In some embodiments, cells are plated at a density of about 3,000 cells/cm$^2$ or less. In some embodiments, cells are plated at a density of about 2,000 cells/cm$^2$ or less. In some embodiments, cells are plated at a density of about 1,000 cells/cm$^2$ or less. In some embodiments, cells are plated at a density of about 900 cells/cm$^2$ or less. In some embodiments, cells are plated at a density of about 800 cells/cm$^2$ or less. In some embodiments, cells are plated at a density of about 700 cells/cm$^2$ or less. In some embodiments, cells are plated at a density of about 600 cells/cm$^2$ or less. In some embodiments, cells are plated at a density of about 500 cells/cm$^2$ or less. In some embodiments, cells are plated at a density of about 400 cells/cm$^2$ or less. In some embodiments, cells are plated at a density of about 300 cells/cm$^2$ or less. In some embodiments, cells are plated at a density of about 200 cells/cm$^2$ or less. In some embodiments, cells are plated at a density of about 100 cells/cm$^2$ or less. In some embodiments, cells are plated at a density of about 50 cells/cm$^2$ or less. In some embodiments, cells are plated at a density of about 25 cells/cm$^2$ or less. In some embodiments, cells are plated at a density of about 10 cells/cm$^2$ or less. In some embodiments, cells are plated at a density of about 5 cells/cm$^2$ or less. In some embodiments, cells are plated at a density of about 2 cells/cm$^2$ or less. In some embodiments, cells are plated at a density of about 1 cell/cm$^2$ or less. In some embodiments, cells are plated at a density of about 0.5 cells/cm$^2$ or less. In some embodiments, cells are plated at a density of about 0.25 cells/cm$^2$ or less. In some embodiments, low density is in the range of about 0.1-5,000 cells/cm$^2$. In some embodiments, low density is in the range of about 0.1-3,000 cells/cm$^2$. In some embodiments, low density is in the range of about 0.1-2,000 cells/cm$^2$. In some embodiments, low density is in the range of about 0.1-1,000 cells/cm$^2$. In some embodiments, the reprogrammed cells are single cell derived colonies.

Therapeutic Applications

The reprogrammed cells generated by the methods described herein have a variety of applications and therapeutic uses. In some embodiments, the methods disclosed herein are directed to reprogramming cells suitable for therapeutic applications, including transplantation into patients, as the iPSCs have been reprogrammed without providing exogenous DNA. In some embodiments, the methods of the present technology yield iPSCs that have not been exposed to animal-derived, human-derived, or allogeneic materials. In some embodiments, the methods disclosed herein yield reprogrammed cells with normal karyotypes or with karyotypes that are the same as the patient from whom they were derived. In some embodiments, uncorrected iPSCs from patients can be differentiated into cell types relevant to the genetic disorder for modeling the disease in organotypic cultures or for recapitulating the disease phenotype in vivo by transplanting onto immunodeficient mice as a xenograft. In another embodiment, a particular mutation of interest can be introduced into normal healthy iPSCs, as another approach to modeling a disorder. These in vitro and in vivo models may serve as platforms for yielding new insights into disease mechanisms and testing novel therapeutic strategies.

In some embodiments, therapeutic applications include, but are not limited to, autologous iPSC-derived bone and cartilage transplantation/repair for non-healing fractures, and the generation of autologous bioengineered skin equivalents from iPSCs for treating non-healing wounds, among others.

In some embodiments, a method for treating or preventing one or more symptoms of a disease or disorder in a subject, comprising dedifferentiating cells in vitro and administering a therapeutically effective amount of the dedifferentiated cells to a subject in need thereof is provided. In some embodiments, a method for treating or preventing one or more symptoms of a disease or disorder in a subject comprises reprogramming cells to pluripotency in vitro and administering a therapeutically effective amount of the reprogrammed cells to a subject in need thereof. The method comprises obtaining one or more somatic cells from a subject and reprogramming the cells into iPSCs or dedifferentiated cells.

In some embodiments, a method for treating or preventing one or more symptoms of a disease or disorder in a subject comprises reprogramming cells to pluripotency in vitro, differentiating the cells to one or more appropriate cell types, and administering a therapeutically effective amount of the differentiated cells to a subject in need thereof. The method comprises obtaining one or more somatic cells from a subject and reprogramming the cells into iPSCs or dedifferentiated cells. The cells are then cultured under conditions that allow for the cells to differentiate into a desired cell type suitable for treating or preventing a condition. The differentiated cells may then be introduced into the subject to treat or prevent the condition.

In some embodiments, a method for treating or preventing one or more symptoms of a disease or disorder in a subject comprising (a) reprogramming cells to pluripotency in vitro, (b) differentiating the cells to one or more appropriate cell types, (c) combining one or more differentiated cell types to form an organ, and (d) administering a therapeutically effective amount of the organ to a subject in need thereof is provided. The method comprises obtaining one or more somatic cells from a subject and reprogramming the cells into iPSCs or dedifferentiated cells. The cells are then cultured under conditions that allow for the cells to differentiate into a desired cell type suitable for treating or preventing a condition. The one or more differentiated cell types are combined under conditions that support formation of an organ. The differentiated organ may then be introduced into the subject to treat or prevent the condition.

In some embodiments, iPSCs generated using the methods described herein are genetically modified to correct a genetic abnormality or to improve or change cellular functioning. Methods of genetically modifying cells are well-known in the art, and described herein. In some embodiments, the genetic modification is performed prior to generation of the iPSCs, after generation of the iPSCs, prior to differentiation of the iPSCs, or after differentiation of the iPSCs. In some embodiments, a method of treating a patient suffering from a genetic abnormality comprises: (a) reprogramming one or more primary adult cells from the patient to a pluripotent state using any of the methods described herein to form iPSCs, (b) genetically correcting one or more mutations in the iPSCs (prior to generation of the iPSCs, after generation of the iPSCs, prior to differentiation of the iPSCs, or after differentiation of the iPSCs), (c) differentiating the iPSCs, (d) providing the corrected differentiated cells to the patient. In some embodiments, the primary adult cells are fibroblast cells. In some embodiments, the corrected iPSCs are differentiated to fibroblasts and keratinocytes. In some embodiments, the method further comprises generating skin from the differentiated cells. In some embodiments, the patient is suffering from one or more of genetic diseases such as Epidermolysis Bullosa simplex (EBS), recessive dystrophic EB (RDEB), junctional EB (JEB), or Epidermolytic Ichthyosis. In some embodiments, the one or more mutations includes K14, K1, collagen type VII, laminin332, collagen type XVII.

In some embodiments, generation of iPSCs allows for the development of cell or stem cell replacement strategies to treat genetic disorders, and for modeling these diseases with the goal of producing novel therapeutic options for patients. In this approach, cells are isolated from a patient with a genetic disorder. This can be accomplished by many means, for example through a skin biopsy, blood draw, or a bone marrow aspirate. Suitable cell types for reprogramming include keratinocytes, melanocytes, fibroblasts, mesenchymal stem cells, etc. The generated iPSCs are genetically corrected by, for example, homologous recombination or other appropriate techniques known in the art using, for example, TALENs, zinc-finger nucleases, or CRISPR/Cas9 systems. The corrected iPSC clones are differentiated into relevant cell types for transplantation (typically somatic cells) and returned back to the patient as an autograft.

In some embodiments, therapeutic applications of the present technology include but are not limited to skin repair, skin transplantation, cartilage repair, bone repair, neuron transplantation, hematopoietic stem cell transplantation, mesenchymal stem cell transplantation, tissue reconstruction, organ reconstruction, or beta cell transplantation in a subject in need thereof.

In some embodiments, the methods disclosed herein can be used to generate cells for the treatment and/or prevention of a variety of diseases or disorders, including, but not limited to, skin injuries (wounds) and diseases, including epidermolysis bullosa (EB), subtypes of skin blistering disorders such as EB simplex (EBS), junctional EB (JEB), dominant dystrophic EB (DDEB) and recessive dystrophic EB (RDEB), Kindler syndrome, acquired and congenital ichthyoses such as epidermolytic ichthyosis (EI), formerly known as epidermolytic hyperkeratosis (EHK), and Lamellar Ichthyosis (LI); Ectrodactyly, Ectodermal dysplasia, and Cleft lip/palate (EEC) syndrome; Dyskeratosis Congenita (DC); connective tissue diseases and injuries (for example, osteoarthritis, bone fractures, and lipodystrophy); eye injuries and diseases such macular degeneration; neuronal disorders and injuries (e.g., Parkinson's disease and spinal cord injuries); cardiovascular diseases; respiratory diseases, hematopoietic and immune diseases; endocrine diseases (e.g., diabetes); liver diseases; infertility; cancer; and all areas of regenerative and reconstructive medicine.

In some embodiments, the methods disclosed herein can generate cells that can be utilized for repairing or regenerating a tissue or differentiated cell lineage in a subject. The method comprises generating a reprogrammed or dedifferentiated cell as described herein and administering the reprogrammed and/or dedifferentiated cell to a subject in need thereof. In some embodiments, the subject has a disease or disorder in which an increase or replacement of a particular cell type or cellular dedifferentiation is desirable, such as skin injuries (wounds) and diseases, including epidermolysis bullosa (EB), subtypes of skin blistering disorders such as EB simplex (EBS), junctional EB (JEB), dominant dystrophic EB (DDEB) and recessive dystrophic EB (RDEB), Kindler syndrome, acquired and congenital ichthyoses such as epidermolytic ichthyosis (EI), formerly known as epidermolytic hyperkeratosis (EHK), and Lamellar Ichthyosis (LI); Ectrodactyly, Ectodermal dysplasia, and Cleft lip/palate (EEC) syndrome; Dyskeratosis Congenita (DC); connective tissue diseases and injuries (for example, osteoarthritis, bone fractures, and lipodystrophy); eye injuries and diseases such macular degeneration; neuronal disorders and injuries (e.g., Parkinson's disease and spinal cord injuries); cardiovascular diseases, including Danon disease; respiratory diseases, hematopoietic and immune diseases; endocrine diseases (e.g., diabetes); liver diseases; infertility; Down Syndrome, or cancer.

In some embodiments, the subject has damage to a tissue or organ. In some embodiments, the subject has a deficiency of a particular cell type. In some embodiments, differentiated cells generated from the iPSCs produced by the methods disclosed herein can be used for tissue reconstitution or regeneration in a subject in need thereof.

Transfection Components

In contrast to conventional mod-mRNA reprogramming methods (See Warren et al., 2010 and Warren L, et al. *Sci Rep.* 2:657(2012), the methods of the present technology allow for successful reprogramming with less exogenous RNA (ExoRNA) (i.e., 700-10,500 ng mod-mRNA for the entire reprogramming; 5-1000 pmoles m-miRNAs for the entire reprogramming).

The methods described herein generate iPSCs via the transfection of primary human fibroblasts with a composition comprising mod-mRNA encoding a defined set of reprogramming factors alone or in combination with mature human microRNAs. Examples of reprogramming factors include, but are not limited to, one or more of Oct3 protein, Oct4 protein, Myo-D-Oct4 ($M_3O$) protein, Sox1 protein, Sox2 protein, Sox3 protein, Sox15 protein, Klf1, protein, Klf2 protein, Klf3 protein, Klf4 protein, Klf5 protein, c-Myc protein, L-Myc protein, N-Myc protein, Nanog protein, Lin28A protein, Tert protein, Utf1 protein, Aicda protein, Glis1, Sall4, Esrrb, Tet1, Tet2, Zfp42, Prdm14, Nr5a2, Gata6, Sox7, Pax1, Gata4, Gata3, cEBPa, HNF4a, GMNN, SNAIL, Grb2, Trim71, and biologically active fragments, analogues, variants, and family members thereof. Examples of mature human microRNAs include, but are not limited to, one or more of miR200s, miR290s, miR371s, miR302s, miR367, miR369s, and biologically active fragments, analogues, and variants thereof.

In some embodiments, the primary human fibroblasts are transfected with 1500 ng/10 cm$^2$ of a reprogramming mRNA cocktail. In some embodiments, the primary human fibroblasts are transfected with 1400 ng/10 cm$^2$ of a reprogramming mRNA cocktail. In some embodiments, the primary human fibroblasts are transfected with 1300 ng/10 cm$^2$ of a reprogramming mRNA cocktail. In some embodiments, the primary human fibroblasts are transfected with 1200 ng/10 cm$^2$ of a reprogramming mRNA cocktail. In some embodiments, the primary human fibroblasts are transfected with 1100 ng/10 cm$^2$ of a reprogramming mRNA cocktail. In some embodiments, the primary human fibroblasts are transfected with 1000 ng/10 cm$^2$ of a reprogramming mRNA cocktail. In some embodiments, the primary human fibroblasts are transfected with 900 ng/10 cm$^2$ of a reprogramming mRNA cocktail. In some embodiments, the primary human fibroblasts are transfected with 800 ng/10 cm$^2$ of a reprogramming mRNA cocktail. In some embodiments, the primary human fibroblasts are transfected with 700 ng/10 cm$^2$ of a reprogramming mRNA cocktail. In some embodiments, the primary human fibroblasts are transfected with 600 ng/10 cm$^2$ of a reprogramming mRNA cocktail. In some embodiments, the primary human fibroblasts are transfected with 500 ng/10 cm$^2$ of a reprogramming mRNA cocktail. In some embodiments, the primary human fibroblasts are transfected with 400 ng/10 cm$^2$ of a reprogramming mRNA cocktail. In some embodiments, the primary human fibroblasts are transfected with 300 ng/10 cm$^2$ of a reprogramming mRNA cocktail. In some embodiments, the primary human fibroblasts are transfected with 200 ng/10 cm$^2$ of a reprogramming mRNA cocktail. In some embodiments, the primary human fibroblasts are transfected with 100 ng/10 cm$^2$ of a reprogramming mRNA cocktail. In some embodiments, the primary human fibroblasts are transfected with 50 ng/10 cm$^2$ of a reprogramming mRNA cocktail. In some embodiments, the primary human fibroblasts are transfected with 100 to 1500 ng/10 cm$^2$ of a reprogramming mRNA cocktail. In other embodiments, the primary human fibroblasts are transfected with 100 to 600 ng/10 cm$^2$ of the reprogramming mRNA cocktail. In one aspect, the reprogramming mRNA cocktail comprises Oct4 or $M_3O$, Sox2, and Klf4 in a 3:1:1 molar ratio. In another aspect, the reprogramming mRNA cocktail comprises Oct4 or $M_3O$, Sox2, Klf4, and one or more of c-Myc, Lin28A, or Nanog in a 1:1 molar ratio with Sox2 and Klf4.

In some embodiments, the reprogramming modified mRNA cocktail comprises human Klf4, c-Myc, $M_3O$, Sox2, Lin28A, Nanog, and mWasabi. In some embodiments, the modified mRNA cocktail comprises 10% mWasabi modified mRNA, and Klf4, c-Myc, $M_3O$, Sox2, Lin28A, and Nanog in a 1:1:3:1:1:1 molar ratio.

In some embodiments, the primary human fibroblasts are transfected with 600 ng/10 cm$^2$ of a reprogramming mRNA cocktail comprising Klf4, c-Myc, $M_3O$, Sox2, Lin28A, and Nanog in a 1:1:3:1:1:1 molar ratio (i.e., 80.8 ng Klf4, 76.5 ng c-Myc, 221.1 ng $M_3O$, 63.8 ng Sox2, 42.5 ng Lin28A, 55.3 ng Nanog, and 60 ng mWasabi).

In some embodiments, the primary human fibroblasts are transfected with a reprogramming mRNA cocktail alone or in combination with a miRNA mix. In some embodiments, cells are transfected with 50 pmoles/10 cm$^2$ reprogramming miRNA (e.g., miR-367 and miR-302s). In some embodiments, cells are transfected with 40 pmoles/10 cm$^2$ reprogramming miRNA. In some embodiments, cells are transfected with 30 pmoles/10 cm$^2$ reprogramming miRNA. In some embodiments, cells are transfected with 20 pmoles/10 cm$^2$ reprogramming miRNA. In some embodiments, cells are transfected with 15 pmoles/10 cm$^2$ reprogramming miRNA. In some embodiments, cells are transfected with 10 pmoles/10 cm$^2$ reprogramming miRNA. In some embodiments, cells are transfected with 5 pmoles/10 cm$^2$ reprogramming miRNA. In some embodiments, cells are transfected with 2 pmoles/10 cm$^2$ reprogramming miRNA. In some embodiments, cells are transfected with 1 pmoles/10 cm$^2$ reprogramming miRNA. In some embodiments, cells are transfected with 1 to 50 pmoles/10 cm$^2$ reprogramming miRNA. In some embodiments, cells are transfected with 10 to 40 pmoles/10 cm$^2$ reprogramming miRNA. In some embodiments, cells are transfected with 5 to 40 pmoles/10 cm$^2$ reprogramming miRNA.

In some embodiments, the primary human fibroblasts are transfected with miRNA367, miRNA302a, miRNA302b, miRNA302c, and miRNA302d in a 1:1:1:1:1 molar ratio.

In some embodiments, the reprogramming efficiency of the present technology is enhanced by tailoring the cell transfection regimen and cell seeding conditions specifically to primary human fibroblasts. The primary human fibroblasts are typically cultured in medium containing Knock-Out Serum Replacement (KOSR medium) and RNA transfections are performed with the transfection reagent, LIPOFECTAMINE® RNAiMAX™. In some embodiments, reprogramming efficiency is enhanced by the addition of a complexation buffer that mediates that formation of transfection complexes between RNAs and cationic lipids. In some embodiments, the complexation buffer is OPTI-MEM® or PBS.

In some embodiments, cells are seeded at a density of about 10,000 cells/cm$^2$ or less and transfected with 1,000 ng/10 cm$^2$ of a reprogramming mRNA cocktail and 20 pmoles/10 cm$^2$ of reprogramming miRNAs per transfection every 48 hrs for a duration of 13 days (7 transfections). In some embodiments, cells are seeded at a density of about 10,000 cells/cm$^2$ or less and transfected with 1,000 ng/10 cm$^2$ of a reprogramming mRNA cocktail and 10 pmoles/10 cm$^2$ of reprogramming miRNAs. In some embodiments, cells are seeded at a density of about 10,000 cells/cm$^2$ or less and transfected with 1,000 ng/10 cm$^2$ of a reprogramming mRNA cocktail and 5 pmoles/10 cm$^2$ of reprogramming miRNAs.

In some embodiments, cells are seeded at a density of about 10,000 cells/cm$^2$ or less and transfected with 600 ng/10 cm$^2$ of a reprogramming mRNA cocktail and 20 pmoles/10 cm$^2$ of reprogramming miRNAs. In some embodiments, cells are seeded at a density of about 10,000 cells/cm$^2$ or less and transfected with 600 ng/10 cm$^2$ of a reprogramming mRNA cocktail and 10 pmoles/10 cm$^2$ of reprogramming miRNAs. In some embodiments, cells are seeded at a density of about 10,000 cells/cm$^2$ or less and transfected with 600 ng/10 cm$^2$ of a reprogramming mRNA cocktail and 5 pmoles/10 cm$^2$ of reprogramming miRNAs.

In some embodiments, cells are seeded at a density of about 10,000 cells/cm$^2$ or less and transfected with 300 ng/10 cm$^2$ of a reprogramming mRNA cocktail and 20 pmoles/10 cm$^2$ of reprogramming miRNAs. In some embodiments, cells are seeded at a density of about 10,000 cells/cm$^2$ or less and transfected with 300 ng/10 cm$^2$ of a reprogramming mRNA cocktail and 10 pmoles/10 cm$^2$ of reprogramming miRNAs. In some embodiments, cells are seeded at a density of about 10,000 cells/cm$^2$ or less and transfected with 300 ng/10 cm$^2$ of a reprogramming mRNA cocktail and 5 pmoles/10 cm$^2$ of reprogramming miRNAs.

In some embodiments, cells are seeded at a density of about 10,000 cells/cm$^2$ or less and transfected with 100 ng/10 cm$^2$ of a reprogramming mRNA cocktail and 20 pmoles/10 cm$^2$ of reprogramming miRNAs. In some embodiments, cells are seeded at a density of about 10,000 cells/cm$^2$ or less and transfected with 100 ng/10 cm$^2$ of a reprogramming mRNA cocktail and 10 pmoles/10 cm$^2$ of reprogramming miRNAs. In some embodiments, cells are seeded at a density of about 10,000 cells/cm$^2$ or less and transfected with 100 ng/10 cm$^2$ of a reprogramming mRNA cocktail and 5 pmoles/10 cm$^2$ of reprogramming miRNAs.

In some embodiments, cells are seeded at a density of about 9,000 cells/cm$^2$ or less and transfected with 1,000 ng/10 cm$^2$ of a reprogramming mRNA cocktail and 20 pmoles/10 cm$^2$ of reprogramming miRNAs per transfection every 48 hrs for the duration of 13 days (7 transfections). In some embodiments, cells are seeded at a density of about 10,000 cells/cm$^2$ or less and transfected with 1,000 ng/10 cm$^2$ of a reprogramming mRNA cocktail and 10 pmoles/10 cm$^2$ of reprogramming miRNAs. In some embodiments, cells are seeded at a density of about 10,000 cells/cm$^2$ or less and transfected with 1,000 ng/10 cm$^2$ of a reprogramming mRNA cocktail and 5 pmoles/10 cm$^2$ of reprogramming miRNAs.

In some embodiments, cells are seeded at a density of about 9,000 cells/cm$^2$ or less and transfected with 600 ng/10 cm$^2$ of a reprogramming mRNA cocktail and 20 pmoles/10 cm$^2$ of reprogramming miRNAs. In some embodiments, cells are seeded at a density of about 10,000 cells/cm$^2$ or less and transfected with 600 ng/10 cm$^2$ of a reprogramming mRNA cocktail and 10 pmoles/10 cm$^2$ of reprogramming miRNAs. In some embodiments, cells are seeded at a density of about 10,000 cells/cm$^2$ or less and transfected with 600 ng/10 cm$^2$ of a reprogramming mRNA cocktail and 5 pmoles/10 cm$^2$ of reprogramming miRNAs.

In some embodiments, cells are seeded at a density of about 9,000 cells/cm$^2$ or less and transfected with 300 ng/10 cm$^2$ of a reprogramming mRNA cocktail and 20 pmoles/10 cm$^2$ of reprogramming miRNAs. In some embodiments, cells are seeded at a density of about 10,000 cells/cm$^2$ or less and transfected with 300 ng/10 cm$^2$ of a reprogramming mRNA cocktail and 10 pmoles/10 cm$^2$ of reprogramming miRNAs. In some embodiments, cells are seeded at a density of about 10,000 cells/cm$^2$ or less and transfected with 300 ng/10 cm$^2$ of a reprogramming mRNA cocktail and 5 pmoles/10 cm$^2$ of reprogramming miRNAs.

In some embodiments, cells are seeded at a density of about 9,000 cells/cm$^2$ or less and transfected with 100 ng/10 cm$^2$ of a reprogramming mRNA cocktail and 20 pmoles/10 cm$^2$ of reprogramming miRNAs. In some embodiments, cells are seeded at a density of about 9,000 cells/cm$^2$ or less and transfected with 100 ng/10 cm$^2$ of a reprogramming mRNA cocktail and 10 pmoles/10 cm$^2$ of reprogramming miRNAs. In some embodiments, cells are seeded at a density of about 9,000 cells/cm$^2$ or less and transfected with 100 ng/10 cm$^2$ of a reprogramming mRNA cocktail and 5 pmoles/10 cm$^2$ of reprogramming miRNAs.

In some embodiments, cells are seeded at a density of about 0.1-10,000 cells/cm$^2$ or less and transfected with 1,000 ng/10 cm$^2$ of a reprogramming mRNA cocktail and 20 pmoles/10 cm$^2$ of reprogramming miRNAs per transfection every 48 hrs for the duration of 13 days (7 transfections). In some embodiments, cells are seeded at a density of about 0.1-10,000 cells/cm$^2$ or less and transfected with 1,000 ng/10 cm$^2$ of a reprogramming mRNA cocktail and 10 pmoles/10 cm$^2$ of reprogramming miRNAs. In some embodiments, cells are seeded at a density of about 0.1-10,000 cells/cm$^2$ or less and transfected with 1,000 ng/10 cm$^2$ of a reprogramming mRNA cocktail and 5 pmoles/10 cm$^2$ of reprogramming miRNAs.

In some embodiments, cells are seeded at a density of about 0.1-10,000 cells/cm$^2$ or less and transfected with 600 ng/10 cm$^2$ of a reprogramming mRNA cocktail and 20 pmoles/10 cm$^2$ of reprogramming miRNAs. In some embodiments, cells are seeded at a density of about 0.1-10,000 cells/cm$^2$ or less and transfected with 600 ng/10 cm$^2$ of a reprogramming mRNA cocktail and 10 pmoles/10 cm$^2$ of reprogramming miRNAs. In some embodiments, cells are seeded at a density of about 0.1-10,000 cells/cm$^2$ or less and transfected with 600 ng/10 cm$^2$ of a reprogramming mRNA cocktail and 5 pmoles/10 cm$^2$ of reprogramming miRNAs.

In some embodiments, cells are seeded at a density of about 0.1-10,000 cells/cm$^2$ or less and transfected with 300 ng/10 cm$^2$ of a reprogramming mRNA cocktail and 20 pmoles/10 cm$^2$ of reprogramming miRNAs. In some embodiments, cells are seeded at a density of about 0.1-10,000 cells/cm$^2$ or less and transfected with 300 ng/10 cm$^2$ of a reprogramming mRNA cocktail and 10 pmoles/10 cm$^2$ of reprogramming miRNAs. In some embodiments, cells are seeded at a density of about 0.1-10,000 cells/cm² or less and transfected with 300 ng/10 cm² of a reprogramming mRNA cocktail and 5 pmoles/10 cm² of reprogramming miRNAs.

In some embodiments, cells are seeded at a density of about 0.1-10,000 cells/cm² or less and transfected with 100 ng/10 cm² of a reprogramming mRNA cocktail and 20 pmoles/10 cm² of reprogramming miRNAs. In some embodiments, cells are seeded at a density of about 0.1-10,000 cells/cm² or less and transfected with 100 ng/10 cm² of a reprogramming mRNA cocktail and 10 pmoles/10 cm² of reprogramming miRNAs. In some embodiments, cells are seeded at a density of about 0.1-10,000 cells/cm² or less and transfected with 100 ng/10 cm² of a reprogramming mRNA cocktail and 5 pmoles/10 cm² of reprogramming miRNAs.

Kits

Also disclosed herein are kits for reprogramming primary human fibroblast cells. In some embodiments, the kits include a reprogramming mRNA cocktail, reprogramming miRNA, and instructions for reprogramming a plurality of primary human fibroblast cells. In some embodiments, the kits include a reprogramming mRNA cocktail, reprogramming miRNA and instructions for reprogramming a single, individually plated primary human fibroblast cell. In some embodiments, kits include a complexation buffer, a reprogramming medium, and a transfection reagent.

EXPERIMENTAL EXAMPLES

The present technology is further illustrated by the following examples, which should not be construed as limiting in any way.

Example 1: Reprogramming Fibroblasts

A. Preparation of a Modified mRNA Mix ("Reprogramming Cocktail") and Combined m-miRNAs Transcripts of six reprogramming factors (OCT4 or Myo-D-OCT4 ($M_3O$), SOX2, KLF4, c-MYC, NANOG and LIN28A (abbreviated as "O.SKMNL")) were prepared as modified mRNA (mod-mRNA) as follows.

Modified mRNA (mod-mRNA) was synthesized as described in Warren, et al. *Cell Stem Cell* 7:618-630 (2010), with slight modifications. Briefly, MEGAscript T7 kit (Life Technologies, Grand Island, N.Y.) was used and 1.6 µg of template PCR product for each 40 µl reaction was used. A 2.5× custom ribonucleoside mix including 15 mM 3'-0-Me-m⁷G(5')ppp(5')G ARCA cap analog (New England Biolabs), 3.75 mM guanosine triphosphate and 18.75 mM adenosine triphosphate (both were used from MEGAscript T7 kit), 18.75 mM 5-methylcytidine triphosphate and 18.75 mM pseudouridine triphosphate (TriLink Biotechnologies, San Diego, Calif.) was prepared. RNA synthesis reactions were incubated at 37° C. for 6 hours and then treated with DNase for 15 minutes at 37° C. as directed by the manufacturer. RNA was purified with RNeasy Mini Kit columns (QIAGEN) and then treated with Antarctic Phosphatase (New England Biolabs) for 30 min at 37° C. After re-purification, RNA was eluted with nuclease-free dH₂O supplemented with 1 U/µl of RIBOGUARD™ RNase Inhibitor (Epicentre Biotechnologies, Madison, Wis.). RNA was then quantitated by Nanodrop (Thermo Scientific, Waltham, Mass.) and stored at -70° C. until further use.

Unless otherwise noted, the mod-mRNA mix used for reprogramming ("reprogramming cocktail") contained 6 reprogramming factors, $M_3O$, SOX2, KLF4, c-MYC, NANOG and LIN28A (abbreviated as "$O_m$SKMNL"), at a molar stoichiometry of Myo-D-Oct4 ($M_3O$) to the other 5 factors as 3:1:1:1:1:1 and included 10% mWasabi mod-mRNA to control for the transfection. For reprogramming and transfection experiments mod-mRNA mix or mWasabi mod-mRNA alone were prepared at 100 ng/µl in nuclease-free dH₂O supplemented with 1 U/µl of RIBOGUARD™ RNase.

A m-miRNA mix was prepared as follows. MiR-367/302s as miScript miRNA mimic (Syn-has-miR-367-3p, Syn-has-miR-302a-3p, Syn-has-miR-302b-3p, Syn-has-miR-302c-3p, and Syn-has-miR-302d-3p) or controls (AllStars Neg. Control siRNA and fluorescently labeled AllStars Neg. siRNA AF 488) were purchased from QIAGEN. Lyophilized products were dissolved to 5 µM final concentration in dH₂O supplemented with 1 U/µl of RIBOGUARD™ RNase Inhibitor. Stocks were frozen at -70° C. until further use. Individual m-miRNA-367/302s stocks were mixed in 1:1:1:1:1 ratio to prepare a 5 µM m-miRNA mix.

B. Transfection Procedure

1. Cells

Primary human neonatal fibroblasts were cultured in either human dermal fibroblast (HDF) or medium containing KNOCKOUT™ Serum Replacement until transfection. Cells were then treated as follows. Tissue culture 6-well format dishes (Corning Inc., Tewksbury, Mass.) were coated with GELTREX® Matrix (Life Technologies, Grand Island, N.Y.) at 100× dilution in plain DMEM/F12 (Life Technologies, Grand Island, N.Y.) for 1 hour at 37° C. in a 5% CO₂ tissue culture incubator. Primary patient neonatal and adult fibroblasts were plated onto the GELTREX®-coated dishes at densities ranging from 200 to 100,000 cells per well of the 6-well dish format. The plating medium contained modified DMEM/F12 with L-glutamine and no HEPES (catalog #11320), 20% KNOCKOUT™ Serum Replacement, 5% Heat Inactivated FBS, 0.2% of 100×MEM Non-Essential Amino Acids Solution, 0.4 mM GLUTAMAX™ Supplement, 55 µM of 2-Mercaptoethanol, 1% of 100× Antibiotic-Antimycotic solution (all from Life Technologies, Grand Island, N.Y.), 50 µg/mL L-Ascorbic Acid (Sigma-Aldrich, St. Louis, Mo.) and was supplemented with 100 ng/mL basic FGF (Life Technologies, Grand Island, N.Y.) and 200 ng/mL B18R (eBioscience, San Diego, Calif.). The plated cells were incubated overnight in a 5% O₂/5% CO₂ tissue culture incubator.

The following day the medium was changed to KOSR medium containing modified DMEM/F12 with L-glutamine and no HEPES (catalog #11320), 20% KNOCKOUT™ Serum Replacement, 0.2% of 100×MEM Non-Essential Amino Acids Solution, 0.4 mM GLUTAMAX™ Supplement, 55 µM of 2-Mercaptoethanol, 1% of 100× Antibiotic-Antimycotic solution (all from Life Technologies, Grand Island, N.Y.), 50 µg/mL L-Ascorbic Acid (Sigma-Aldrich, St. Louis, Mo.). KOSR Medium was equilibrated overnight at 5% O₂ before each medium change and supplemented with fresh 100 ng/mL bFGF (Life Technologies, Grand Island, N.Y.) and 200 ng/mL B18R. The volume used per well in a 6-well dish format was 1 mL.

2. Preparation of RNA Solutions and Cells for Transfection

Either pH-adjusted 1×PBS or pH-adjusted OPTI-MEM® I Reduced Serum Medium (Life Technologies, Grand Island, N.Y.) was used as a complexation buffer. To prepare the transfection mix, RNAiMAX™ LIPOFECTAMINE® (Life Technologies, Grand Island, N.Y.), RNA molecules (for mWasabi transfections, modified mRNA transfections, and m-miRNAs transfections), and complexation buffer were combined as described below.

The complexation between RNAiMAX™ LIPO-FECTAMINE® and mRNA was performed in either pH-adjusted OPTI-MEM® or pH-adjusted-PBS. pH values evaluated are shown in Tables 2 and 3 below.

The pH of commercially supplied OPTI-MEM® is 7.2-7.3. For transfection experiments, the pH of OPTI-MEM® was adjusted to the indicated value with 1M NaOH. The pH of 1×PBS was adjusted using either 1M NaOH or 1M HCl. Strict RNase-free conditions were maintained for OPTI-MEM® and 1×PBS preparation, and following pH adjustment both OPTI-MEM® and 1×PBS were filter sterilized.

RNA and RNAiMAX™ LIPOFECTAMINE® reagent were first diluted in pH-adjusted OPTI-MEM® reduced serum medium (Life Technologies, Grand Island, N.Y.) or 1× pH-adjusted PBS. For mod-mRNA transfections, 100 ng/µl RNA was diluted 5× and 5 µl of RNAiMAX™ LIPOFECTAMINE® per microgram of RNA was diluted 10×. After dilution these components were combined together and incubated for 15 min at room temperature (RT). For the m-miRNA transfections, a 5 µM (5 pmol/µl) m-miRNA mix was diluted to 0.6 pmol/µl and 1 µl of RNAiMAX™ LIPOFECTAMINE® per 6 picomoles was diluted 10×. The diluted m-miRNA mix and RNAiMAX™ LIPOFECTAMINE® were mixed together and incubated for 15 minutes at RT. After incubation at RT, mixtures of mod-RNA mix and/or m-miRNA mix and RNAiMAX™ LIPOFECTAMINE® were applied to the cell culture. For samples including both the mod-mRNA mix and m-miRNA mix, mod-mRNA mix was applied first, followed by the m-miRNA mix. The tables below summarize the transfection reagents. 20 pmoles m-miRNA was used per well (m-miRNA amounts in the range of 10-40 pm were tested and also worked, data not shown).

TABLE 2

| Sample | m-miRNA (20 pmoles) | mod-mRNA mix* | pH PBS buffer |
|---|---|---|---|
| 1 | − | 600 ng | pH 7.9 |
| 2 | + | | |
| 3 | − | 300 ng | |
| 4 | + | | |
| 5 | − | 200 ng | |
| 6 | + | | |
| 7 | − | 100 ng | |
| 8 | + | | |
| 9 | − | 600 ng | pH 7.3 |
| 10 | + | | |

*All 6 reprogramming factors were present.

TABLE 3

| Sample | m-miRNA (20 pmoles) | mod-mRNA mix | mod-mRNA mix components* | pH OptiMEM buffer |
|---|---|---|---|---|
| 1 | − | 600 ng | d2eGFP | 8.2 |
| 2 | + | | | |
| 3 | − | 600 ng | $M_3O$ | 7.3 |
| 4 | + | | | |
| 5 | − | 600 ng | $M_3O$ | 8.6 |
| 6 | + | | | |
| 7 | − | 600 ng | $M_3O$ | 7.8 |
| 8 | + | | | |
| 9 | − | 600 ng | $M_3O$ | 8.2 |
| 10 | + | | | |
| 11 | − | 100 ng | $M_3O$ | |
| 12 | + | | | |
| 13 | − | 1000 ng | $M_3O$ | |
| 14 | + | | | |
| 15 | + | 600 ng | Oct 4 | |
| 16 | − | | | |
| 17 | | 600 ng | Oct 4, no Nanog | |
| 18 | | | | |

*All samples included $M_3O$ or OCT4 as indicated, SOX2, KLF4, c-MYC, NANOG (except samples 17 and 18) and LIN28A. Samples 1 and 2 were transfected with d2eGFP, a destabilized variant of enhanced Green Fluorescent Protein (eGFP).

3. Transfections

Figure 34:
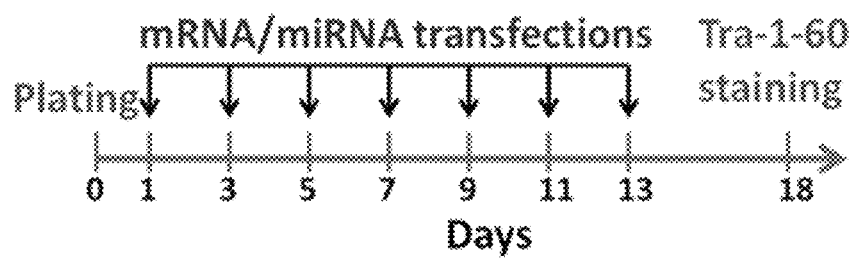
FIG. 34 illustrates a timeline of mRNA/miRNA transfections.

Seven transfections were performed at 48 hour intervals, as shown in FIG. 34. Regimens in which transfections were performed every 24, 48, or 72 hours were also tested. In the 24 hour regimen, 11 consecutive transfections were performed. In the 48 hour regimen, up to seven transfections were performed. In the 72 hour regimen, a maximum of 5 transfections were performed. Each of these regimens provided positive results (data not shown).

KOSR medium was changed 24 hours after each transfection.

After completing the series of seven transfections, the medium (KOSR Medium supplemented with 100 ng/mL bFGF (Life Technologies, Grand Island, N.Y.)) was changed every day and the cells were grown up to Day 18, at which point the wells were stained with anti-Tra-1-60 antibody by methods well-known in the art, and the number of Tra-1-60 positive, iPSC colonies was counted.

C. Results

Results are shown in FIG. 1. For FIG. 1, neonatal fibroblast cells were plated at a density of 500 cells per well of the 6-well dish format. "5f$M_3$O" represents a 6 factor cocktail containing $M_3$O, Sox2, Klf4, c-Myc, Lin28A and Nanog. "5fOCT4" represents a 6 factor cocktail containing Oct4, Sox2, Klf4, c-Myc, Lin28A and Nanog. "4fOCT4" represents a 5 factor cocktail containing Oct4, Sox2, Klf4, c-Myc and Lin28A. The "+" stands for 20 pmoles of m-miRNA367/302s. The "−" stands for no m-miRNA. "NEG" stands for the negative m-miRNA (AllStars Neg. Control siRNA, Qiagen). Each mod-mRNA cocktail also contained 10% of mWasabi mod-mRNA to monitor the transfection efficiency.

None of the tested conditions resulted in the formation of Tra-1-60$^+$ colonies when regular, unadjusted OPTI-MEM® at pH 7.3 (OM-7.3) was used for the complexation of RNAiMAX' LIPOFECTAMINE® with mod-mRNAs and m-miRNAs (FIG. 1). Transfections with m-miRNAs alone also failed to induce iPSC formation.

Surprisingly, an unprecedented reprogramming efficiency was achieved when a 6-factor reprogramming mod-mRNA cocktail was transfected in combination with m-miRNAs using OM-8.2 as a transfection buffer. This resulted in up to 4,019 Tra-1-60$^+$ colonies per 500 initially plated human primary neonatal fibroblasts (FIG. 1). In this regimen, the first Tra-1-60$^+$ cells emerge as early as Day 8 of the protocol.

Reprogramming was also performed using PBS as a transfection buffer (FIG. 1). PBS showed a higher baseline of mod-mRNA transfection efficiency than OM-8.2 (data not shown). When 600 ng of mod-mRNAs were used in transfections performed every 48 hours using PBS as a transfection buffer, cells performed poorly regardless of the presence of m-miRNAs (FIG. 1). Titrating down of the amount of mod-mRNA delivered with PBS as a complexation buffer resulted in a higher reprogramming efficiency when only 200 ng of mod-mRNAs were used per transfection in a 48 hour regimen (FIG. 1). This suggests that balancing the efficiency of mod-mRNA transfections can play a role in the reprogramming efficiency of primary human fibroblasts.

These results show that the mod-mRNAs in combination with m-miRNAs synergistically improve the efficiency of iPSC generation from primary human fibroblasts.

Example 2: Single Cell Reprogramming

To overcome the cell stress caused by fluorescence-activated cell sorting (FACS), a limiting dilution approach was employed, in which primary human neonatal fibroblasts were plated at very low cell densities (<1 cell per well) onto GELTREX®-coated 48 well plates in KOSR medium supplemented with 5% FBS, 100 ng/mL bFGF and 200 ng/mL as described above. The following day, each well was screened under the microscope to ensure that only 1 cell was seeded per well. The wells with no cells or more than 1 cell were eliminated from the experiment. The amount of RNAs was adjusted to the surface area as well as the volume of medium used throughout the regimen. For each well, 150 µL of KOSR medium supplemented with bFGF and B18R were used, and 100 ng of mod-mRNA mix comprising $M_3O$ and 2 pmoles of m-miRNA mix comprising miRNA367/302s were used per well per transfection. Seven transfections were performed at 48 hour intervals as described in Example 1, and KOSR medium was changed 24 hours after each transfection. After completing the series of transfections, the medium was changed every day and the cells were grown up to Day 18, at which point the wells were stained with anti-Tra-1-60 antibody and the number of wells with resulting iPSC colonies was counted. The experiment was performed for 3 independent human primary neonatal lines (FN1, FN2, and FN3). Results are shown in Table 4 below and in FIGS. 2 and 3.

TABLE 4

| Primary Neonatal Cell Line | Mature microRNAs | Wells with an individually plated single cell | Wells with dividing cells throughout reprogramming | Wells with Tra-1-60⁺ colonies | Reprogramming efficiency (%) Wells with Tra-1-60⁺ colonies/wells with dividing cells × 100% |
|---|---|---|---|---|---|
| FN1 | + | 157 | 144 | 106 | 73.6% |
|  | − | 134 | 116 | 0 | 0% |
| FN2 | + | 141 | 130 | 101 | 77.7% |
|  | − | 107 | 98 | 8 | 8.2% |
| FN5 | + | 110 | 108 | 98 | 90.7% |
|  | − | 111 | 110 | 16 | 14.5% |

Figure 2:
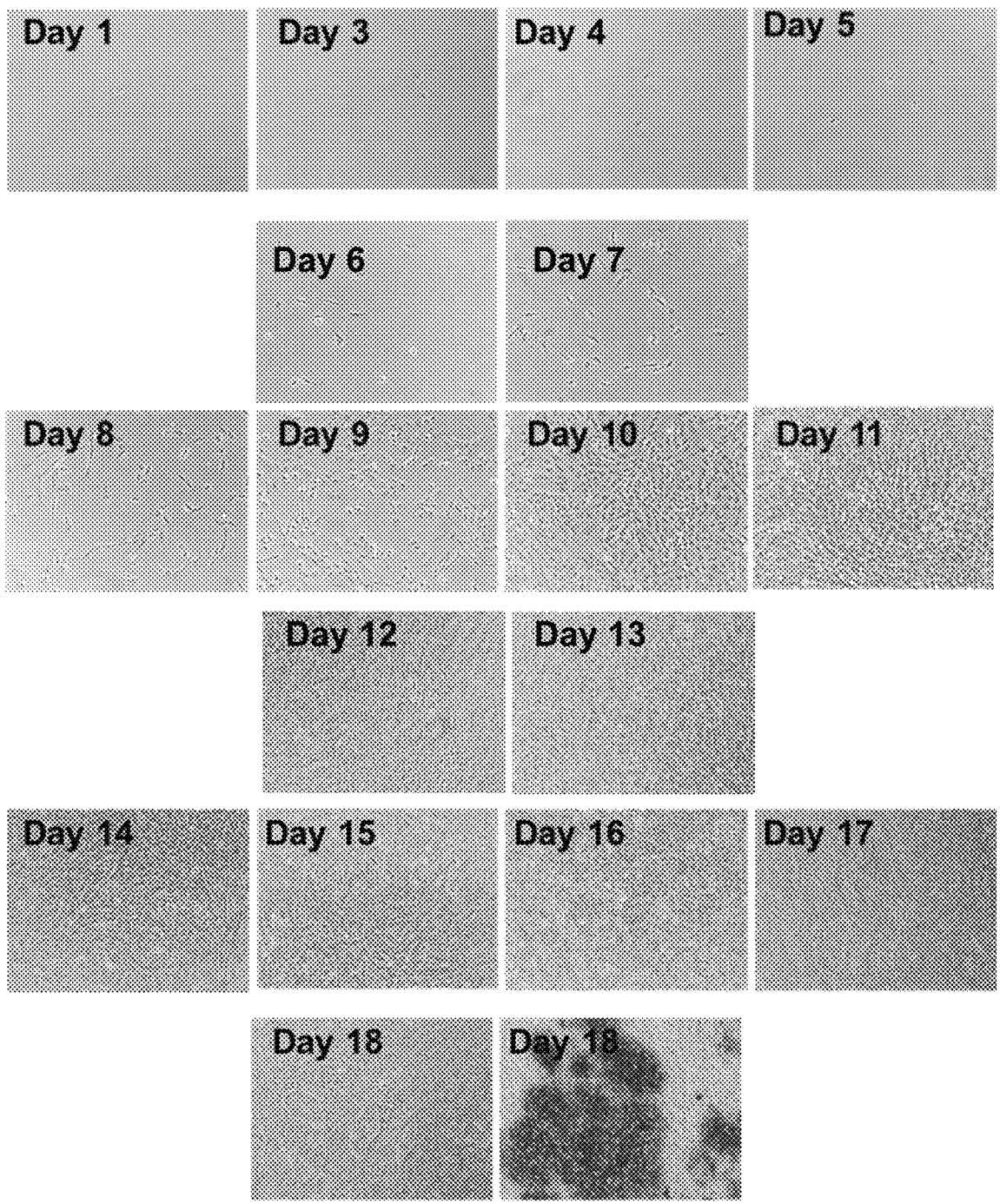
FIG. 2 is a series of micrographs taken with a 10× objective (100× magnification) showing daily reprogramming progression of an individually plated single primary human fibroblast cell. On Day 18, the cells were stained with anti-Tra-1-60 antibody.
Figure 3:
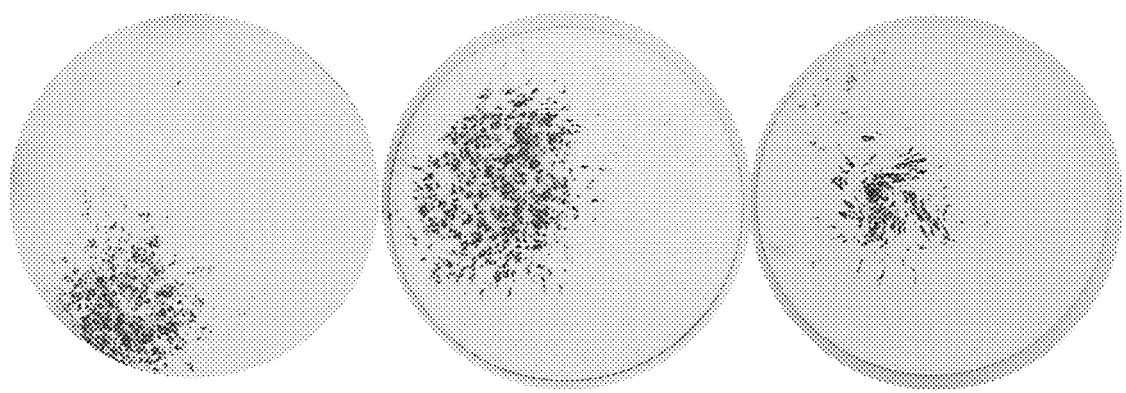
FIG. 3 shows a set of representative images of wells in a 48-well format stained for Tra-1-60 on Day 18 of a single cell reprogramming protocol.

Up to 90.7% of individually plated single cells were reprogrammed (Table 4); with the majority of input cells producing multiple Tra-1-60⁺ colonies (FIGS. 2 and 3). If m-miRNAs were excluded from the regimen, the efficiency of a single cell reprogramming dropped (Table 4), further demonstrating the synergistic effect of reprogramming mod-mRNAs and m-miRNAs on the efficiency of iPSC generation in the disclosed methods.

Example 3: Evaluation of Plating Density and Reprogramming Efficiency

To assess the effects of the initial seeding density of human primary fibroblast cells on the reprogramming efficiency of the combinatorial RNA-based approach disclosed herein, a series of reprogramming experiments using human primary neonatal fibroblasts plated at different densities were performed. Cells were transformed according to the methods described in Example 1, using OPTI-MEM® at pH 8.2, 20 pmole m-miRNA mix, 600 ng of mod-mRNA mix (including $M_3O$), with 7 transfections, one every 48 hours. KOSR medium was changed 24 hours after each transfection. After the last transfection, the medium was changed every day and cells were grown to 18 days and stained for Tra-1-60⁺ expression.

Figure 4:
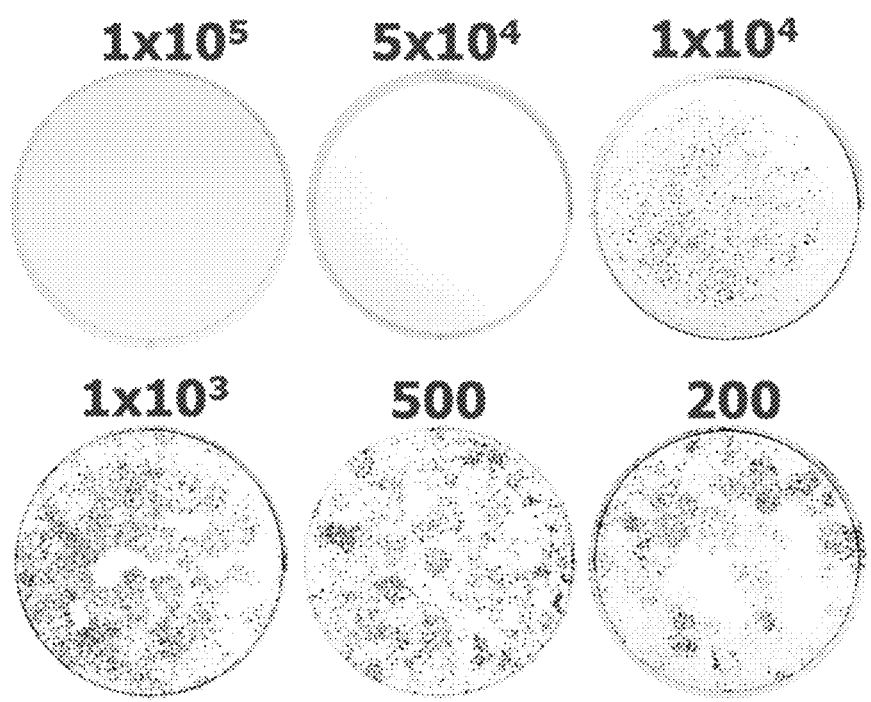
FIG. 4 is a series of representative images of wells from a 6-well format stained for Tra-1-60 on Day 18 of reprogramming with the combined mod-mRNA mix and m-miRNA mix described herein. The initial plating densities of human primary fibroblasts are indicated for each of the wells.

Results are shown in Table 5 and FIG. 4.

TABLE 5

| Cells plated/well (6-well format ~10 cm²) | Tra-1-60⁺ colonies/well | Reprogramming efficiency (%) |
|---|---|---|
| 100,000 | 0.33 ± 0.58 | 0.0003% ± 0.0006% |
| 50,000 | 4.7 ± 6.43 | 0.0093% ± 0.0129% |
| 10,000 | 663.7 ± 302.74 | 6.64% ± 1.64% |
| 5,000 | 1113.7 ± 151.28 | 22.27% ± 3.03% |
| 1,000 | 3408.7 ± 163.9 | 340.87% ± 16.39% |
| 500 | 3896 ± 131.14 | 779.20% ± 26.23% |
| 200 | 1647.3 ± 364.06 | 823.67% ± 182.03% |

The initial seeding density which allows for the generation of Tra-1-60⁺ colonies was 10,000 cells/well in a 6-well dish format. The colonies did not form at an initial density above 100,000 cells/well.

Reprogramming efficiency is traditionally calculated as the number of resulting iPSC colonies divided by the number of input cells. If applied to some embodiments of the methods disclosed herein, these calculations would indicate up to 800% of reprogramming efficiency (see Table 5 above). This number is achieved when multiple sister iPSC colonies derive from a single parental cell.

Example 4: The Number of Transfections Influences Reprogramming Efficiency 500 human neonatal fibroblast cells were plated in a 6-well dish and transfected as described in Example 1 (using OPTI-MEM® at pH 8.2, 20 pmole m-miRNA mix and 600 ng of mod-mRNA mix (including $M_3O$)). Cells were transfected every other day starting at Day 1 after plating; however, the total number of transfections was varied for each sample. Sample 1 was transfected 2× (on Day 1 and Day 3); sample 2 was transfected 3× (Day 1, Day 3 and Day 5); sample 4 was transfected 4× (Day 1, 3, 5 and 7); sample 5 was transfected 6× (Day 1, 3, 5, 7, 9 and 11) and sample 6 was transfected 7× (Day 1, 3, 5, 7, 9, 11 and 13). The medium was changed 24 hours after each transfection. After the last transfection, the medium was changed daily to 18 days. At Day 18, cells were stained for Tra-1-60 expression and positive colonies were counted. Results are shown in FIG. 5.

Example 5: The Combinatorial RNA-Based Approach Produces Stable iPSC Lines from Neonatal, Adult, Diseased, and Senescent Fibroblasts The applicability of the combinatorial RNA-based approach disclosed herein on the reprogramming of primary human fibroblasts lines derived from adult patients was assessed.

Fibroblasts derived from 3 different inherited skin blistering disorders were successfully reprogrammed. Successful, high efficiency reprogramming was also achieved with fibroblasts derived from an individual suffering from Danon disease (FDanon); 2 patients with Down Syndrome (FDown1 and FDown2), 4 healthy individuals of 34 (F34), 40 (F40), 41(F41) and 50 (F50) years of age; senescent line derived from F50 (F50S), and 3 healthy neonatal lines (FN1, FN2, and FN5) (Table 6, below). The inherited skin blistering disorders were EHK (FEH1), EBS (FEB1), RDEB (FRD1 and FRD2).

Cells were collected from subjects using methods well known in the art and cultured in DMEM supplemented with 10% fetal bovine serum. Cells were plated at an initial density ranging from 1000-5000 cells per well of a 6-well format plate in KOSR medium as described in Example 1. Cells were transfected as described in Example 1, using OPTI-MEM® at pH 8.2, 20 pmole m-miRNA mix, 600 or 1000 ng of mod-mRNA mix (including $M_3O$), with 7 transfections, one every 48 hours. KOSR medium was changed 24 hours after each transfection. After the last transfection, the medium was changed daily and cells were grown to 18 days and stained for Tra-1-60$^+$ expression.

TABLE 6

| Neonatal, Adult, Senescent, Healthy, and Diseased Fibroblast Lines (Age of individual in years) | Initial Cells Plated/Well (6-well format = 10 cm$^2$) | iPSC Colonies/Well | Reprogramming Efficiency (%) |
|---|---|---|---|
| FN1 | 500 | 3132 ± 240.04 | 626.4% ± 48.01% |
| FN2 | 500 | 3896 ± 131.14 | 779.2% ± 26.23% |
| FN5 | 500 | 2161.7 ± 258.8 | 432.3% ± 51.76 |
| F50 (50) | 5000 | 1821.7 ± 90.5 | 36.43% ± 1.81% |
| F50S (F50 senescent) | 100000 | 325 ± 88.66 | 0.33% ± 0.09% |
| F41 (41) | 5000 | 683.3 ± 90.42 | 13.7% ± 1.82% |
| F34 (34) | 2000 | ~2500 | ~125% |
| F40 (40) | 2000 | 1453.3 ± 93.33 | 72.67% ± 4.67% |
| FEH1 (5) | 1000 | 405.7 ± 14.57 | 40.57% ± 1.46% |
| FEB1 (30) | 3000 | 363.7 ± 44.5 | 12.1% ± 1.5% |
| FRD1 (25) | 3000 | 125.7 ± 33.13 | 4.2% ± 1.1% |
| FRD2 | 3000 | ~100 | ~3.3% |
| FDanon | 3000 | ~250 | ~8.3% |
| FDown1 | 3000 | ~600 | ~20% |
| FDown2 | 3000 | ~450 | ~15% |

F—stands for human dermal fibroblast; FN—neonatal fibroblasts, F50—fibroblasts from healthy 50 year old patient, F50S—senescent line derived from F50, F41—fibroblasts from healthy 41 year old patient, F34—fibroblasts from healthy 34 year old patient, F40—fibroblasts from healthy 40 year old patient, FEH1—fibroblasts from patient with EHK disease (EHK stands for epidermolytic hyperkeratosis), FEB1—fibroblasts from patient with EBS disease (EBS stands for epidermolysis bullosa simplex), FRD1 and FRD2—fibroblasts from 2 patients with RDEB disease (RDEB stands for recessive dystrophic epidermolysis bullosa), FDanon—fibroblasts derived from a patient Danon disease (cardiomyopathy), FDown1 and FDown2—fibroblasts from 2 patients with Down Syndrome (trisomy 21).

Figure 6A:
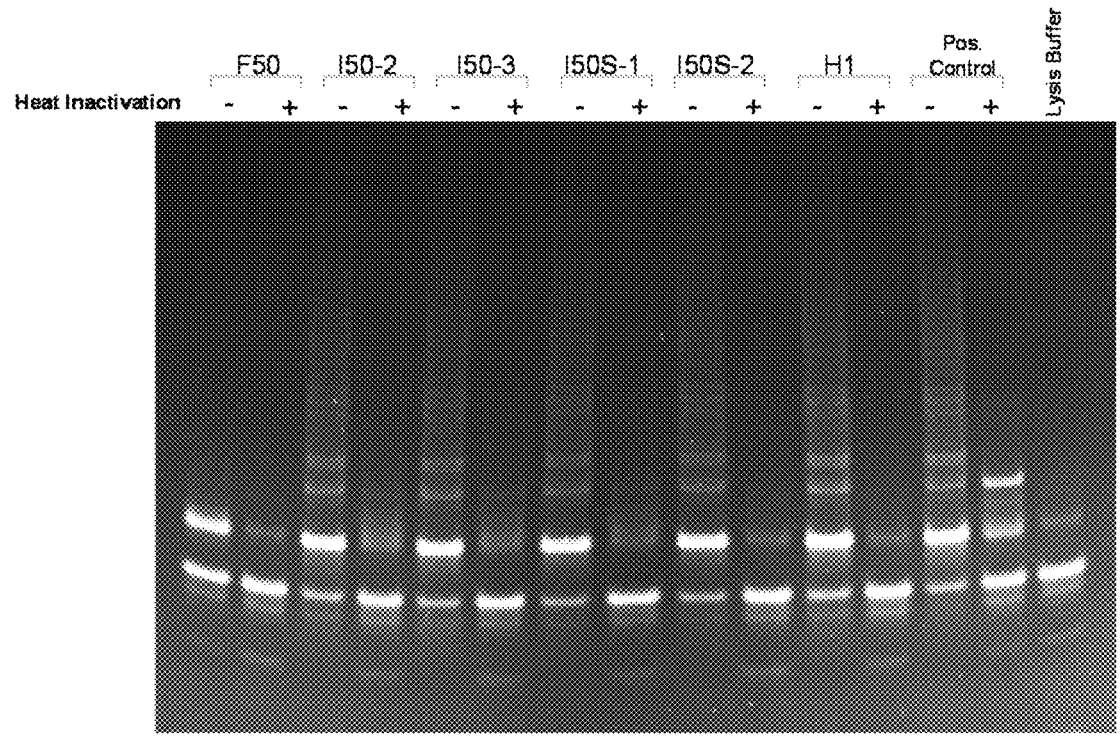
FIGS. 6A-6B show analyses of telomerase activity (FIG. 6A) and the length of telomeres (FIG. 6B) in low passage (F50) and senescent (F50S) parental fibroblasts, in iPSC lines derived from F50 (I50-2 and I50-3) and F50S (I50S-1 and I50S-2), and in human ESCs (H1). Telomerase activity was measured using the Trapeze Telomerase Detection Kit (Chemicon). Heat inactivation inhibits telomerase activity and was used to assess the background of the assay for each sample where indicated. Telomere lengths were determined by qPCR analysis.
Figure 6B:
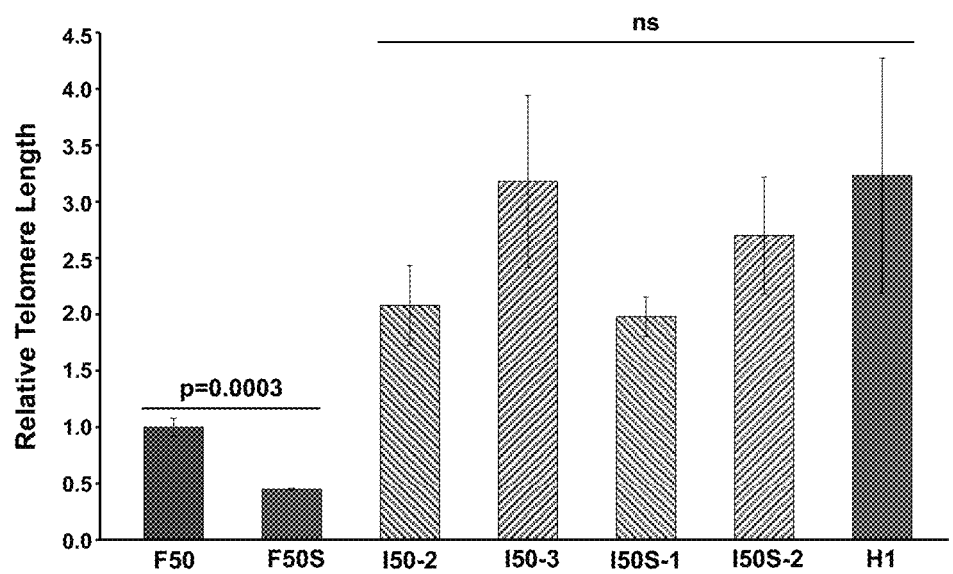
Figure 7:
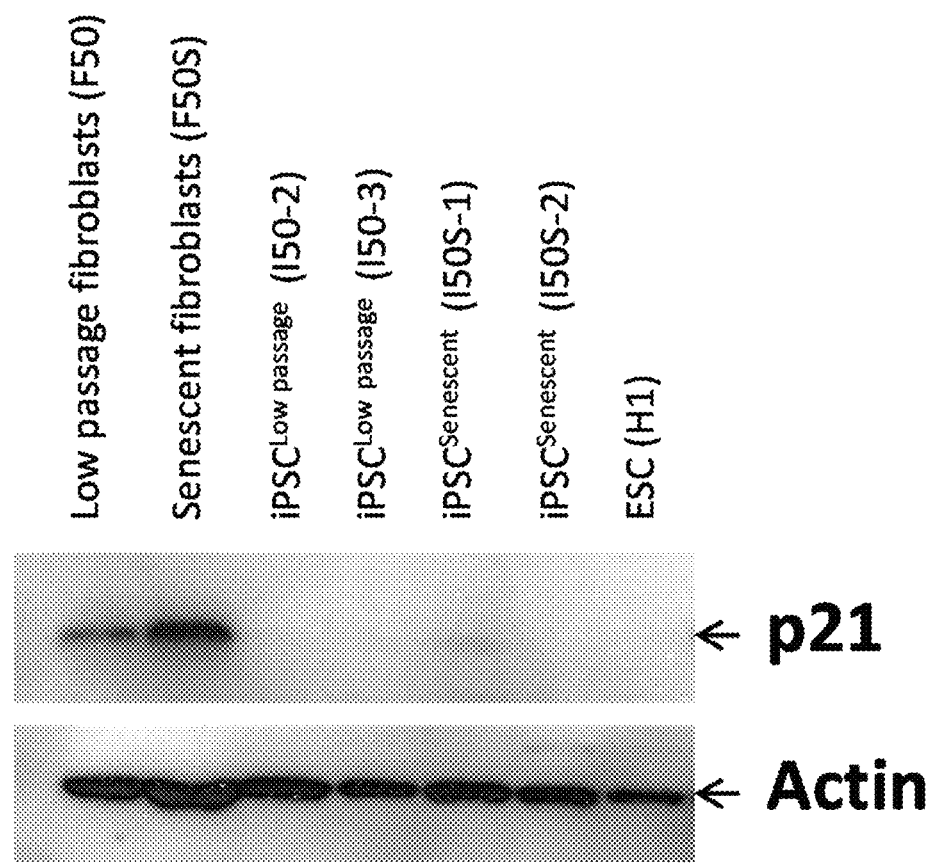
FIG. 7 is a Western blot showing the downregulation of senescence-associated protein p21 in iPSCs generated from senescent fibroblasts (F50S).

The adult fibroblast line derived from a 50 year old patient was serially passaged until more than 91% of cells exhibited a senescent phenotype. These cells were then reprogrammed into iPSCs according to the method described above. The reprogramming of this senescent line took only 16 days and resulted in an efficiency of approximately 0.33% (Table 6), which surpasses previous reports on the reprogramming of senescent fibroblasts using an integrating lentiviral approach (~40 days). Thus, as shown here for the first time, senescent human cells were reprogrammed with an integration-free approach. The iPSCs derived from senescent fibroblasts exhibited previously reported rejuvenation marks, such as the reactivation of telomerase, elongation of telomeres, and downregulation of p21 (FIGS. 6 and 7).

The activity of telomerase was measured using the Trapeze Telomerase Detection Kit (Chemicon). CHAPS (1×) lysis buffer was used to obtain extracts from parental fibroblasts (F50), iPSC lines derived from F50 (I50-2 and I50-3), iPSC lines derived from senescent F50S line (I50S-1 and I50S-2) and H1 ESC line. About 2000 cells were assayed for each telomeric repeat amplification protocol assay, and 800 cell equivalents were loaded into each well of a 15% non-denaturing TBE polyacrylamide gel. Reactions were performed in triplicate for each cell line. Each sample was heat inactivated for 15 min at 85° C. to assess the background of the assay. A 36-base internal control for amplification efficiency was run for each reaction. Data were analyzed with Fluoro Chem HD2 scanner. The assay showed that the telomerase activity was high in all iPSCs, including the lines generated from senescent fibroblasts, and ESCs but not in fibroblasts or upon heat inactivation of the samples (FIG. 6A).

The length of telomeres was determined by qPCR as previously shown in Cawthon, R. M., *Nucleic Acids Res,* 2002. 30(10): p. e47. Briefly, DNA was isolated from low passage (F50) and senescent (F50S) parental fibroblasts, iPSC lines derived from F50 (I50-2 and I50-3) and F50S (I50S-1 and I50S-2), and human ESCs (H1). qPCR analysis was performed with telomere-specific primers using Light-Cycle 480 (Roche). Telomeres were significantly longer in all iPSC lines as compared to corresponding parental fibroblasts, indicating an activation of rejuvenation processes upon reprogramming with approach described herein (FIG. 6B).

The expression of p21 was assessed in low passage fibroblasts (F50), senescent (F50S) derived from F50, iPSC lines derived from F50 (I50-2 and I50-3) and F50S (I50S-1 and I50S-2), and human ESCs (H1) using Western blot analysis. Briefly, the cells were lysed with RIPA buffer supplemented with a protease inhibitor cocktail (Sigma). Protein extracts were resolved by 15% SDS-PAGE and transferred to PVDF membranes. Membranes were blocked in 2.5% milk powder, 2.5% BSA in PBS for 1 hr and incubated with primary antibodies at 4° C. overnight. After washing with PBST (PBS with 0.1% Tween-20), membranes were incubated with secondary antibodies conjugated to horseradish peroxidase (HRP) for 2 hrs at room temperature. Signals were detected with a chemiluminescent substrate (Thermo Scientific). Antibodies used for detection were: rabbit anti-p21 (Santa Cruz Biotechnology), goat anti-β-actin (Santa Cruz Biotechnology), secondary anti-rabbit IgG-HRP (Santa Cruz Biotechnology), secondary anti-goat IgG-HRP (Santa Cruz Biotechnology). A representative image of the western blot analysis shows a high level of p21 expression in F50S fibroblasts, which is indicative of cellular senescence (FIG. 7). However, upon reprogramming of these senescent fibroblasts into iPSCs, the level of p21 reduced to almost undetectable, suggesting an activation of rejuvenation pathways in iPSCs.

The established iPSC lines generated from neonatal, adult and senescent human fibroblasts exhibited normal karyotypes and have been successfully maintained for at least 14 passages. The pluripotency of the generated iPSCs was confirmed by gene expression analysis, bisulfate sequencing and the differentiation into cell types of all three germ layers both in vitro and in vivo.

Figure 8:
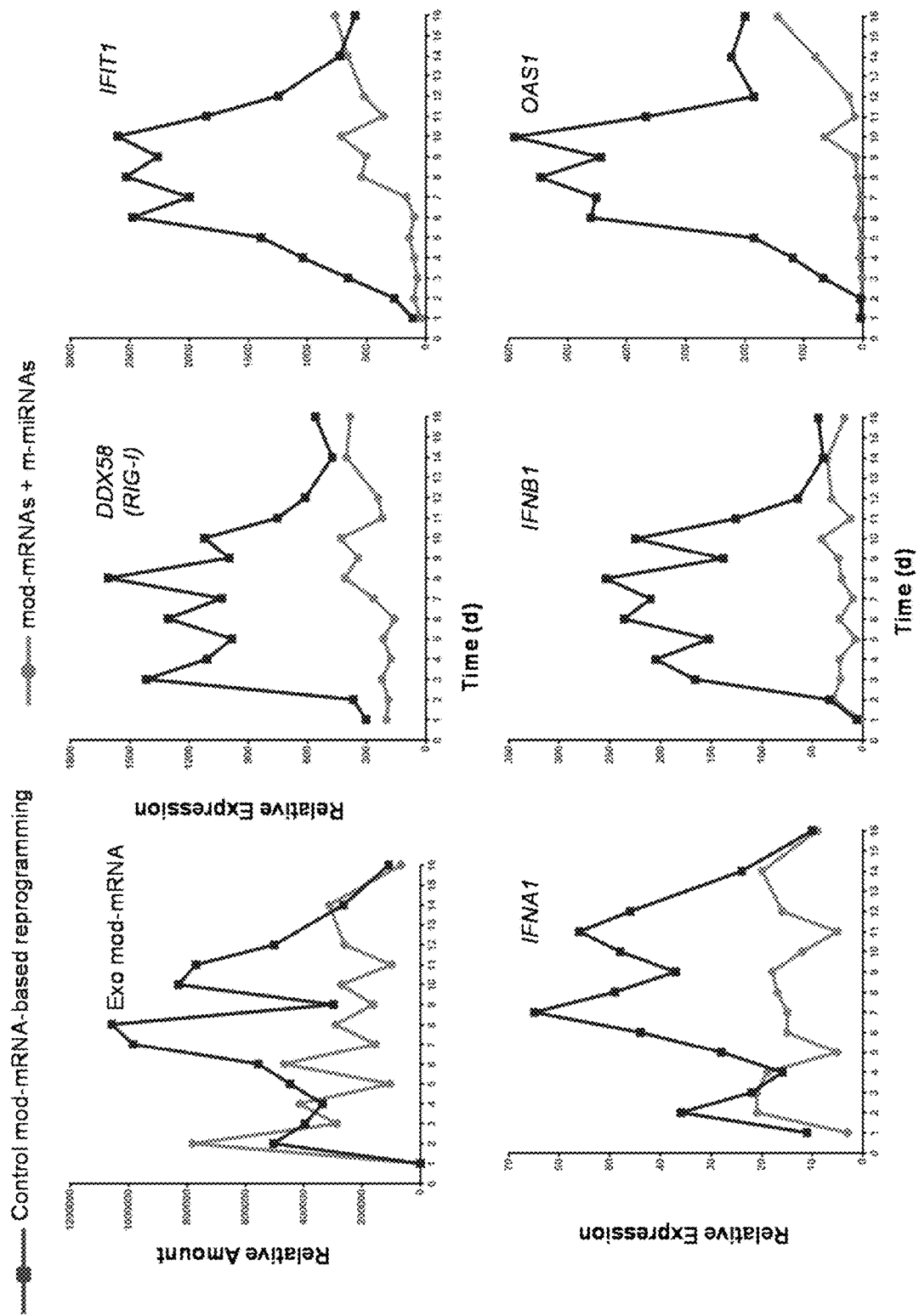
FIG. 8 is a series of charts showing a time point gene expression analysis of cells subjected to the combinatorial method disclosed herein (mod-mRNAs+m-miRNAs) relative to a previously-published feeder-free mod-mRNA reprogramming protocol (control mod-mRNA-based reprogramming) (Warren L, et al. *Sci Rep.* 2:657(2012)), using a probe-based Nanostring nCounter transcript quantification assay. The dynamics of activation of innate immunity-related genes, RIGI, IFIT1, IFNA1, IFNB1, and OAS1 are shown, as well as level of exogenous mod-mRNAs (exo-mod-mRNA).
Figure 9:
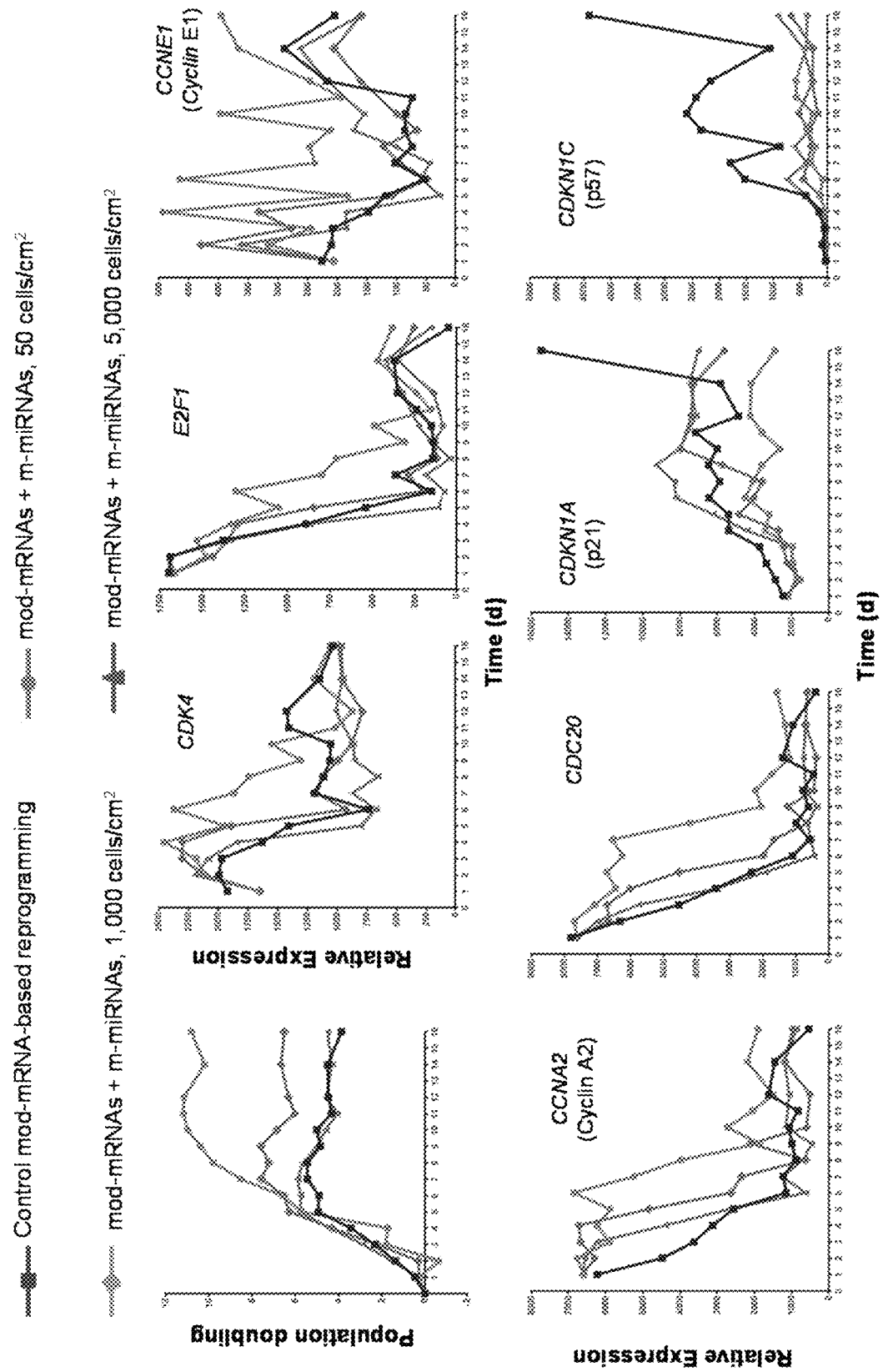
FIG. 9 is a series of charts showing a time point gene expression analysis of cells seeded at an initial density of 50 cells/cm$^2$, 1,000 cells/cm$^2$, or 5,000 cells/cm$^2$ (where indicated) undergoing a reprogramming with the disclosed combinatorial mod-mRNAs+m-miRNAs approach relative to a previously published mod-mRNA-based reprogramming protocol (control mod-mRNA-based reprogramming) using a probe-based Nanostring nCounter transcript quantification assay (nanostring.com). Population doublings of cells during the regiments, as well as the dynamics of activation of cell-cycle-related genes are shown.

Example 6: The Combinatorial RNA-Based Approach Reduces the Expression of Innate Immunity Genes, Leads to the Robust Activation of Pluripotency-Associated Genes and Exhibits Increased Cell Population Doubling A time-point experiment was performed and the transcript level of a set of genes was analyzed during the first sixteen days of the reprogramming method as described in Example 1 using human primary neonatal cells plated at an initial density of 500 cells per well of a 6-well plate, OPTI-MEM® at pH 8.2, 20 pmole m-miRNA mix, 600 ng of mod-mRNA mix, with 7 transfections, one every 48 hours. KOSR medium was changed 24 hours after each transfection. As compared to the previously published feeder-free mod-mRNA reprogramming protocol (Warren L, et al. *Sci Rep.* 2:657. (2012)), the level of transcripts encoding innate immunity genes was lower with the methods disclosed herein (see e.g., FIG. 8). This correlated with the lower level of exogenous reprogramming mod-mRNAs detected for our optimal regimen (FIG. 8). An elevated expression level of several cell cycle-promoting genes (e.g., CDK4, CCNE1, E2F1, CCNA2, and CDC20) and a reduced expression level of several cell cycle inhibitors (e.g., CDKN1A (p21) and CDKN1C (p57)) was also observed (FIG. 9). This level was similar for all conditions initiated at a low seeding density as compared to the reprogramming initiated from 10,000 and 50,000 cells. It is known that certain CDK inhibitors such as p21$^{CIP1}$ and p57 are activated in response to redundant signaling of reprogramming factors expression, thus creating a reprogramming barrier. The expression of both p21$^{CIP1}$ and p57 remains low in our regimen as compared to the basic mod-mRNA reprogramming protocol (FIG. 9).

Figure 10A:
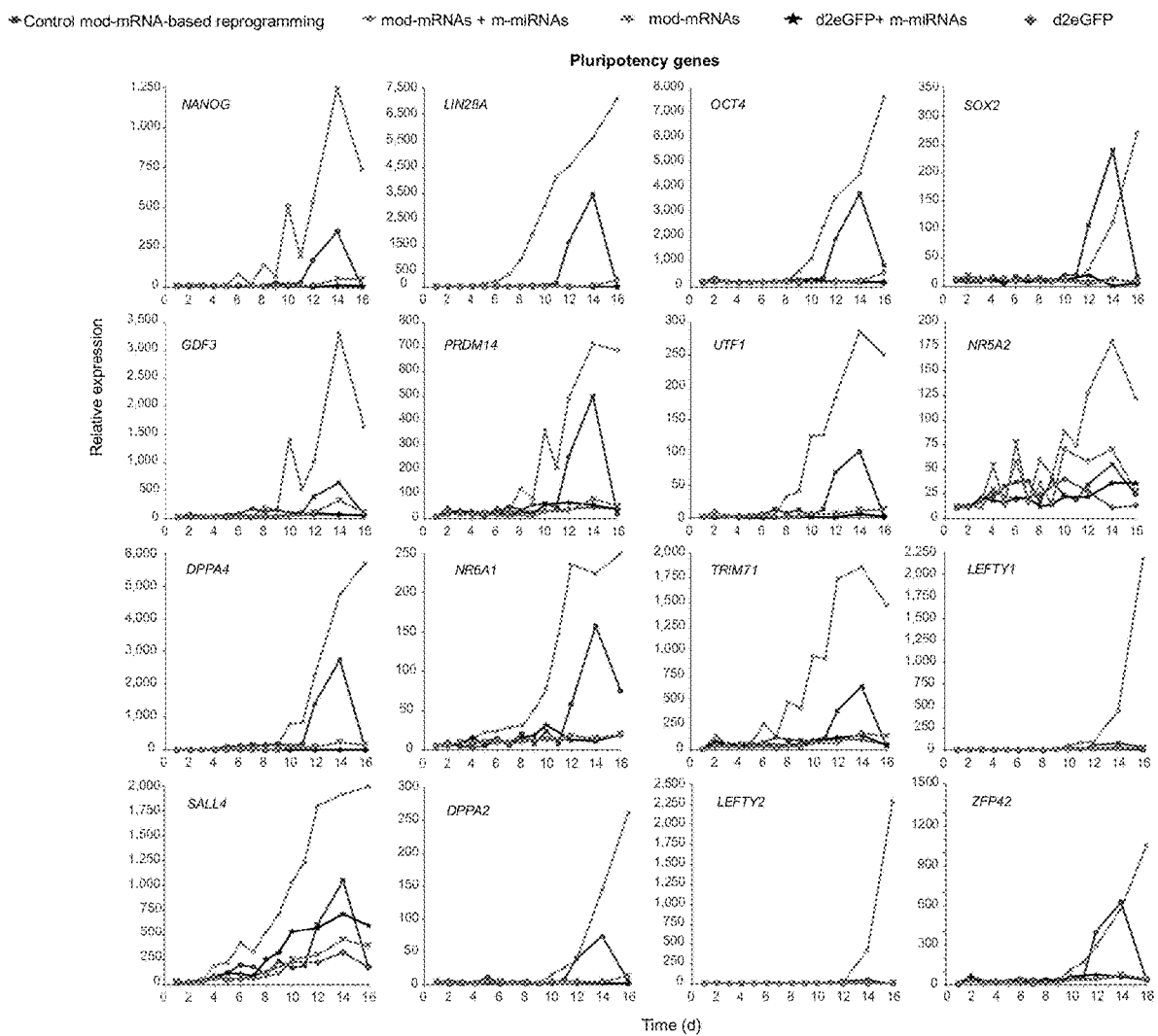
FIGS. 10A-10B are a series of charts showing a comparison of the activation of pluripotency genes (FIG. 10A) and chromatin modifiers (FIG. 10B) in cells exposed to a previously-published mod-mRNA-based reprogramming protocol (control mod-mRNA-based reprogramming), the disclosed combinatorial mod-mRNAs+m-miRNAs approach (mod-mRNAs+m-miRNAs), mod-mRNAs alone, m-miR-NAs supplemented with mRNA encoding d2eGFP as a transfection control (d2eGFP+m-miRNAs), and control mod-mRNA encoding d2eGFP only (d2eGFP) using a probe-based Nanostring nCounter transcript quantification assay.
Figure 10B:
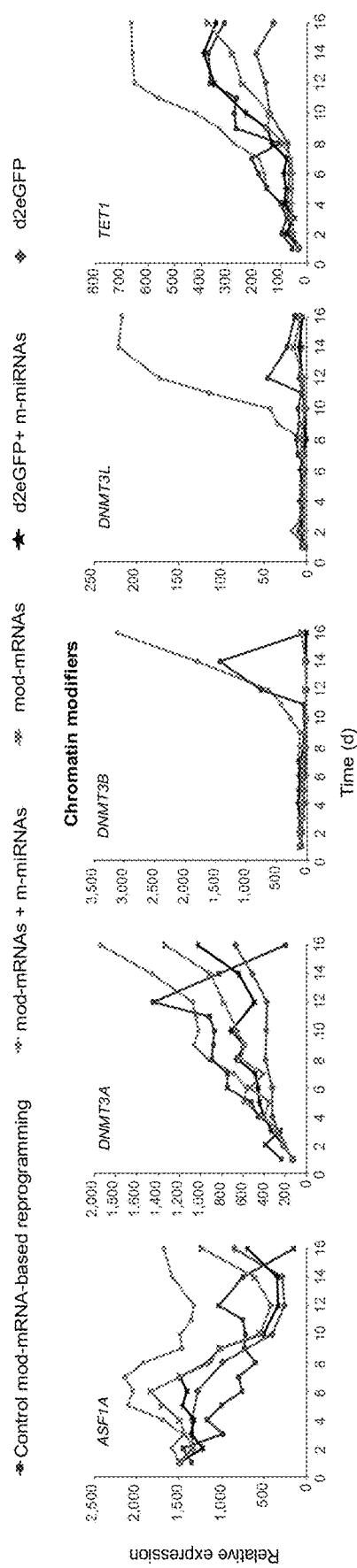
Figure 11:
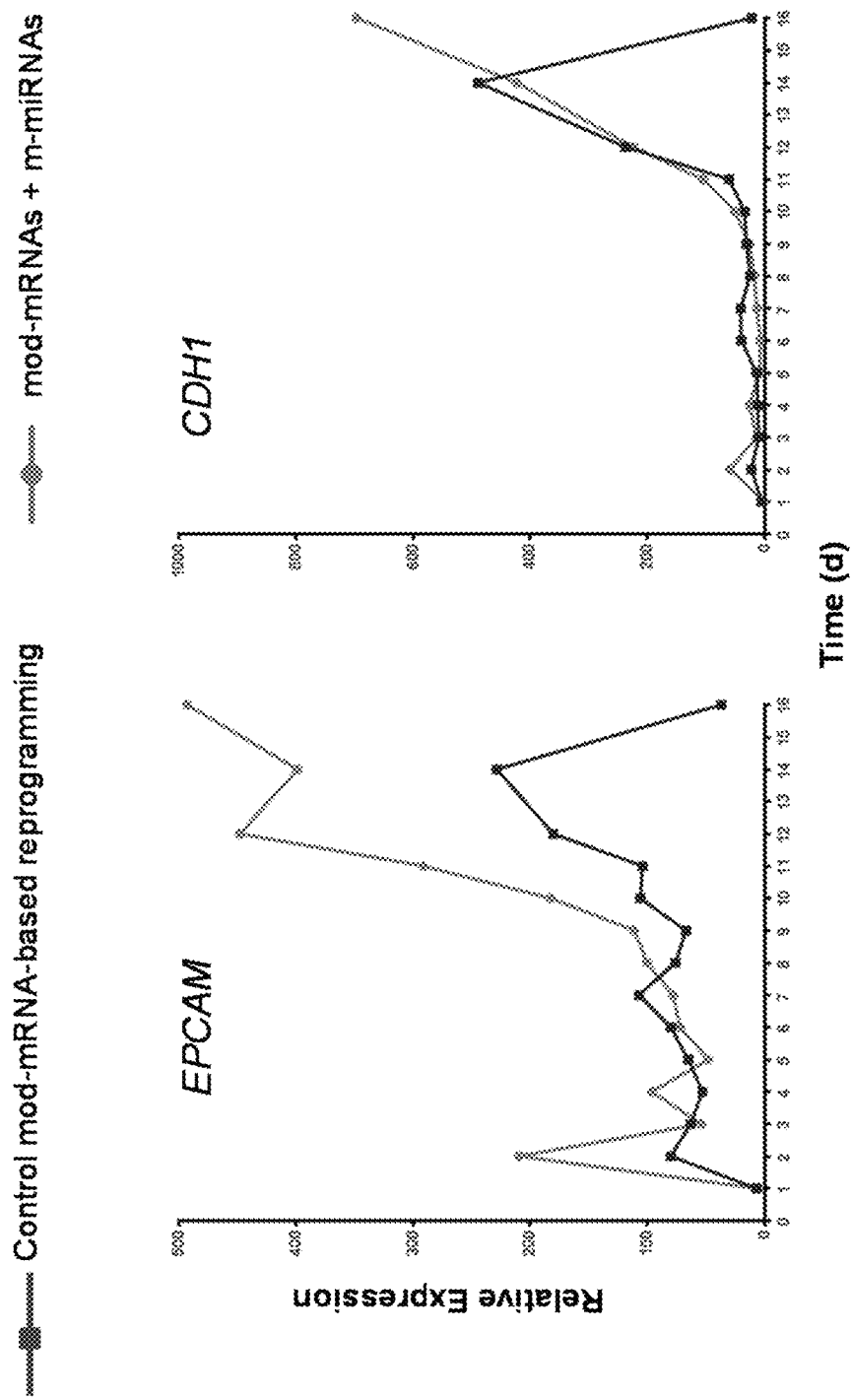
FIG. 11 is a series of charts showing a comparison of the activation of the mesenchymal-to-epithelial transition-related genes, EPCAM and CDH1, in cells undergoing reprogramming via the disclosed combinatorial mod-mRNAs+m-miRNAs method (mod-mRNAs+m-miRNAs) relative to a previously-published mod-mRNA-based reprogramming protocol (control mod-mRNA-based reprogramming) using a probe-based Nanostring nCounter transcript quantification assay.

The activation of known genes involved in chromatin remodeling, mesenchymal-to-epithelial transition (MET), and pluripotency maintenance with the particular focus on known predictive markers of pluripotency such as UTF1, Lin28A, DPPA2, and Sox2 was analyzed. A robust activation of several endogenous pluripotency genes (FIG. 10A) and chromatin modifiers (FIG. 10B) was observed, typically earlier and at higher levels than seen in prior art methods. For example, Lin28A was observed as early as Day 4, while in the basic mRNA reprogramming protocol of the prior art, Lin28A activation was observed only on Day 8-9 (FIG. 10A). Similarly, the transcript level of Sall4, increased on Day 3 of the present combinatorial protocol and only on Day 11 of the basic mod-mRNA reprogramming approach (data not shown). In addition, the activation of NANOG, LIN28A, OCT4, SALL4, GDF3, PRDM14, UTF1, NR5A2, DPPA2, DPPA4, NR6A1, TRIM71, LEFTY1, LEFTY2, ZFP42, ASF1A, DNMT3A, DNMT3B, DNMT3L, TET1, and EPCAM, occurred at least several days earlier in the combinatorial approach disclosed herein as compared to the previously published mod-mRNA reprogramming protocol (FIG. 10A). The activation of genes involved in mesenchymal-to-epithelial transition (MET) also exhibited robust activation (FIG. 11).

A day-by-day cell count revealed an increased cell population doubling rate using the reprogramming methods disclosed herein as compared to reprogramming methods known in the art. By Day 18, cell population doubling was about three-fold greater than other known methods (data not shown). This high rate of population doubling is likely caused by the lower cell toxicity due to low activation of innate immune response, as well as the lower initial starting cell density of the provided method (see FIGS. 8 and 9).

Example 7: Differentiation of iPSCs Generated by Methods Described Herein into a Neuronal Lineage The ability of iPSCs generated using our method to differentiate into a variety of cell types including cells from a neuronal lineage was assessed.

The iPSCs were differentiated into cells from a neuronal lineage using a protocol adapted from work by Hua et al. and Chambers et al. (Bao-Yang Hua, et al. *PNAS* 107:4335-4340 (2010); Chambers, S. M. et al. *Nature Biotechnology* 3:275-280 (2009)). Briefly, iPSC cultures were disaggregated using Collagenase Type I and feeder-depleted on gelatin for 30 min at 37° C. The non-adherent cells were collected and plated on a Geltrex (Gibco) covered dish at a density of 25-30,000 cells/cm$^2$ in N2/B27 Medium (as described by Liu et al. (*Biochem. Biophys. Res. Commun.* 346(1):131-139 (2006))) with 100 ng/ml bFGF (Gibco) and 10 uM Rock Inhibitor (Sigma). Rock Inhibitor was removed the next day, and cells were allowed to expand until 80% confluency. Cells were then disaggregated following the procedure described above using Collagenase I, and iPSC cell aggregates (embryoid bodies) were formed in suspension culture on low-attachment tissue culture plates in N2/B27 Medium supplemented with 250 ng/ml Noggin (R&D) and 10 μM SB431542 (Stemgent) for the initial 4 days of differentiation. The formed aggregates were induced with neural induction media containing Neurobasal medium (Gibco) supplemented with N2, B27 and heparin for 14 days. The induction phase was followed by the differentiation stage in Neurobasal medium supplemented with N2 (Gibco), B27 (Gibco), 1 ug/ml laminin (Sigma), 100 nM cAMP (Sigma), 200 ng/ml ascorbic acid (Sigma), 10 ng/ml BDNF (Peprotech), 10 ng/ml GDNF (Peprotech) and 10 ng/ml IGF-I (Peprotech). At Day 84 of differentiation, cells were fixed in 4% Formaldehyde for 15 min, treated with 0.2% Triton X in saponin solution for 5 min, and blocked with 10% BSA in PBS and 10% donkey normal serum in saponin solution for 1 hour. Cells were stained in blocking buffer at 4° C. overnight with an antibody raised against neuron specific type III β tubulin (TUJ1) (Covance) and then with Alexa Fluor 594—conjugated secondary antibody for 2 hrs at room temperature. Mounting media with DAPI was used to show nuclei. Images were acquired using a Nikon Eclipse 90i upright microscope with a 10× objective (100× magnification).

Figure 12:
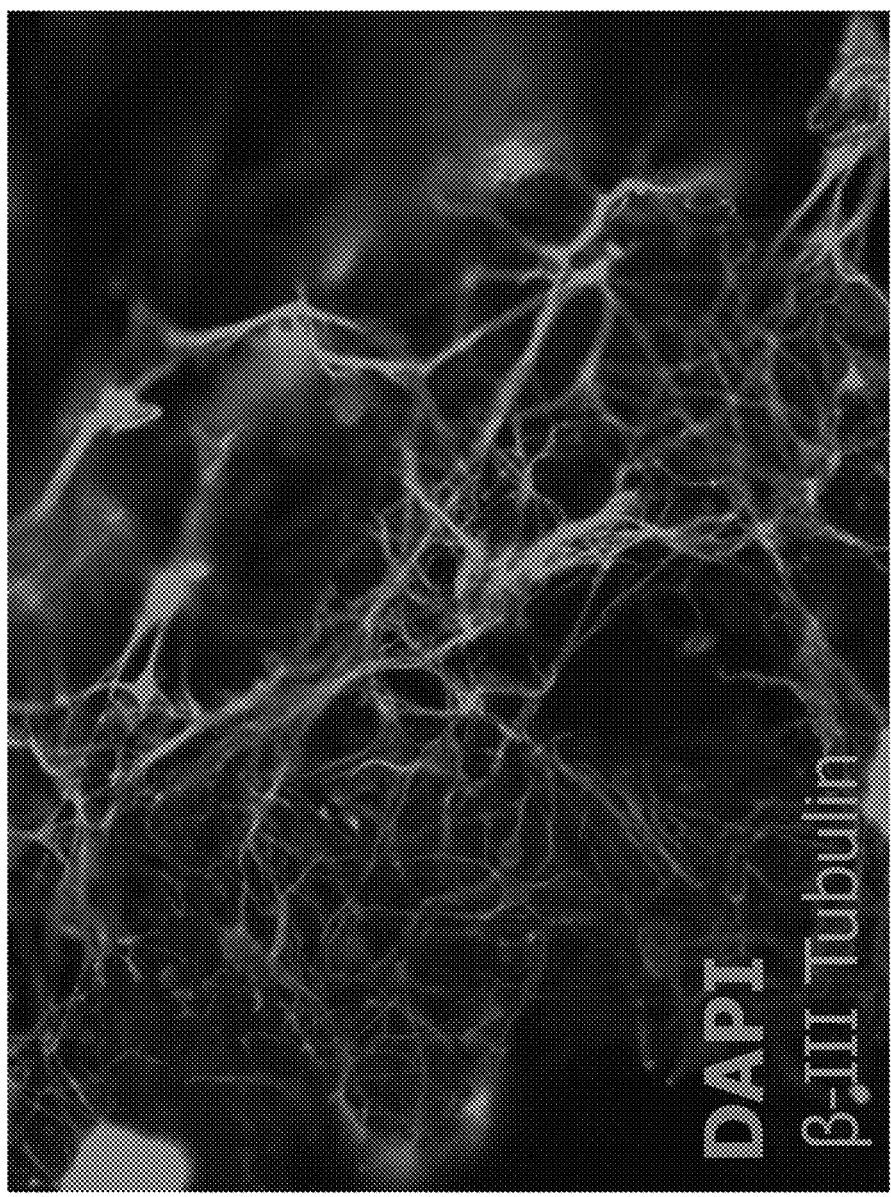
FIG. 12 is a micrograph showing neuronal lineage cells differentiated using a modification of previously published protocols from iPSCs generated using the methods described herein. Cells were stained with DAPI (blue) and the neuronal lineage marker β-III tubulin (red). The image was captured on Day 84 with a 10× objective (100× magnification).

The staining shows the presence of the neuron specific type III β tubulin (TUJ1), which is indicative of a successful differentiation of iPSCs into neuronal progenitors (FIG. 12).

Example 8: Differentiation of iPSCs Generated by Methods Described Herein into an Endodermal Lineage The ability of iPSCs generated using our method to differentiate into a variety of cell types including cells from an endodermal lineage was assessed.

The iPSCs were differentiated into cells from an endodermal lineage using a previously published protocol (Cheng, X., et al. *ESCs Stembook*, Cambridge (Mass.): Harvard Stem Cell Institute (2012)). Briefly, iPSCs were feeder-depleted and seeded on a Geltrex-covered dish. These cells were then differentiated as a monolayer at 70% confluency. For the first 4 days, RPMI medium (Gibco) supplemented with 1× Glutamine (Gibco), 450 µM MTG (Gibco), 2 uM CHIR 99021 (Stemgent), 100 ng/ml Activin A (R&D), 50 ug/ml Ascorbic Acid (Sigma), 25 ng/ml BMP4 (R&D), 5 ng/ml bFGF (Gibco) and 10 ng/ml VEGF (R&D) was used. On Day 5, cells were disaggregated with Accutase and seeded at 250,000 cells/well on a Geltrex (Gibco) coated dish. Cells were fed every 2 days, until Day 18 with media supplemented with cytokines provided above at varied concentrations. At Day 18 of differentiation, cells were replated onto Fibronectin coated chamber slides (BD) and immunostained with an antibody against endoderm specific cytokeratin Endo-A (Developmental Studies Hybridoma Bank, Iowa City, Iowa) using an immunostaining protocol as described for neuronal differentiation in Example 7. DAPI-containing mounting medium was used to visualize nuclei. Images were acquired using a Nikon Eclipse 90i upright microscope with a 10× objective (100× magnification).

Figure 13:
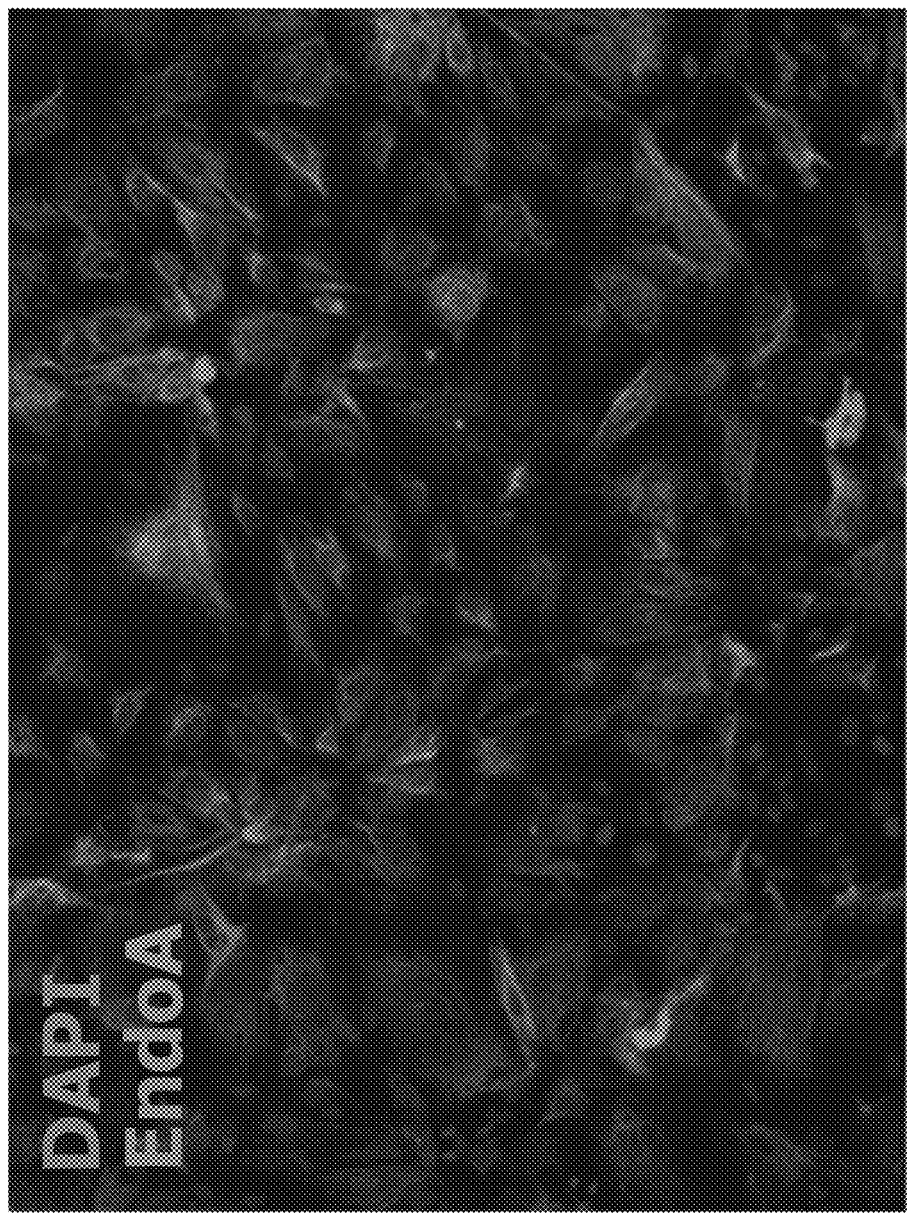
FIG. 13 is a micrograph showing endodermal lineage cells differentiated using a previously published protocol from iPSCs generated using the methods described herein. Cells were stained with DAPI (blue) and immunostained with an anti-Endo A (cytokeratin 8) antibody (red). The image was captured on Day 18 with a 10× objective (100× magnification).

The staining shows the presence of cells positive for endoderm specific cytokeratin Endo-A, which is an indication of a successful differentiation of iPSCs into an endodermal lineage. Endo-A is an early marker of endodermal progenitors, which in turn give rise to the epithelia of gastrointestinal and respiratory tracts, the urinary system, liver, and pancreas (FIG. 13).

Example 9: Differentiation of iPSCs Generated by Methods Described Herein into a Cardiomyocyte Lineage The ability of iPSCs generated using our method to differentiate into a variety of cell types including cells from a cardiomyocyte lineage was assessed.

The iPSCs were differentiated into cells from a cardiomyocyte lineage using a previously published protocol (Yang et al. *Nature*, 453:524-528 (2008)). Briefly, cells were feeder-depleted and seeded on a Geltrex covered dish. These cells were then dissociated using Collagenase Type I and placed in a suspension culture for embryoid body formation in differentiation medium as previously described by Yang et al. *Nature*, 453:524-528 (2008). The following cytokines were used in combination with StemPro medium (Gibco): Day 0: BMP4 (20 ng/ml) (R&D); Day1: Activin A (6 ng/ml) (R&D), BMP4 (20 ng/ml) (R&D), bFGF (2.5 ng/ml) (Gibco); Day 3 and Day5: VEGF (1.25 ng/ml) (R&D) and DKK1 (150 ng/ml) (R&D); Day 8, Day 11 and Day 14: VEGF (1.25 ng/ml), DKK1 (150 ng/ml), and bFGF (2.5 ng/ml).

Figure 14:
FIG. 14 is a micrograph showing cardiomyocyte lineage cells differentiated using a previously published protocol from iPSCs generated using the methods described herein. Cells were stained with DAPI (blue) and immunostained with an antibody against cardiac troponin T (cTNT) to confirm a commitment toward a cardiomyocyte lineage (red). The image was captured with a 10× objective (100× magnification).

Beating cardiomyocytes were observed after 14 days (not shown). The cells were immunostained with an antibody against cardiac troponin T (cTNT) and counterstained with DAPI to show nuclei using an immunostaining protocol as described for neuronal and endodermal lineages above. Images were acquired using a Nikon Eclipse 90i upright microscope with a 10× objective (100× magnification). The staining shows the presence of cells positive for cardiac troponin T (cTNT), which is indicative of successful differentiation of iPSCs into cardiomyocytes. CTNT is a marker of a cardiomyocyte lineage commitment (FIG. 14).

Example 10: Differentiation of iPSCs Generated by Methods Described Herein into Specific Skin Cell Types The ability of iPSCs generated using our method to differentiate into an ectodermal lineage, keratinocytes, mesenchymal stem cells, and fibroblasts was assessed.

Figure 15A:
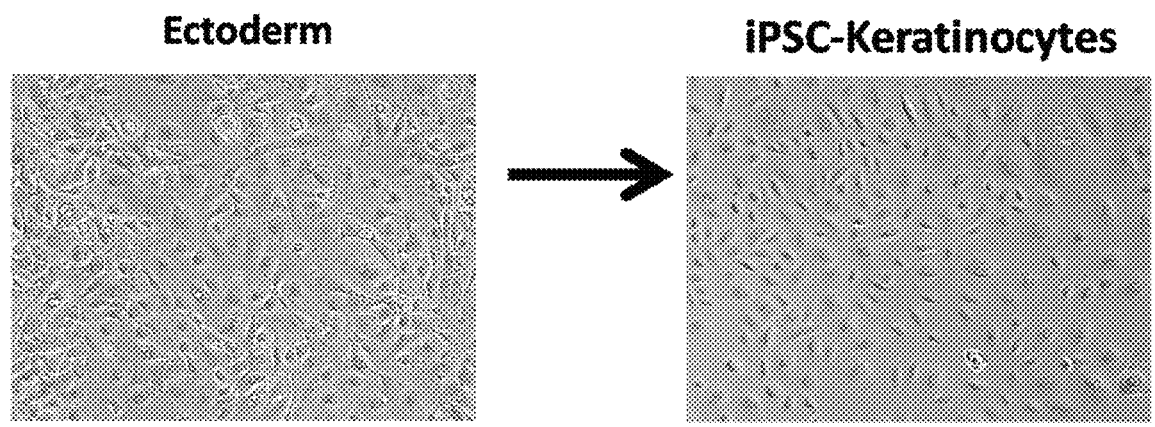
FIGS. 15A-15B illustrate a micrograph showing ectodermal lineage cells and keratinocytes (FIG. 15A) as well as mesenchymal stem cells and fibroblasts (FIG. 15B) differentiated using previously published protocols from iPSCs generated using the methods described herein. The images were captured with a 10× objective (100× magnification).

The iPSCs were differentiated into cells from an ectodermal lineage and then to keratinocytes using a previously published protocol using BMP4 and retinoic acid treatments (Bilousova G. et al. *J. Invest. Dermatol.* 131(4):857-64 (2011)). Briefly, iPSCs were plated in N2B27 medium supplemented with 100 ng/ml bFGF onto Geltrex and Collagen I (Sigma) covered tissue culture plates. The following day the medium was changed to the induction medium containing Defined Keratinocyte Serum Free medium (DKSFM) (Gibco) supplemented with 1 µM retinoic acid (Sigma) and 25 ng/ml BMP4 (R&D). The induction medium was replaced to DKSFM on Day 5 of differentiation. The medium was changed every other day for 17 days. On Day 18, the cells were replated onto Collagen type IV/Collagen type I coated dishes in CnT07 medium (Lonza) (FIG. 15A). The left panel shows cells at Day 10 of differentiation, which are morphologically similar to ectoderm. The right panel shows cells at Day 30 of differentiation, which look identical to normal human keratinocytes. The cells also stained positive for the marker of basal layer keratinocytes keratin 14 (1(14) with the immunostaining protocol as described in Example 7 (not shown). The images were taken with Nikon Eclipse TE2000-S inverted microscope with a 10× objective (100× magnification).

Figure 15B:
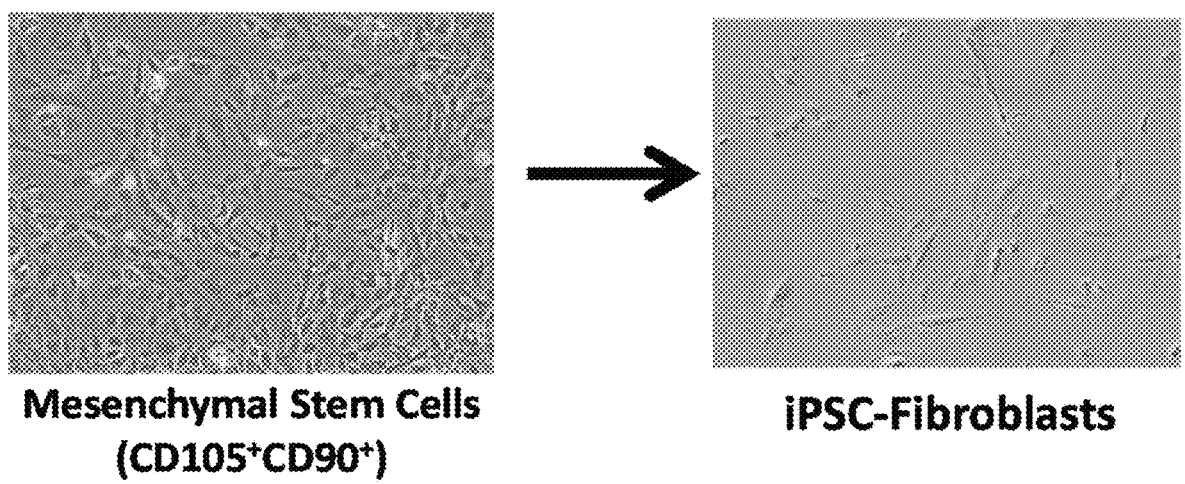
Figure 16A:
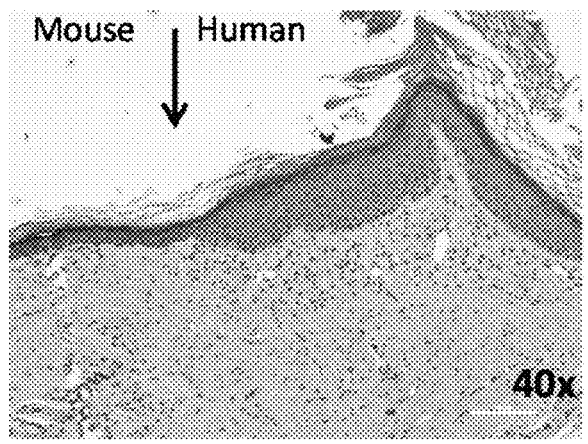
FIGS. 16A-16B illustrate a series of micrographs showing sections of a human skin graft on a SCID mouse.

The iPSCs can be differentiated either directly into a fibroblast lineage via exposure to TGF-β2 or BMP-4 in the presence of fetal serum or through the intermediate mesenchymal stem cell stage. The later approach allows for the assessment of iPSC capacity to differentiate into both mesenchymal stem cells and fibroblasts. The differentiation into mesenchymal stem cells was achieved using previously published protocols (West, J. D. et al. *Am. J. Physiol. Cell Physiol.* May 28 (2014); Lee, C. H. et al. *J. Clin Invest.* 120(9):3340-3349)). Specifically, iPSCs were exposed to medium containing 10% knock out serum replacement (GIBCO) in the presence of 10 ng/ml PDGF and 10 ng/ml EGF for 4 days. The medium was then switched to αMEM (HyClone) supplemented with 20% FBS. The cells were cultured for additional 2 weeks. The phenotype of iPSC derived mesenchymal stem cells was confirmed morphologically (FIG. 15B, left) and by flow cytometric analysis for the expression of mesenchymal stem cell markers CD105 and CD90 (not shown). For flow cytometry, the cells were incubated in PBS/10% BSA containing anti-CD105 and anti-CD90 antibody and then analyzed with Beckman Coulter Gallios cytometer. The results confirmed the successful differentiation of iPSCs into mesenchymal stem cell lineage. These iPSC-derived mesenchymal stem cells were then differentiated into a fibroblast lineage by exposing the cells to 100 ng/ml of connective tissue growth factor (CTGF). The fibroblast phenotype was confirmed by a morphological analysis (FIG. 15B, right) and functionally in the grafting assay described below and in FIGS. 16A-16B.

Images were taken with Nikon Eclipse TE2000-S microscope with a 10× objective (100× magnification).

Example 11: Use of Cells Differentiated from iPSCs to Form Human Skin

The ability to use cells differentiated from iPSCs generated using our method to create organs was assessed using human skin as a model system. A similar approach can be used for other organs, including but not limited to liver, pancreas, neurons, bones, and cartilage.

Keratinocytes and fibroblasts generated from iPSCs as described in Example 10 were used to create skin using a method adapted from Lichti et al. (Lichti, et al. *Nat Protoc.* 3(5):799-810 (2008)). Briefly, keratinocytes and fibroblasts derived from human iPSCs were mixed together and transplanted into a silicon chamber that was surgically inserted onto the muscle fascia of recipient severe combined immunodeficiency (SCID) mice. One week later, the chamber protecting the skin graft was removed.

Figure 16B:
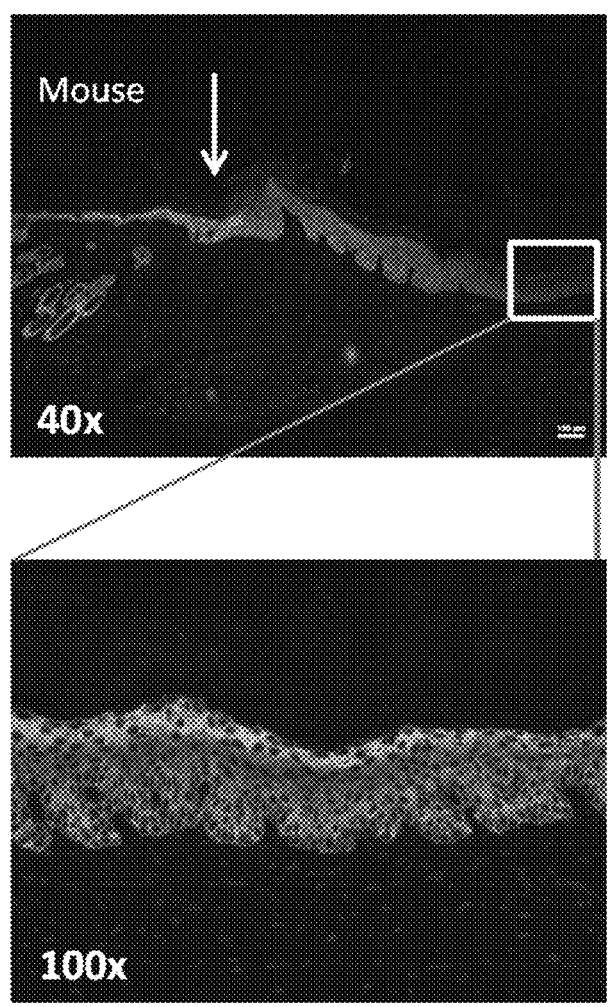

Four weeks post-transplantation, the recipient mice were euthanized and the grafting area was excised. The tissue was fixed in 10% Formalin, paraffinized, and sectioned. The sections were either stained with hematoxylin/eosin (H&E) or with antibody against epidermal specific markers Keratin (K) 14 and K1. For immunostaining, slides containing paraffin embedded sections were deparaffinized by submerging in Xylene and then rehydrated through a gradient ethanol bath. To retrieve the antigen, the sections were boiled for 10 minutes in 10 mM Citrate Buffer pH 6.0 (Abcam). Primary K14 and K1 antibodies were diluted in 10% BSA (Sigma) and 1% Goat Serum (Jackson), applied to the section and left overnight at 4° C. Note that two different K1 antibodies were used to discriminate between mouse and human skin. One reacts only with mouse epidermis, the other with human. The next day, secondary antibody staining was performed. Alexa Fluor 594-conjugated antibody was used for K14, and Alexa Fluor 488-conjugated antibody was used for K1 (FIG. 16B). The H&E image (FIG. 16A) shows the formation of human skin on a mouse. Note the thicker epidermis in the graft area which is indicative of human skin. FIG. 16B shows the results of immunostaining using antibodies to both mouse and human K14 and to only mouse K1. The area to the right of the white arrow where there is no staining with antibody to mouse K1 shows the human xenograft area. FIG. 16B lower panel shows immuno-staining using antibodies to both mouse and human K14 and human K1 of the portion of FIG. 16B upper panel indicated by the white box. The K1 staining in this image indicates the formation of correct skin layers in a human iPSC-derived xenograft. Images were acquired using a Nikon Eclipse 90i upright microscope with either 4×(40× magnification) or 10× (100× magnification) objective where indicated.

Example 12: Genetic Correction of Epidermolysis Bullosa Mutant Gene Using iPSCs The ability to use cells differentiated from iPSCs generated using our method to correct genetic mutations was shown using Epidermolysis bullosa (EBS) as a model system. Since the wild type allele of K14 is intact in EBS patients and the mutant K14 works as a dominant negative protein, the deletion of the mutant allele should ameliorate/correct the symptoms of EBS.

Figure 17A:
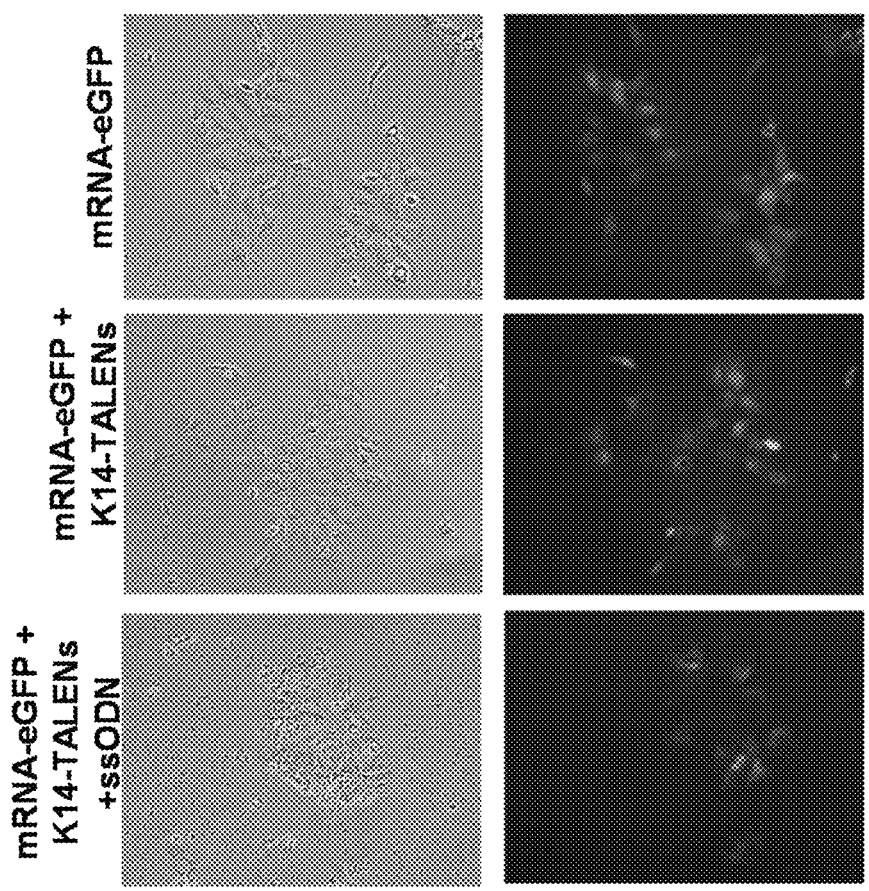
FIGS. 17A-17B are a series of micrographs and a schematic illustrating TALEN-mediated deletion of Exon 1 from the mutant K14 gene in Epidermolysis bullosa (EBS) iPSCs.
Figure 17B:
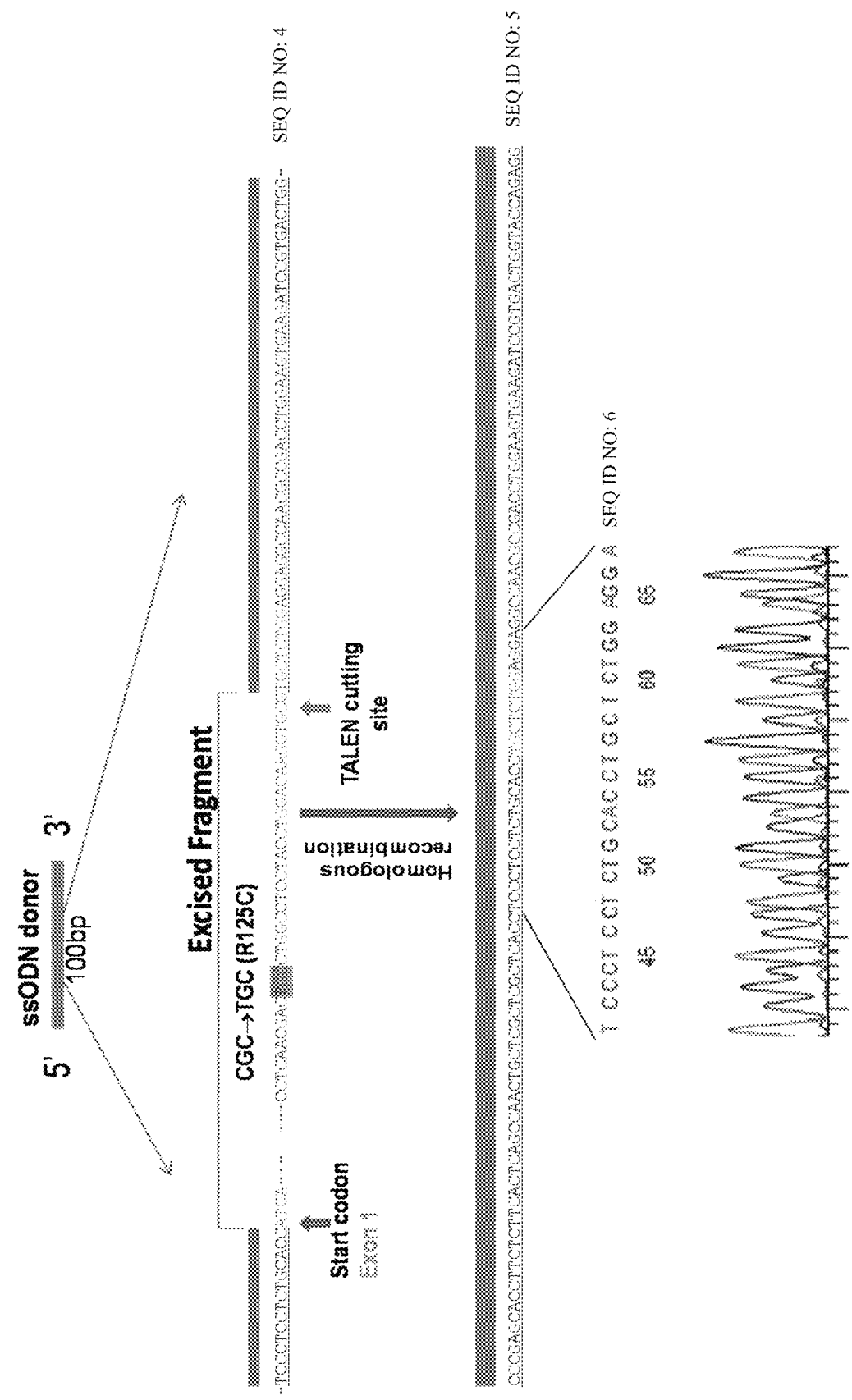

Cells from a patient suffering from EB were obtained using standard techniques, and used to generate iPSCs as described in Example 5. The iPSCs were then subjected to TALEN-mediated deletion of Exon 1 from the mutant K14 gene. To achieve the specific disruption of the mutant allele, we focused on a TALEN-based approach designed to introduce a knockout (KO) deletion of the $K14^{mt}$ allele, and to leave the wild-type K14 allele intact and functional. Since the TALE repeat array requires the presence of a T (thymine) at the 5' end of the sequence of interest, the point mutation C373T in the K1e allele in EBS iPSCs allows for the design of allele-specific TALENs, which would preferentially target the $K14^{mt}$ allele and could be used for all EBS patients with the C373T mutation. We have also designed a single-stranded oligonucleotide (ssODN) with the 5' half homologous to the sequence upstream of the ATG of Exon 1 (shown in blue in FIG. 17B), and the 3' half homologous to the sequence just distal to the TALENs cutting site (shown in red in FIG. 17B). The TALENs were delivered as mod-mRNA into target iPSCs. The efficiency of transfection of modified mRNA encoding eGFP, the K14 TALENs and ssODNs in EBS iPSCs is shown in FIG. 17A. The ssODNs were introduced using Fugene 6 (Roche), and 2 hrs later, 200 ng of TALEN mod-mRNA was delivered via RNAiMAX Lipofectamine (Invitrogen) in the presence of B18R, an interferon inhibitor to reduce the toxicity of mRNAs. Images were taken with Nikon Eclipse TE2000-S microscope with a 10× objective (100× magnification). DNA sequencing data (FIG. 17B) confirmed the excision of Exon 1 and its replacement with the ssDNA donor sequence only in the EBS iPSCs co-transfected with the K14 TALENs and ssODNs (FIG. 17A; lower panels). A similar experiment was performed on wild-type iPSCs with intact K14, and the designed TALENs did not target the wild-type K14 sequence in these iPSCs. The results confirm that iPSCs generated with the approach presented herein are suitable for genetic correction with currently available gene editing techniques.

Example 13: Combined Cellular Reprogramming and Gene Correction

A method is presented herein that combines a high-efficiency RNA-based reprogramming technology with gene editing to generate patient-specific induced pluripotent stem cells (iPSCs). Gene editing is mediated by Clustered Regularly Interspaced Short Palindromic Repeat (CRISPR)-associated (Cas9) nucleases, which are directed by short guide RNAs (gRNA) to induce a precise double-strand break (DSB) at endogenous genomic loci with high efficiency. The presence of exogenous donor DNA, carrying the correct gene sequence and sequences homologous to the region flanking the DSB, triggers homologous recombination (HR) and replacement of the defective sequence with the corrected one. Examples of homologous DNA donors include, but are not limited to, ssODN, double-stranded DNA or Recombinant Adeno-Associated virus. The absence of a homologous DNA donor results in the introduction of random mutations via non-homologous end-joining (NHEJ), which in many cases leads to a knockout of the allele.

For the combined method, CRISPR/Cas9-mediated gene editing was designed to be compatible with the optimized RNA-based reprogramming protocol described in detail elsewhere herein. Cas9 was cloned into a T7 RNA expression vector for in vitro production of modified mRNA encoding Cas9 (FIG. 18). To ensure mRNA stability and translation efficiency, the Cas9 open reading frame was ligated to the 3'-UTR of human beta globin, and a poly(A) tail was added into the template plasmid to avoid the additional polyadenylation step following in vitro transcription.

The transfection timeline for the combined gene editing and reprogramming is illustrated in FIG. 19. Fibroblasts were plated at a very low density on Laminin 521-coated dishes in HDF-Raw media. The next day, cells were transfected with modified Cas9 mRNA, following the transfection procedure as described for fibroblast reprogramming above. The ratio of Cas9mRNA, RNAiMAX and pH adjusted OPTIMEM was as described for the reprogramming protocol. Four hours following the Cas9 transfection, cells were transfected again with a guide RNA either with or without a repair template. Two days later, the reprogramming was performed as described in detail elsewhere herein.

Figure 20:
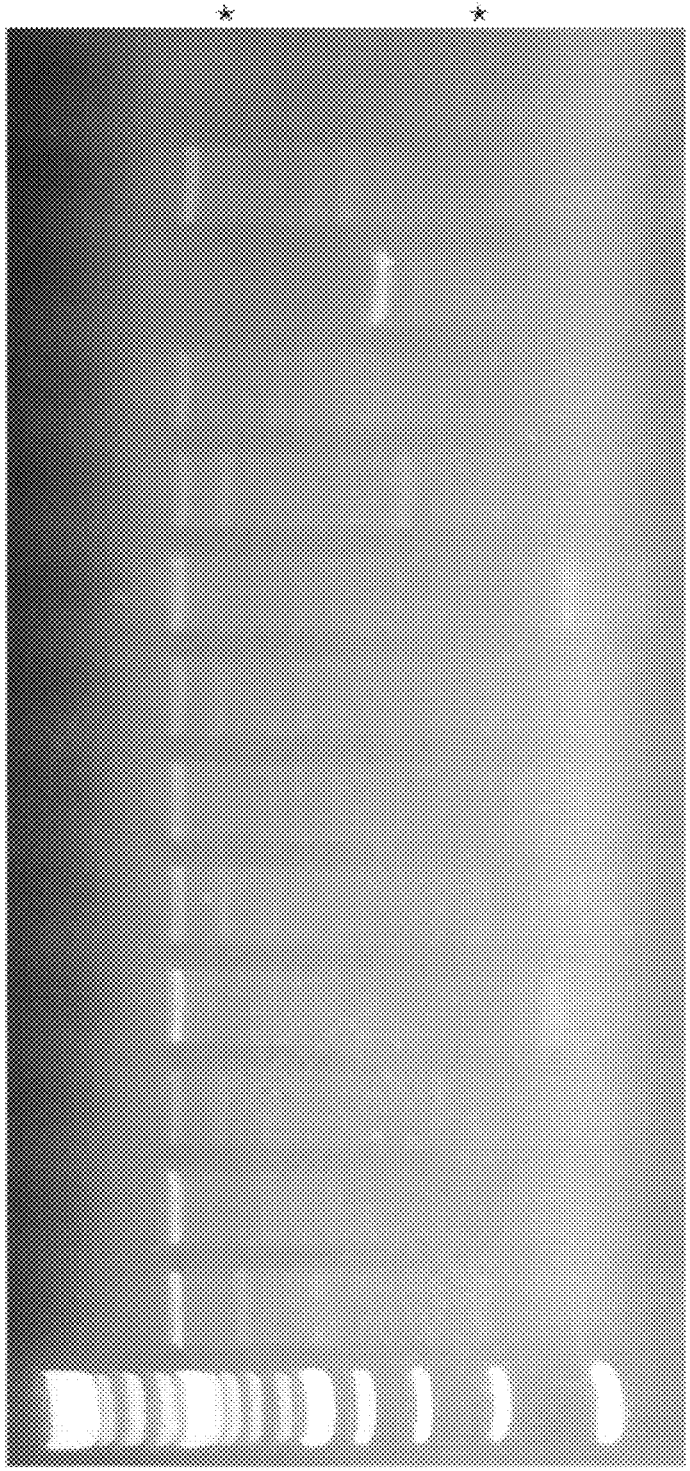
FIG. 20 illustrates optimization of Cas9 dosages and gRNA variants. Results of a T7 Endonuclease assay to determine Cas9 editing efficiency are shown. "−" denotes a standard gRNA, "mod" denotes gRNA made using modified nucleotides, "hifi" denotes gRNAs with a different scaffold sequence, and "-phos" denotes gRNA that is not treated with phosphatase.

To achieve maximum gene editing efficiency, various parameters of the gene editing portion of the protocol were optimized. First, Cas9 dosage and gRNA variants were optimized (FIG. 20). Experiments were performed in a 24-well format (1.9 cm$^2$). Two dosages of Cas9 modified mRNA were tested (100 ng and 300 ng). Additionally, several types of gRNA modifications were tested including modified nucleotides ("mod"), gRNAs having a different scaffold sequence, which may increase Cas9 specificity ("hifi"), and gRNA not treated with phosphatase ("-phos"), as well as standard, unmodified gRNA ("-"). All variants were tested on two different gRNAs, one targeting the top strand of DNA and the other targeting the bottom strand. A T7 Endonuclease assay was performed to determine Cas9 editing efficiency. Optimal results were achieved using the following conditions: 300 ng Cas9 mRNA and gRNA not treated with phosphatase that targets the bottom strand (FIG. 20).

Figure 22:
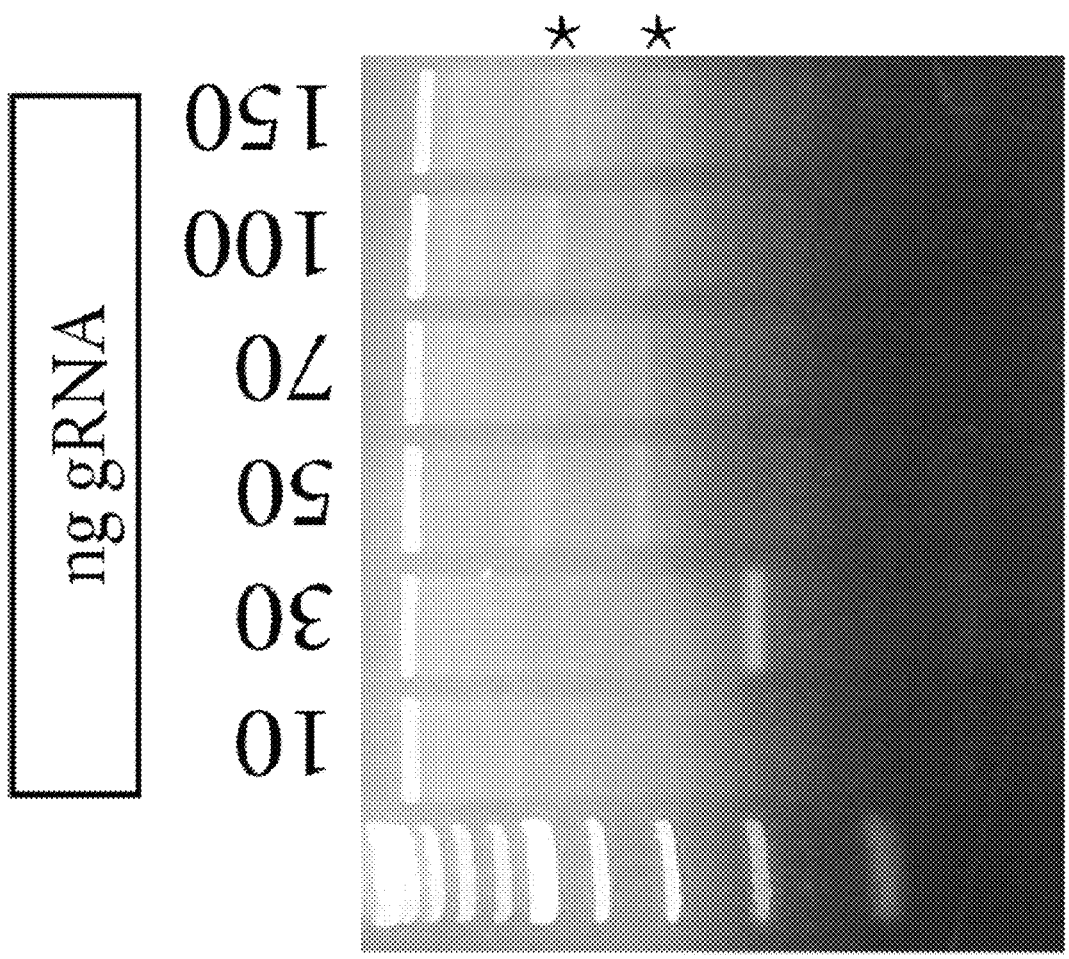
FIG. 22 illustrates optimization of transfection dosage. Different amounts of gRNA were co-transfected, from 10-150 ng. Results of a T7 Endonuclease assay to determine Cas9 editing efficiency are shown.
Figure 21:
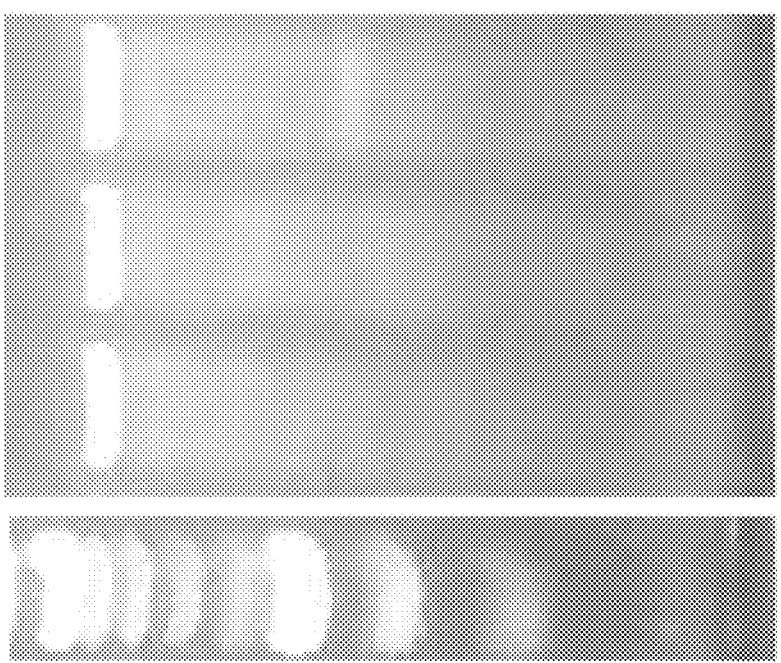
FIG. 21 illustrates optimization of gRNA transfection timing. Results of a T7 Endonuclease assay to determine Cas9 editing efficiency are shown. gRNA was transfected together with, 4 hours after, and 24 hours after Cas9 modified mRNA.
Figure 23:
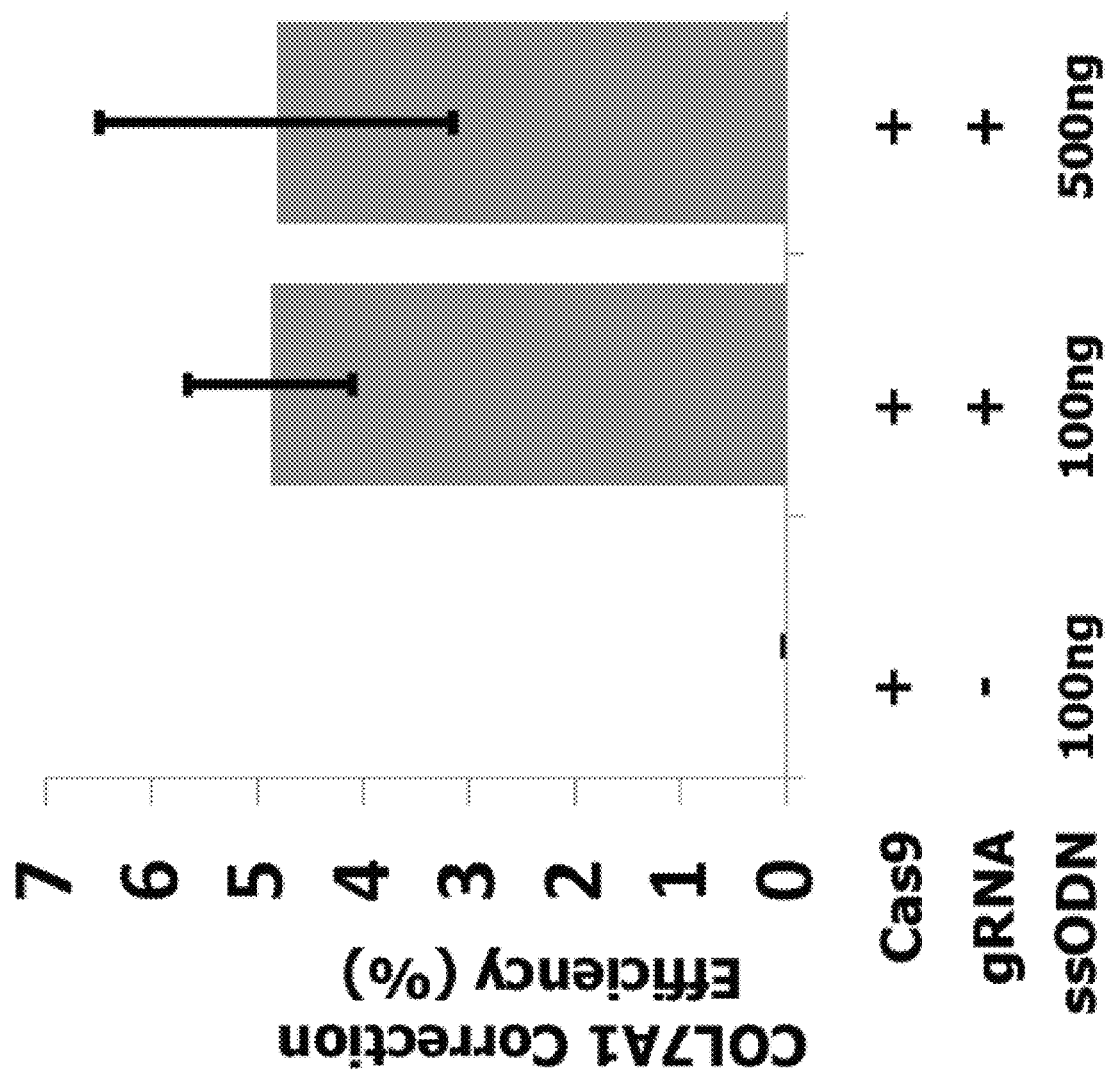
FIG. 23 illustrates optimization of ssODN transfection dosage. Experiments were performed in a 24-well format (1.9 cm$^2$). Different amounts of ssODN (100 ng, 500 ng) were co-transfected together with the gRNA. Homology directed repair was quantified using droplet digital PCR.

Timing of gRNA transfection was also optimized (FIG. 21). gRNA was transfected at the same time as the Cas9 modified mRNA, 4 hours after the Cas9 mRNA was transfected, or 24 hours after the Cas9 mRNA was transfected. Results of a T7 Endonuclease assay showed that the optimal results were achieved when the gRNA was transfected 4 hours after the Cas9 modified mRNA. In addition, gRNA transfection dosage was optimized (FIG. 22). Different amounts of gRNA, from 10-150 ng, were co-transfected. Results of a T7 Endonuclease assay to determine Cas9 editing efficiency showed that 100 ng gRNA was the optimal dosage. Optimization of the of the ssODN transfection dosage was also performed (FIG. 23). Different amounts of ssODN (100 ng, 500 ng) were co-transfected together with the gRNA. Homology directed repair was quantified using droplet digital PCR. Optimal results were achieved using 100 ng ssODN.

Figure 24A:
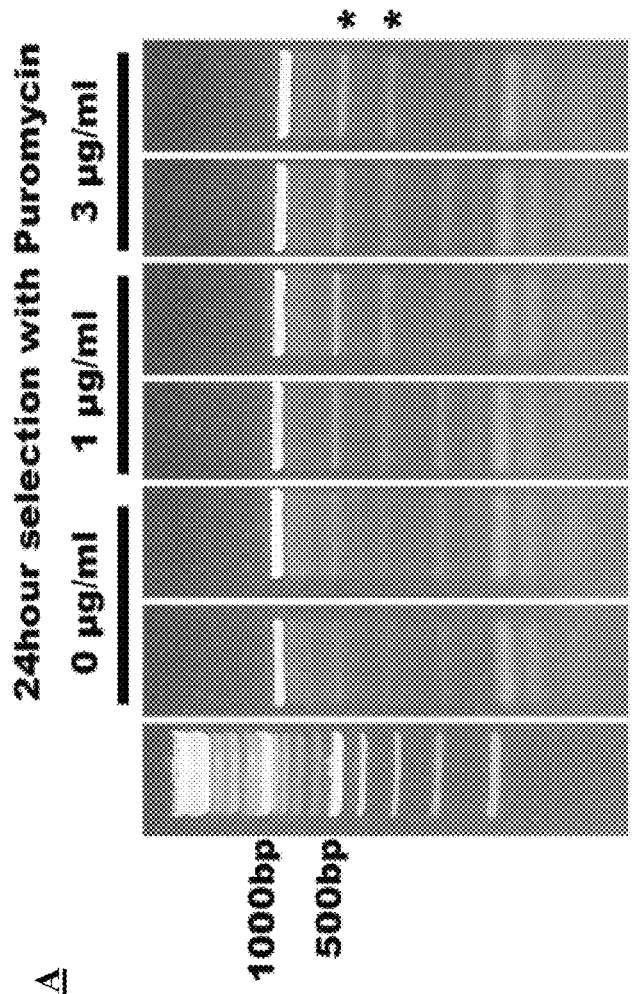
FIGS. 24A-24B illustrate the finding that addition of Puro$^R$ modified mRNA can be used for selection, which enhances Cas9 modification. Results of a T7 Endonuclease assay to determine Cas9 editing efficiency are shown.
Figure 24B:
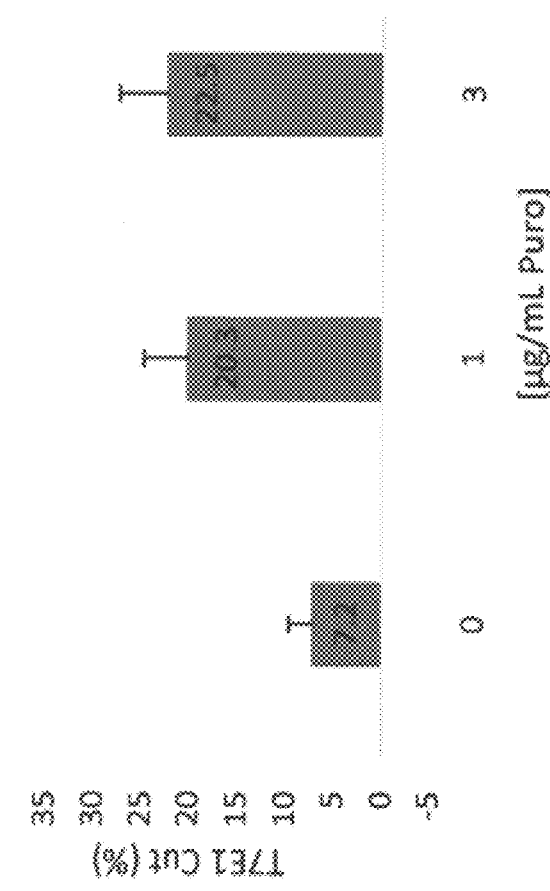

It was discovered herein that the addition of PURO® modified mRNA can be used for selection, which enhances Cas9 modification (FIGS. 24A-24B). PURO® modified mRNA was co-transfected with Cas9 modified mRNA. The following day, the transfected cells were treated with different concentrations of puromycin (0, 1, or 3 µg/ml) for 24 hours to look for increased Cas9 editing efficiency. Results of a T7 Endonuclease assay to determine Cas9 editing efficiency are shown in FIG. 24A and quantification of the assay using densitometry is shown in FIG. 24B. The optimal condition was determined to be 1 µg/ml Puro.

Figure 25A:
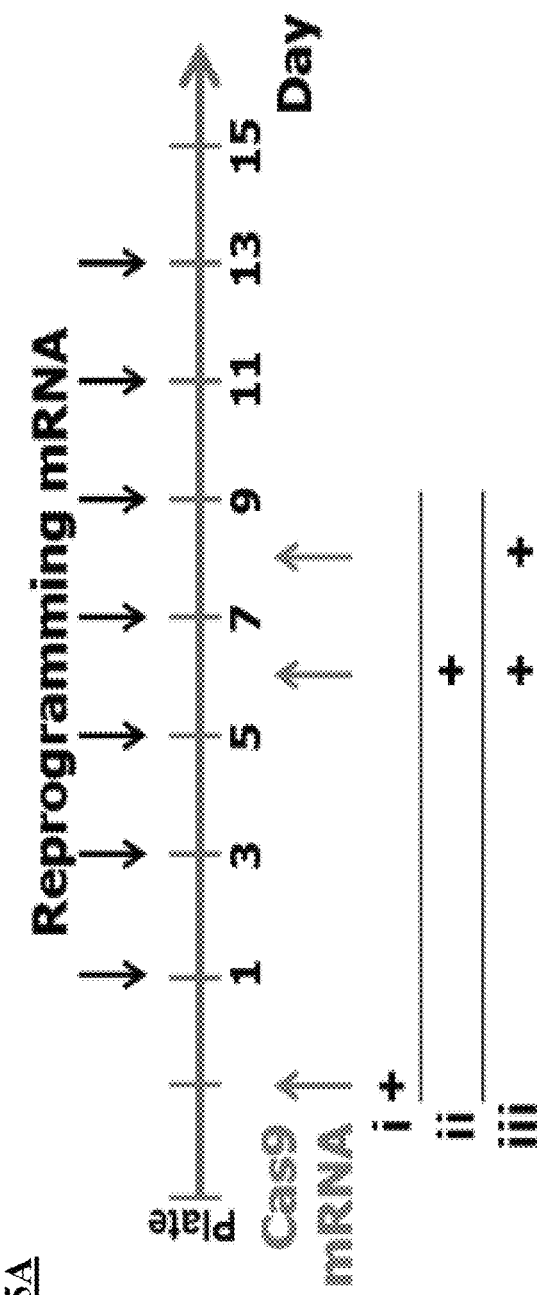
FIGS. 25A-25B illustrate optimization of Cas9/gRNA transfection timing during reprogramming. Experiments were performed in a 6-well format (9.5 cm$^2$).
Figure 25B:
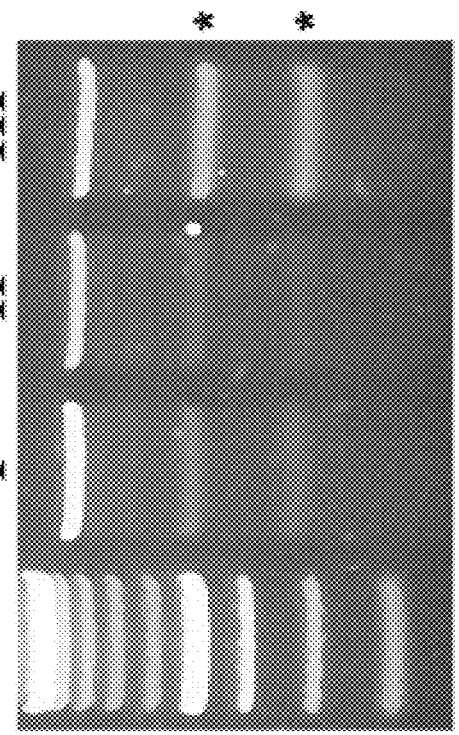

Optimization of Cas9/gRNA transfection timing during reprogramming was conducted (FIGS. 25A-25B). Experiments were performed in a 6-well format (9.5 cm$^2$). Cas9 was transfected either before, after the third, or after both the third and fourth reprogramming transfections (FIG. 24A). Resulting reprogrammed cells were collected after day 15 of reprogramming and tested for editing efficiency using a T7 Endonuclease assay. A single transfection of Cas9 modified mRNA before reprogramming was determined to be the optimal condition (FIG. 25B).

Figure 26:
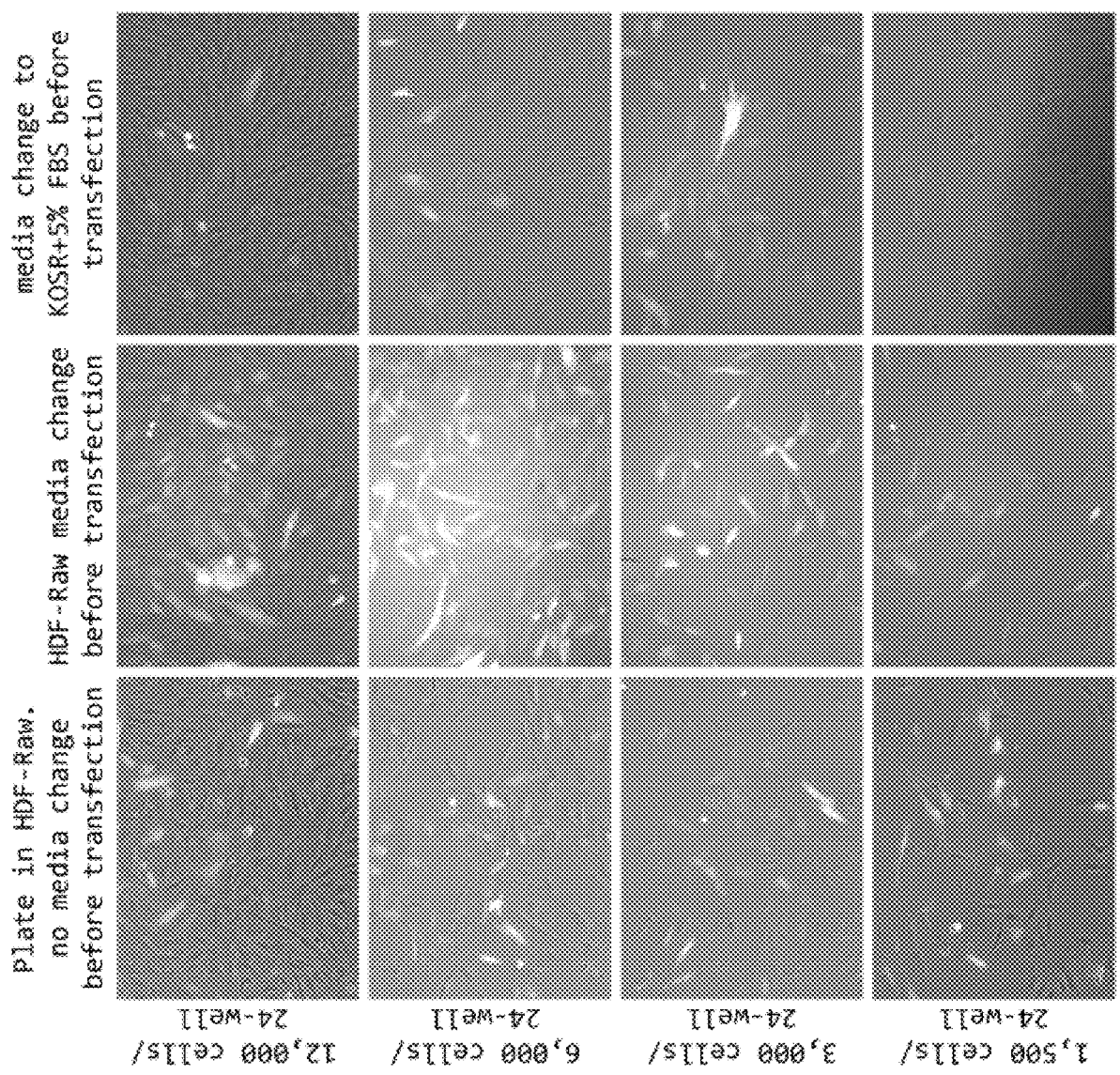
FIG. 26 illustrates optimization of cell culture media for transfection. Human patient-derived fibroblasts were plated in HDF-Raw media at concentrations of 1500, 3000, 6000, or 12000 cells into a 24-well (1.9 cm$^2$). Media was changed the following day to HDF-Raw, KOSR+5% FBS, or not changed at all. Clover and tdTomato modified mRNA was then transfected to directly visualize transfection efficiency by fluorescence.

Cell culture media composition was investigated for optimal transfection efficiency (FIG. 26). Human patient-derived fibroblasts were plated in HDF-Raw media at concentrations of 1500, 3000, 6000, or 12000 cells into a 24-well (1.9 cm$^2$). Media was changed the following day to HDF-Raw, KOSR+5% FBS, or not changed at all. Clover and tdTomato modified mRNA was then transfected to directly visualize transfection efficiency by fluorescence. The optimal condition was HDF-Raw media, changed before transfection, <3000 cells (1500 cells per cm$^2$).

Example 14: Combined Cellular Reprogramming and Gene Correction of RDEB Fibroblasts Using the combined gene editing and reprogramming approach outlined in FIG. 19, induced pluripotent stem cells were derived that were genetically modified and genetically clonal (FIG. 27). The patient had Recessive Dystrophic Epidermolysis Bullosa resulting from a homozygous mutation in COL7A1. The goal was to correct one or more alleles of COL7A1 to a wild type sequence. In this strategy, a single strand DNA oligo repair template was introduced together with Cas9 nuclease. As a result, the wild type sequence replaced the COL7A1 mutation during homology directed repair. The correction strategy of COL7A1 is summarized in FIG. 27A. Resulting colonies were clonally expanded and genetic modifications were confirmed by Sanger sequencing. Colonies were identified that were either unmodified (patient mutation remained), corrected by HDR, or had random insertion/deletion events.

A common strategy employed to prevent unwanted small insertions and deletions (INDELs) following correction is the addition of silent mutations that block Cas9/gRNA binding to DNA. To avoid further cutting by Cas9 following gene correction, a silent SNP was introduced into single-strand DNA donor (ssODN) to disrupt the PAM sequence following homology-driven repair, and a gRNA that spans the patient COL7A1$^{c.7485+G>A}$ mutation was designed (FIG. 28A). Following gene correction, the gRNA was unable to bind to the corrected allele, and thus prevented Cas9 from cutting the corrected allele. The gRNA and scaffold were also cloned into a plasmid for in vitro transcription from a T7 promoter. However, unlike Cas9 mRNA, gRNA was not synthesized with modified nucleotides.

To correct the COL7A1$^{c.7485\pm G>A}$ locus simultaneously with the reprogramming of RDEB fibroblasts, Cas9+gRNA was delivered together with a correcting ssODN 48 hours before initiating the reprogramming protocol (FIG. 28B). This regimen showed robust modification of the COL7A1 locus in cells harvested following reprogramming as assessed using a T7 endonuclease assay (41%, FIG. 28C). The final product following reprogramming consisted of a mix of iPSCs and incompletely-converted fibroblasts. In addition to ssODN, double-stranded DNA or Recombinant Adeno-Associated virus can be used a homologous DNA template to achieve specific correction.

Figure 29B:
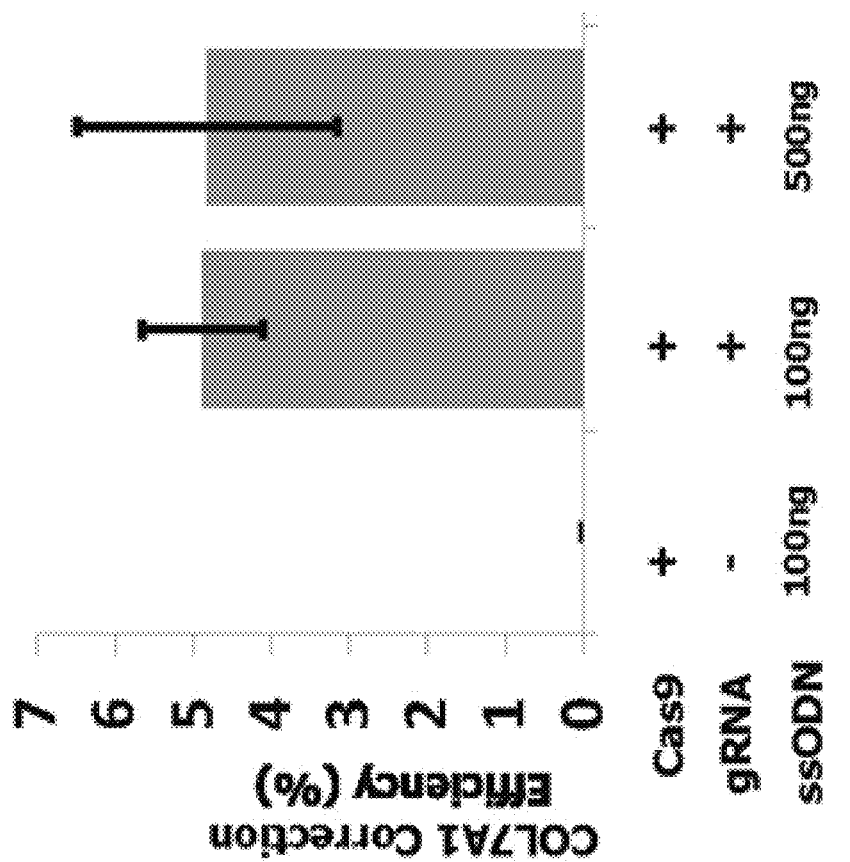
FIGS. 29A-29B illustrate Cas9-mediated correction of COL7A1$^{c.7485+5G>A}$. When COL7A1$^{c.7485\pm5G>A}$ correction was combined with reprogramming as described in FIG. 28B, a correction efficiency of approximately 5% was achieved. There was no improvement in correction with higher concentrations of ssODN (500 ng).
Figure 29A:
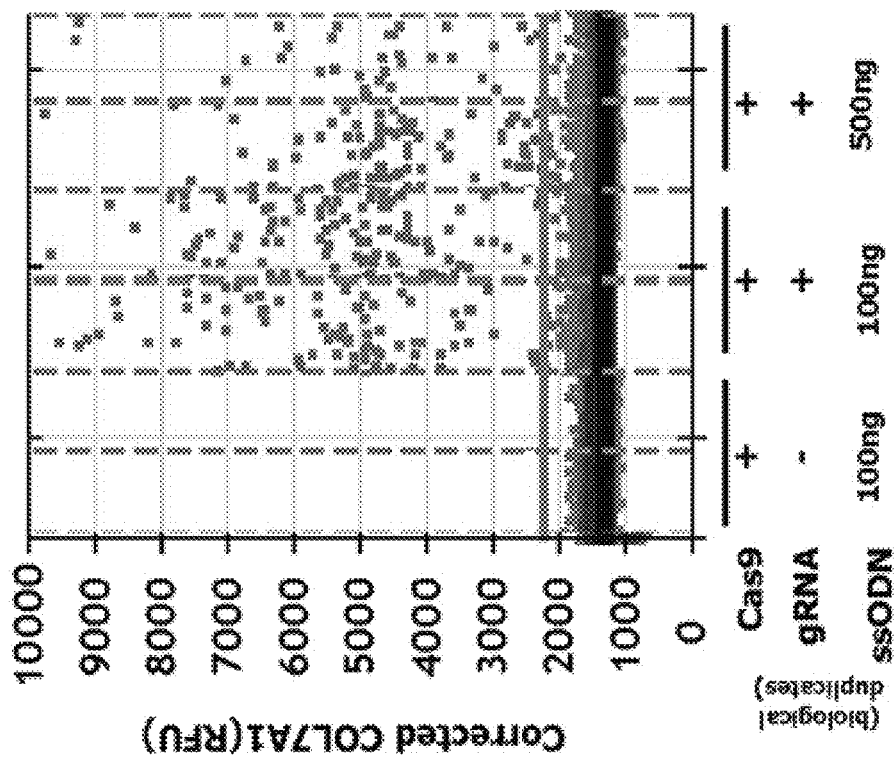

To quantify potentially rare genetic correction events, a digital droplet PCR platform was utilized. Briefly, a modified probe-based PCR assay was partitioned into nanoliter size reactions that were then individually quantified for fluorescence. This permitted the direct counting of the ratio of alleles containing single-nucleotide corrections. Using this technique, the efficiency of correction in the combined reprogramming and gene editing approach was calculated to be 5%. Thus, a robust set of conditions that yielded a correction efficiency of 5% of all alleles in RDEB fibroblasts (FIGS. 29A-29B) was identified.

Figure 30A:
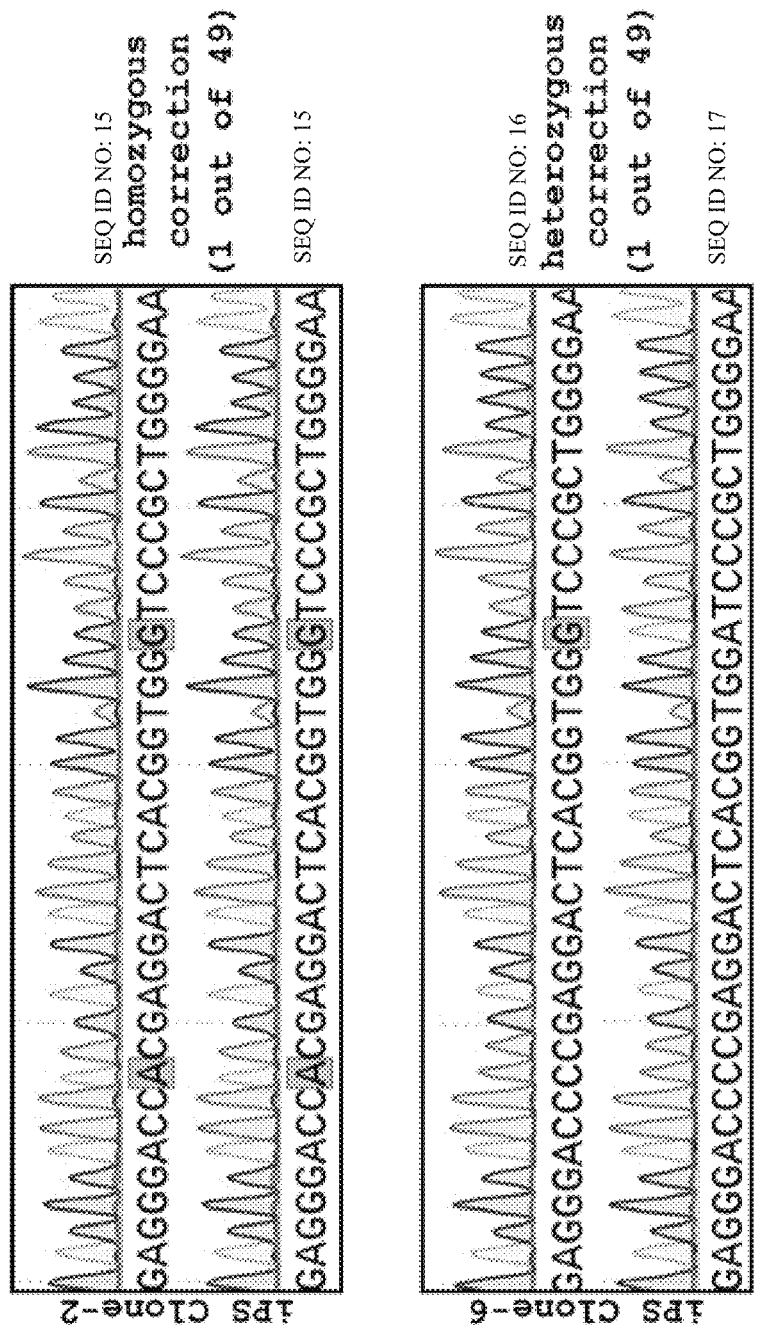
FIGS. 30A-30C illustrate successful simultaneous correction and reprogramming of RDEB fibroblasts with the COL7A1$^{c7485+5G>A}$ mutation.
Figure 30B:
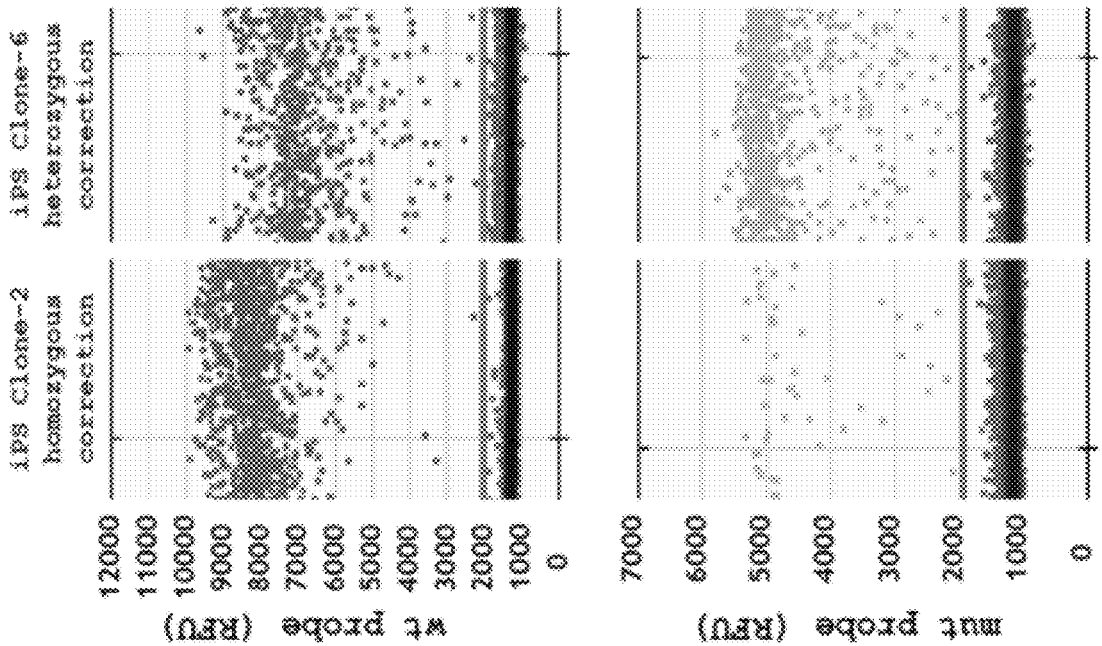
Figure 30C:
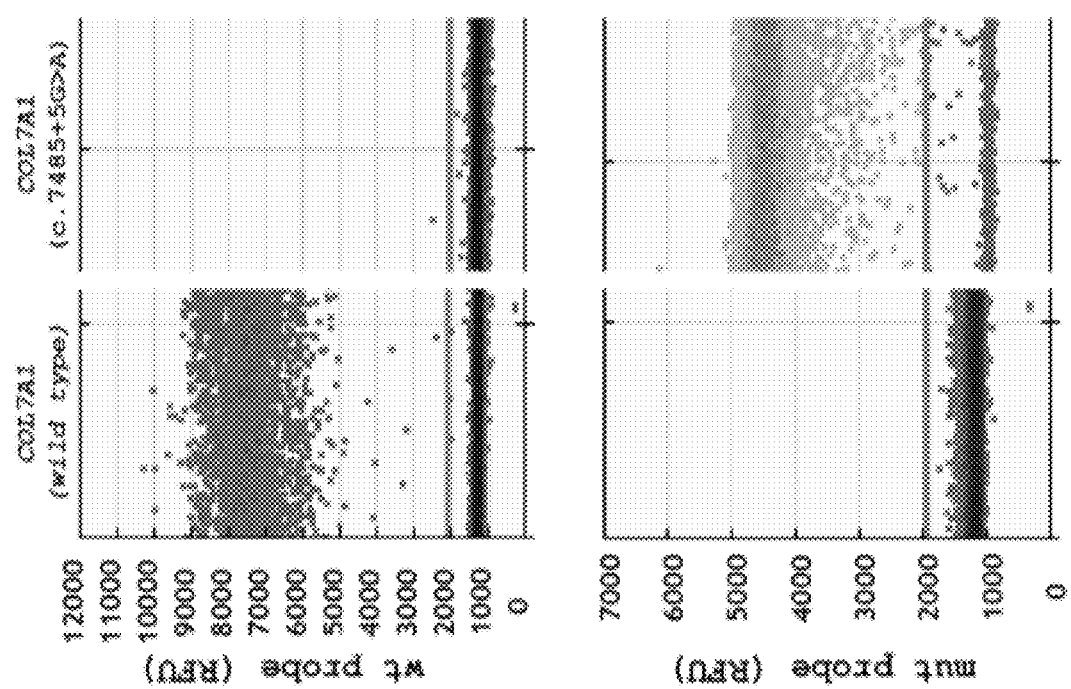

At the end of the reprogramming, 49 iPSC clones were picked from reprogrammed wells and 2 clones were identified with corrected mutant alleles: one of these clones had both mutant alleles corrected, while the other clone had one mutant allele corrected and the other intact (FIGS. 30A-30C). Given that patients who carry only one mutated COL7A1 allele do not show a RDEB phenotype, it was generally assumed that the correction of only one COL7A1 allele would be sufficient to restore functional levels of CoII protein. However, since both bi-allelic and mono-allelic correction of the COL7A1$^{c.7485+G>A}$ gene can be achieved with the method presented herein, it can be directly addressed if indeed a mono-allelic correction is sufficient to significantly ameliorate the RDEB phenotype upon transplantation.

Experiments were conducted to improve the efficiency of COL7A1$^{c.7485+G>A}$ correction. The manufacturing of COL7A1-corrected autologous iPSCs was simplified through the integration-free, feeder-free, vector-free, single clonal step high efficiency method described herein. Two parameters were critical for the success of this approach: high reprogramming efficiency and high targeting efficiency. As shown in FIGS. 28A-30C, an extremely high reprogramming efficiency and simultaneous correction of COL7A1$^{c.7485+G>A}$ fibroblasts was achieved.

Figure 31A:
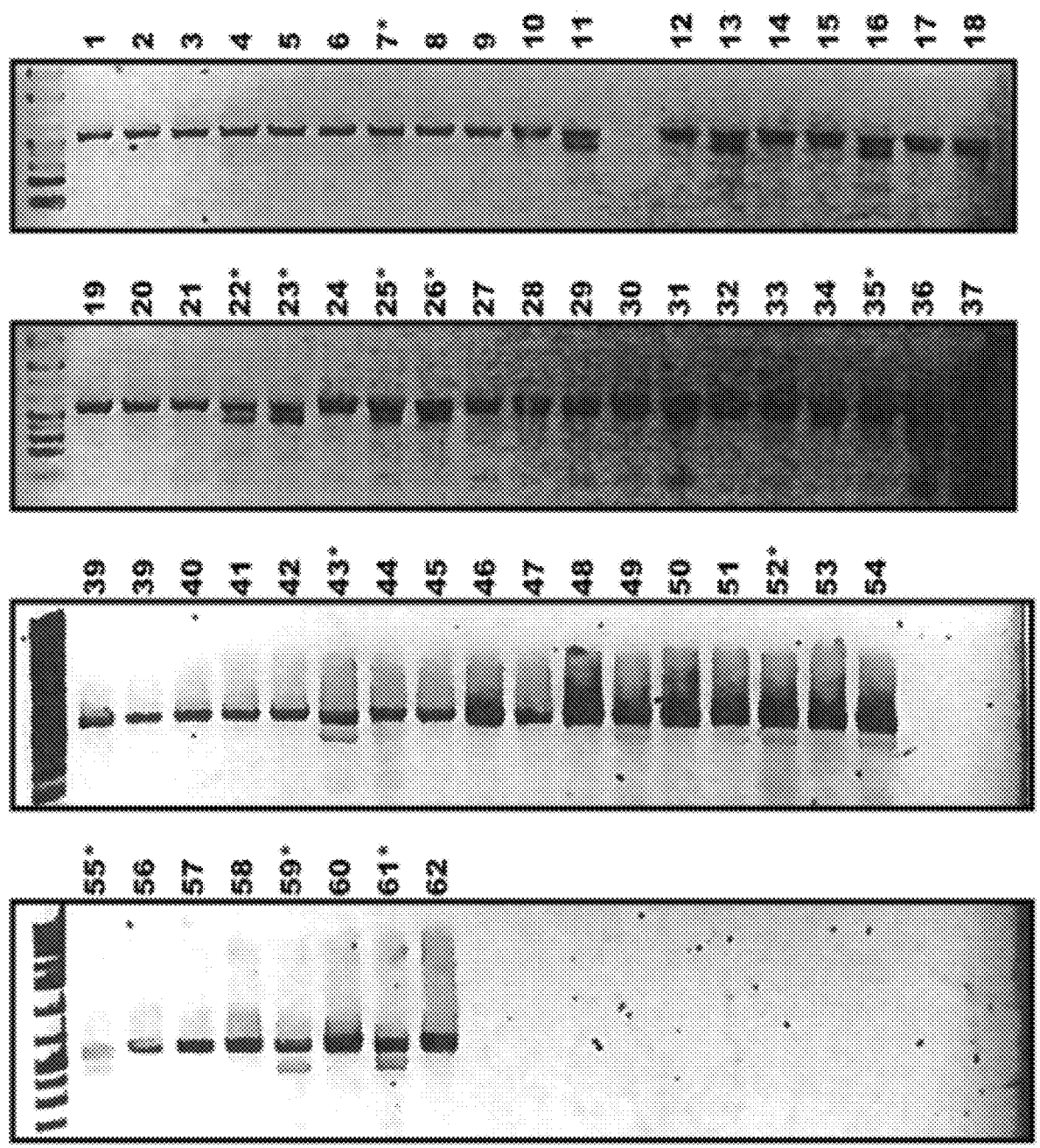
FIGS. 31A-31B illustrate combined gene editing and reprogramming of EBS patient derived fibroblasts. Using the combined gene editing and reprogramming approach outlined in FIG. 19, induced pluripotent stem cells were derived that were genetically modified and genetically clonal. The patient had the skin blistering disease Epidermolysis Bullosa simplex (EBS), resulting from a dominant-negative mutation in Keratin 14 (K14$^{c373C>T}$).
Figure 31B:
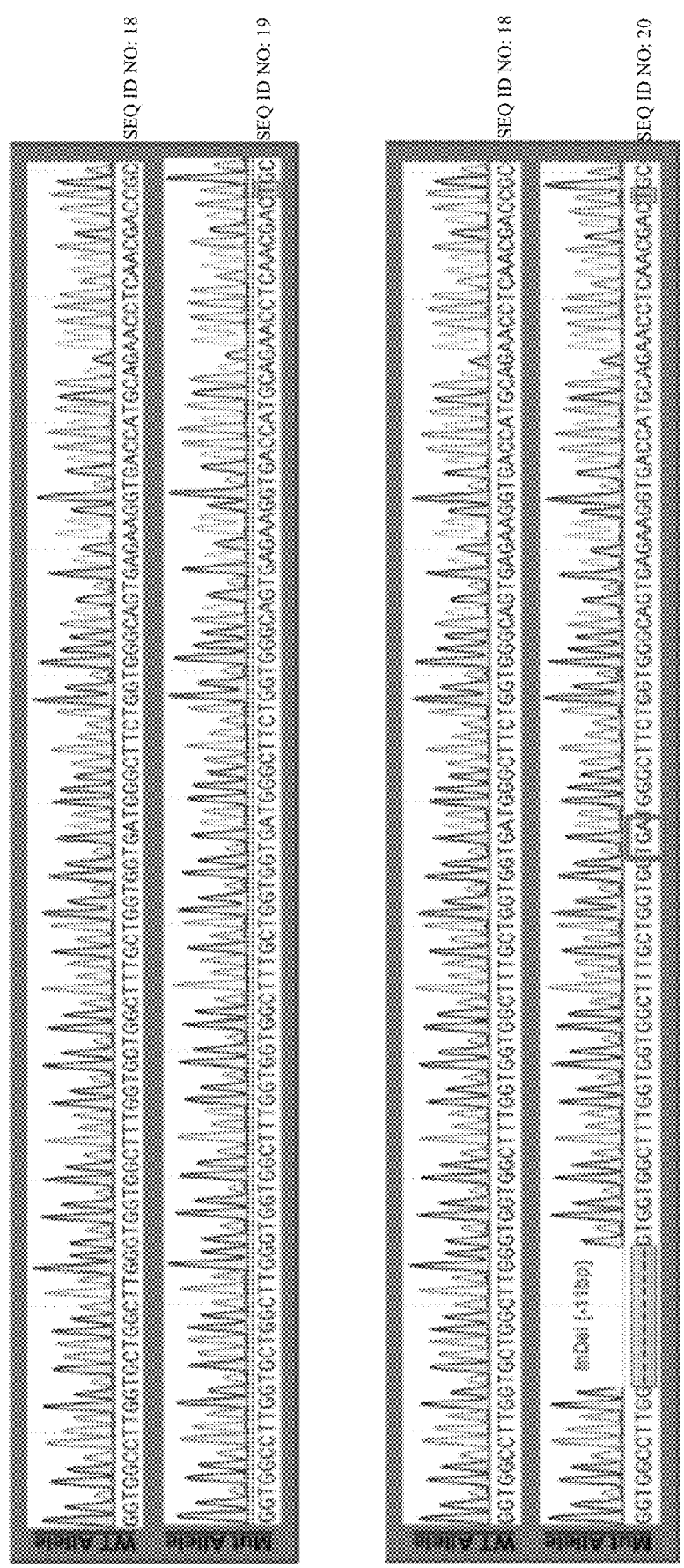

Example 15: Combined Gene Editing and Reprogramming of EBS Patient Derived Fibroblasts Using the combined gene editing and reprogramming approach outlined in FIG. 19, induced pluripotent stem cells were derived that were genetically modified and genetically clonal (FIGS. 31A-31B). The patient had the skin blistering disease Epidermolysis Bullosa simplex (EBS), resulting from a dominant-negative mutation in Keratin 14 (K14$^{c373c>T}$). The mutation was corrected by disrupting expression of the mutant allele by introducing a frame-shift mutation resulting from the treatment with Cas9. In this strategy no repair template (ssODN) was used, therefore the frame-shift mutation resulted from random insertion/deletion events which occur during non-homologous end joining repair of DNA (FIG. 31A). Following genetic editing and reprogramming, iPSC colonies were picked and clonally expanded. A T7 Endonuclease assay was then performed to look for the presence of an INDEL at the K14 locus, indicating possible correction of the patient mutation. A number of clones were then directly sequenced to confirm modification. Furthermore, genetic clonality was determined by Sanger sequencing. The table in FIG. 31A summarizes the findings. Sanger sequencing results from two clonally expanded iPSC lines are illustrated in FIG. 31B. iPSC colony #1 is unmodified. iPSC colony #2 has a frame-shift mutation on the mutant allele of K14. Both lines were genetically clonal.

Figure 32:
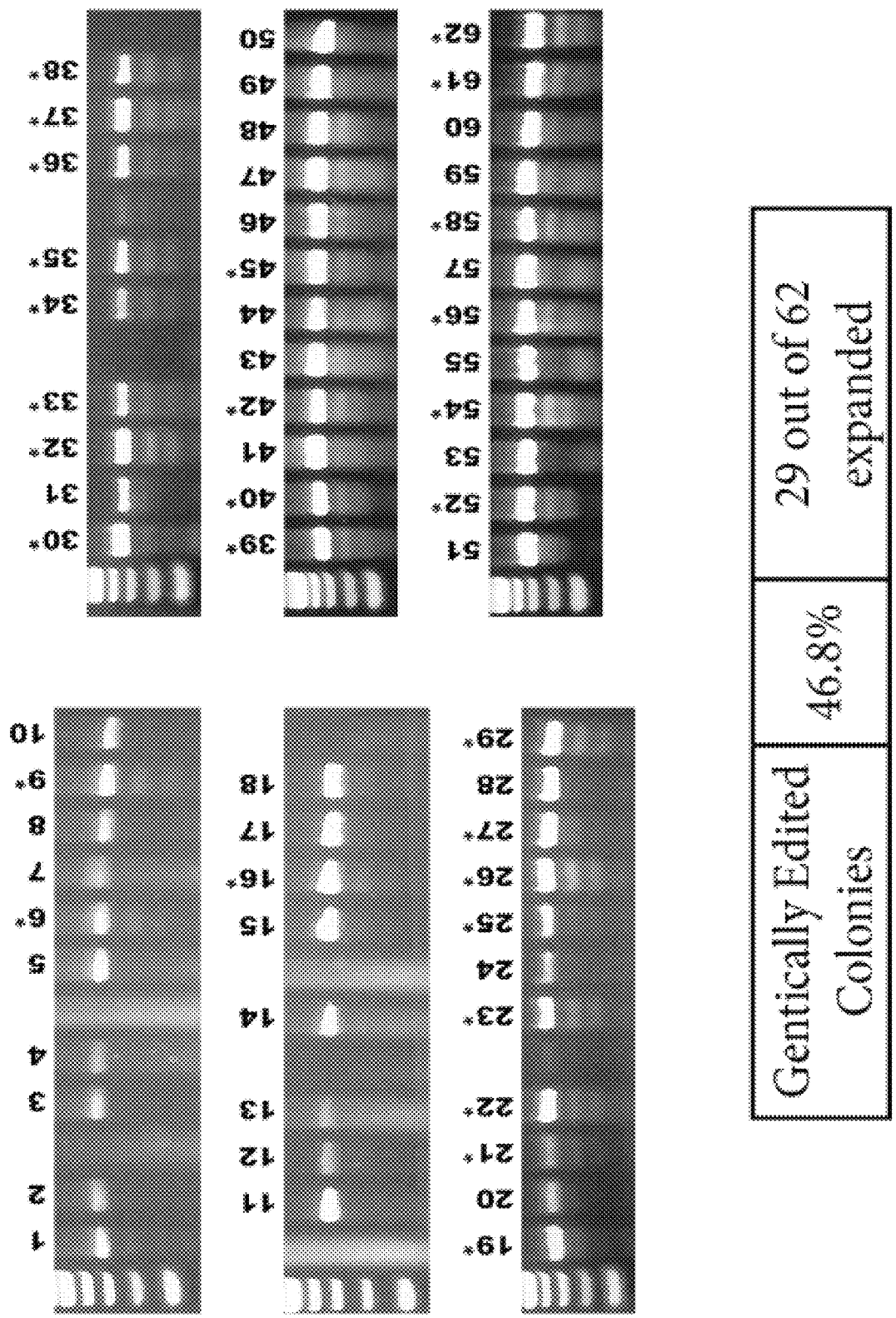
FIG. 32 illustrates combined gene editing and reprogramming of patient derived fibroblasts from a Down Syndrome patient. Using the combined gene editing and reprogramming approach outlined in FIG. 19, induced pluripotent stem cells were derived that were genetically modified and genetically clonal. Following genetic editing and reprogramming, iPSC colonies were picked and clonally expanded. A T7 Endonuclease assay was then performed to look for the presence of an INDEL at the DYRK1A locus, indicating knockout of the gene. The table in the figure summarizes the findings.

Example 16: Combined Gene Editing and Reprogramming of Patient Derived Fibroblasts from a Down Syndrome Patient Using the combined gene editing and reprogramming approach outlined in FIG. 19, induced pluripotent stem cells were derived that were genetically modified and genetically clonal (FIG. 32). This patient has Down Syndrome (Trisomy 21). The goal was to disrupt one or more alleles of DYRK1A, which is on chromosome 21. In this strategy no repair template (ssODN) was used, therefore the frame-shift mutation resulted from random insertion/deletion events which occurred during non-homologous end joining repair of DNA. Following genetic editing and reprogramming, iPSC colonies were picked and clonally expanded. A T7 Endonuclease assay was then performed to look for the presence of an INDEL at the DYRK1A locus, indicating knockout of the gene. The table in FIG. 32 summarizes the findings.

The guide RNAs (gRNAs) used in the present invention can be designed using tools known to one of ordinary skill in the art. However, the invention should not be construed to include only those guide sequences exemplified in the current examples, but rather custom gRNAs can be designed to target any specific sequence relevant to the individual, gene, or disease being treated with the compositions or methods of the present invention. For example, a gRNA can be designed to comprise a nucleotide sequence that is complementary to any mutated target gene of interest. In one non-limiting embodiment, the gRNA comprises the K14 gRNA sequence GGTGGCCTTGGTGCTGGCTTGGG (SEQ ID NO: 1). In another embodiment, the gRNA comprises the COL7A1 gRNA sequence GGGATCCACCGTGAGTCCTCGGG (SEQ ID NO:2). In yet another embodiment, the gRNA comprises the DYRK1A gRNA sequence GCCAAACATAAGTGACCAACAGG (SEQ ID NO:3).

Example 17: Advantages of Combined Cellular Reprogramming and Gene Correction

The present invention includes compositions and methods for simultaneously editing and reprogramming a cell. The protocol utilizes only modified mRNA reagents, which offers many advantages including but not limited to: A.) being transient—limited duration of expression equals limited exposure to reprogramming oncogenes and minimal opportunity for off-target Cas9 cutting. B.) there is no nuclear translocation, which provides more precise dosage control and minimal nuclease-induced toxicity. C.) There is decreased innate immunity activation, and D.) the cells are easy to make and easily compatible with cGMP production.

The use of modified mRNA reagents avoids the drawbacks of other non-integrating strategies such as episomal plasmid (DNA-based), Sendai virus (RNA-based), and self-replicating RNA replicons derived from Venezuelan Encephalitis Virus (RNA-based). Episomal plasmid strategies can have random integration of partial or complete plasmid into the host genome, which is difficult to detect. Random integrations are mutagenic, can interfere with subsequent differentiation, activate innate-immunity triggering apoptosis, or trigger immune reaction following transplantation. Careful screening is required which adds cost and time. Sendai virus—based strategies can result in detectable levels of vector proto-oncogenes and viral antigens even after 10-12 passages. A negative selection clonal-step is required. Continued expression of mRNA vectors/replicons can interfere with subsequent differentiation, activate innate-immunity triggering apoptosis, or trigger immune reaction following transplantation. Careful screening is required, which adds cost and time. Self-replicating RNA replicons derived from Venezuelan Encephalitis Virus include removal of replicating RNA dependent on innate-immunity negative selection. Virus is detectable for up to 8 passages following removal of B18R. The additional time cells are in culture increases the mutational burden, increases cost, and increases time to get the cell therapeutic into a patient.

Other advantages of the compositions and methods of the present invention include: A.) Reprogramming efficiency—A low starting cell number combined with high reprogramming rates yields efficiencies >800% for healthy primary neonatal fibroblast lines. B.) A low number of starting cells is required. Successful reprogramming is achieved from as few as a single cell. The most reproducible results, and highest reprogramming efficiency can be seen using just 3000 cells. C.) The combined approach allows reprogramming of patient lines harboring mutations that otherwise interfere with the generation of stable iPSCs. D.) Monoclonality of derived lines: Genetically identical (clonal) lines are derived following a single clonal outgrowth step. Conventional strategies require at least two clonal outgrowth steps which increases time cells are in culture (increased mutation burden, increased time to get cell therapeutic into a patient, and is expensive).

Another advantage of the methods of the present invention is that no selection is necessary for genetic correction. Correction efficiencies are high enough that no selection strategies are necessary to identify modified clones. This means that HDR correction is scarless and there are no loxp remnants. Piggybac based strategies can be scarless, but there are more required reagents, which add to the cost, and there are sequence constraints so it is not universally applicable for all mutations.

Compositions and methods of the invention are prime for clinical manufacturing. cGMP production costs for IVT mRNA are approximately 5- to 10-fold lower than recombinant proteins produced in eukaryotic cells. The entire combined editing/reprogramming strategy is cGMP compatible. Combined gene editing and reprogramming utilizing solely modified mRNAs yields gene-corrected iPSCs in as little as 3 weeks. This is at least 4 weeks faster than any currently published combined protocol, and 6-12 weeks faster than any potential 2-step approach (reprogramming followed by gene editing). This is important because any additional time cells are in culture increases mutational burden, increases cost, and increases time to get cell therapeutic into a patient who needs a treatment.

Figure 33:
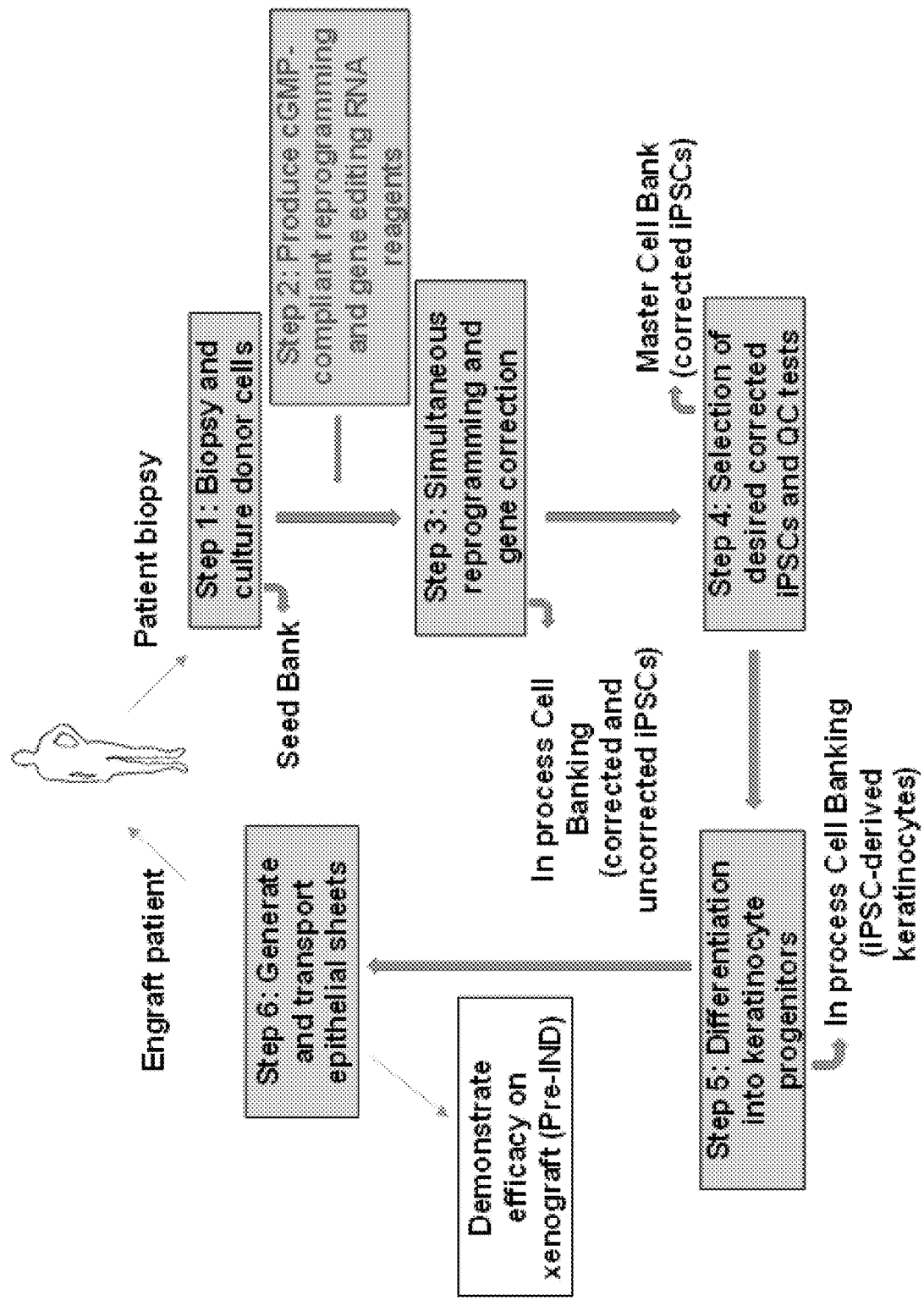
FIG. 33 is a schematic illustrating the steps of manufacturing genetically corrected epidermal sheets for the treatment of inherited skin blistering diseases such as RDEB, JEB, and EBS.

Example 18: Manufacturing Genetically Corrected Epidermal Sheets for the Treatment of RDEB and EBS In certain embodiments, the invention includes iPSCs generated with a highly efficient, integration-free, RNA-based reprogramming approach. Gene correction is performed using viral- and footprint-free CRISPR/Cas9-mediated targeting. Reprogramming and gene editing are combined into a one-step procedure reducing the steps for manufacturing of genetically corrected iPSC-derived epidermal sheets (FIG. 33).

The technological breakthrough that allows adult skin cells to be reprogrammed into induced pluripotent stem cells (iPSC) now offers the possibility of developing a permanent corrective therapy for EB. In a clinical scenario, skin cells can be biopsied from a patient suffering from EB and then "reprogrammed" into iPSCs. The iPSCs can then be grown outside the body, genetically corrected, differentiated into new skin stem cells, and administered back to the same patient as an autograft (FIG. 33). The generation of iPSCs from the same patient in need of treatment would not only avoid the complication of immune rejection, but also provide an unlimited and scalable source of patient-specific cells suitable for transplantation. Despite the almost limitless therapeutic potential of iPSCs for tissue repair, several obstacles must still be overcome before iPSCs can be applied in the clinic. One of these obstacles is the low efficiency and inconsistency of clinically relevant, integration-free approaches for the reprogramming of patient's somatic cells into iPSCs. As demonstrated herein, the reprogramming of a patient's fibroblasts into iPSCs can be significantly enhanced via the synergistic activity of reprogramming modified mRNAs and mature miRNA mimics in combination with optimized culturing conditions. Not only does the protocol consistently generate iPSCs with extremely high efficiency from healthy individuals, but also from adult patients with a variety of disorders, including inherited skin diseases such as EBS and RDEB, as presented herein. All iPSC lines exhibited normal karyotypes and were successfully maintained for at least 15 passages. The pluripotency of the generated iPSCs was confirmed by gene expression analysis and the differentiation into cell types of all three germ layers occurred both in vitro and in vivo. As demonstrated herein, the RNA-based reprogramming was successfully combined with gene correction into a one-step procedure, which allows the simplification of the manufacturing of COL7A1-corrected and K14-corrected autologous iPSCs for clinical applications.

To validate the protocol on a different cell type, urine samples were used as an alternative non-invasive source of somatic cells for reprogramming. As a result, renal epithelial cell lines were successfully established from just 30 ml of urine. The reprogramming protocol was optimized and renal epithelial lines were successfully reprogrammed with the RNA-based approach.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method of reprogramming primary fibroblast cells to a pluripotent state, the method comprising transfecting the primary fibroblast cells seeded at a density of about 1000 cells/cm2 or less in absence of feeder cells and in the absence of treated serum albumin, with a composition comprising a complexation buffer of pH 7.6 to less than pH 8.6 and a reprogramming RNA cocktail, wherein the reprogramming RNA cocktail comprises mRNA encoding Sox2, Klf4, and at least one of Myo-D-Oct4 (M₃O) or Oct4; and editing at least one target nucleotide sequence in at least one target gene in the primary fibroblast cells.

2. The method of claim 1, wherein the reprogramming RNA cocktail comprises at least one of:
   a.) 100 to 1500 ng/10 cm² mRNA;
   b.) mRNA encoding Oct4 or Myo-D-Oct4 (M₃O), Sox2, and Klf4 in a 3:1:1 molar ratio; and
   c.) mRNA encoding one or more of c-Myc, Lin28A, or Nanog in a 1:1 molar ratio with Sox2 and Klf4.

3. The method of claim 1, wherein the reprogramming RNA cocktail of the composition further comprises miRNA or miRNA mimics (m-miRNA).

4. The method of claim 3, wherein the reprogramming RNA cocktail further comprises miRNA or miRNA mimics (m-miRNA) and comprises at least one of:
   a.) 5 to 40 pmoles/10 cm² miRNA; and
   b.) miRNA367, miRNA302a, miRNA302b, miRNA302c, and miRNA302d in a 1:1:1:1:1 molar ratio.

5. The method of claim 1, wherein the complexation buffer has a pH of at least 7.8 to 8.4.

6. The method of claim 1, wherein the transfecting of the primary fibroblast cells is performed:
   a.) at least 3 times,
   b.) every other day for a predetermined period of days but less than 40 days, or
   c.) every third day for a predetermined period of days but less than 40 days.

7. The method of claim 1, wherein the primary fibroblast cells are grown under conditions:
   a.) to increase levels of expression of endogenous pluripotency genes, and to limit the increase in levels of expression of innate immune response genes, or
   b.) to increase cell cycling.

8. The method of claim 1, wherein the primary fibroblast cells are human primary fibroblast cells.

9. The method of claim 1, wherein the primary fibroblast cells comprise a single primary fibroblast cell and the single primary fibroblast cell is reprogrammed to a pluripotent state.

10. The method of claim 9, wherein the reprogramming RNA cocktail further comprises:
   a.) mRNA encoding Oct4 or $M_3O$, Sox2, and Klf4 in a 3:1:1 molar ratio, or
   b.) mRNA encoding one or more of c-Myc, Lin28A, or Nanog in a 1:1 molar ratio with Sox2 and Klf4.

11. The method of claim 9, wherein the reprogramming RNA cocktail further comprises miRNA and the miRNA comprises miRNA367, miRNA302a, miRNA302b, miRNA302c, and miRNA302d in a 1:1:1:1:1 molar ratio.

12. The method of claim 1, wherein editing the at least one target nucleotide sequence of the at least one target gene in the primary fibroblast cells comprises administering to the primary fibroblast cells a Cas9 editing system comprising a Cas9 nuclease and a guide RNA (gRNA), and wherein the at least one target nucleotide sequence in the at least one target gene is edited.

13. The method of claim 1, wherein the primary fibroblast cells are from a mammalian subject generating at least one edited target nucleotide sequence of mammalian subject-specific induced pluripotent stem cells (iPSCs).

14. The method of claim 1, wherein the editing of the target nucleotide sequence comprises at least one of a substitution, an insertion, a deletion, a rearrangement, and a frameshift of the nucleotide sequence.

15. The method of claim 1, wherein the edited target gene is corrected and the correct target gene is bi-allelic.

16. The method of claim 1, wherein the primary fibroblast cells do not undergo a selection after the target nucleotide sequence is edited.

17. The method of claim 1 wherein the editing efficiency is at least 20%, at least 60%, or at least 80%.

18. The method of claim 1, wherein the reprogrammed primary fibroblast cells are cGMP compatible.

19. The method of claim 1, wherein the reprogramming RNA cocktail further comprises Lin28A.

20. The method of claim 1, wherein the reprogramming RNA cocktail further comprises Lin28A and c-Myc.

21. The method of claim 1, wherein the reprogramming RNA cocktail further comprises Lin28A, c-Myc and Nanog.

22. The method of claim 1, wherein transfecting the primary fibroblast cells is in the absence of treated human serum albumin (HSA).

* * * * *